(12) United States Patent
Skelton et al.

(10) Patent No.: US 9,327,070 B2
(45) Date of Patent: May 3, 2016

(54) MEDICAL DEVICE THERAPY BASED ON POSTURE AND TIMING

(75) Inventors: Dennis M. Skelton, Bloomington, MN (US); Jon P. Davis, St. Michael, MN (US); Timothy J. Denison, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 1423 days.

(21) Appl. No.: 12/433,501

(22) Filed: Apr. 30, 2009

(65) Prior Publication Data

US 2010/0280500 A1 Nov. 4, 2010

(51) Int. Cl.
*A61M 5/142* (2006.01)
*A61B 5/00* (2006.01)
*A61B 5/11* (2006.01)
(Continued)

(52) U.S. Cl.
CPC .......... *A61M 5/14276* (2013.01); *A61B 5/7475* (2013.01); *A61N 1/36139* (2013.01); *A61B 5/11* (2013.01); *A61B 5/1116* (2013.01); *A61B 2562/0219* (2013.01); *A61M 2005/14208* (2013.01); *A61M 2210/0693* (2013.01); *A61M 2210/1053* (2013.01);
(Continued)

(58) Field of Classification Search
CPC ............... A61M 5/14276; A61M 2005/14208; A61M 2230/62; A61M 2210/1053; A61M 2210/0693; A61M 2210/1078; A61N 1/36139; A61N 1/37247; A61N 1/36071; A61B 5/7475; A61B 5/1116; A61B 5/11; A61B 2562/0219
USPC ............ 604/891.1, 890.1, 19; 607/17, 62, 46; 128/898
See application file for complete search history.

(56) References Cited

U.S. PATENT DOCUMENTS 4,297,685 A 10/1981 Brainard, II
4,365,633 A 12/1982 Loughman
(Continued)

FOREIGN PATENT DOCUMENTS

DE 19831109 1/2000
DE 10024103 11/2001
(Continued)

OTHER PUBLICATIONS

"Analysis of heart rate dynamics by methods derived from non-linear mathematics: Clinical applicability and prognostic significance," http://herkules.oulu.fi.isbn9514250133/html, 4 pp., 2004.
(Continued)

*Primary Examiner* — Bhisma Mehta
*Assistant Examiner* — Bradley G Thomas, Jr.
(74) *Attorney, Agent, or Firm* — Shumaker & Sieffert, P.A.

(57) ABSTRACT

This disclosure describes techniques implemented by a medical device, such as an implantable medical device (IMD). The IMD may be configured to detect a posture state of a patient, and deliver posture-responsive therapy. In particular, the IMD not only detects the posture state of a patient, but also detects timing associated with the detected posture state, such as the time of day, the day of the week, or a specific time of day associated with a specific day. In this way, the posture-responsive therapy delivered by the IMD may be dependent not only on the posture state of the patient, but also on the timing associated with the posture state. The same posture state, therefore, may result in different types of therapy to the patient if the same posture occurs at different times of the day.

45 Claims, 15 Drawing Sheets

(51) Int. Cl.
*A61N 1/36* (2006.01)
*A61N 1/372* (2006.01)

(52) U.S. Cl.
CPC ... *A61M 2210/1078* (2013.01); *A61M 2230/62* (2013.01); *A61N 1/36071* (2013.01); *A61N 1/37247* (2013.01)

(56) References Cited

U.S. PATENT DOCUMENTS

| | | |
|---|---|---|
| 4,543,955 A | 10/1985 | Schroeppel |
| 4,550,736 A | 11/1985 | Broughton et al. |
| 4,566,456 A | 1/1986 | Koning et al. |
| 4,771,780 A | 9/1988 | Sholder |
| 4,776,345 A | 10/1988 | Cohen et al. |
| 4,846,180 A | 7/1989 | Buffet |
| 4,846,195 A | 7/1989 | Alt |
| 5,031,618 A | 7/1991 | Mullett |
| 5,040,534 A | 8/1991 | Mann et al. |
| 5,040,536 A | 8/1991 | Riff |
| 5,058,584 A | 10/1991 | Bourgeois |
| 5,125,412 A | 6/1992 | Thornton |
| 5,154,180 A | 10/1992 | Blanchet et al. |
| 5,158,078 A | 10/1992 | Bennett et al. |
| 5,167,229 A | 12/1992 | Peckham et al. |
| 5,233,984 A | 8/1993 | Thompson |
| 5,275,159 A | 1/1994 | Griebel |
| 5,312,446 A | 5/1994 | Holschbach et al. |
| 5,335,657 A | 8/1994 | Terry, Jr. et al. |
| 5,337,758 A | 8/1994 | Moore et al. |
| 5,342,409 A | 8/1994 | Mullett |
| 5,354,317 A | 10/1994 | Alt |
| 5,425,750 A | 6/1995 | Moberg |
| 5,476,483 A | 12/1995 | Bornzin et al. |
| 5,487,755 A | 1/1996 | Snell et al. |
| 5,513,645 A | 5/1996 | Jacobson et al. |
| 5,514,162 A | 5/1996 | Bornzin et al. |
| 5,558,640 A | 9/1996 | Pfeiler et al. |
| 5,562,707 A | 10/1996 | Prochazka et al. |
| 5,593,431 A | 1/1997 | Sheldon |
| 5,622,428 A | 4/1997 | Bonnet |
| 5,628,317 A | 5/1997 | Starkebaum et al. |
| 5,643,332 A | 7/1997 | Stein |
| 5,645,053 A | 7/1997 | Remmers et al. |
| 5,674,258 A | 10/1997 | Henschel et al. |
| 5,711,316 A | 1/1998 | Elsberry et al. |
| 5,720,770 A | 2/1998 | Nappholz et al. |
| 5,732,696 A | 3/1998 | Rapoport et al. |
| 5,741,310 A | 4/1998 | Wittkampf |
| 5,782,884 A | 7/1998 | Stotts et al. |
| 5,814,093 A | 9/1998 | Stein |
| 5,832,932 A | 11/1998 | Elsberry et al. |
| 5,833,709 A | 11/1998 | Rise et al. |
| 5,836,989 A | 11/1998 | Shelton |
| 5,851,193 A | 12/1998 | Arikka et al. |
| 5,865,760 A | 2/1999 | Lidman et al. |
| 5,885,471 A | 3/1999 | Ruben et al. |
| 5,893,883 A | 4/1999 | Torgerson et al. |
| 5,895,371 A | 4/1999 | Levitas et al. |
| 5,904,708 A | 5/1999 | Goedeke |
| 5,911,738 A | 6/1999 | Sikorski et al. |
| 5,913,727 A | 6/1999 | Ahdoot |
| 5,919,149 A | 7/1999 | Allum |
| 5,938,690 A | 8/1999 | Law et al. |
| 5,941,906 A | 8/1999 | Barreras, Sr. et al. |
| 5,944,680 A | 8/1999 | Christopherson et al. |
| 5,957,957 A | 9/1999 | Sheldon |
| 6,027,456 A | 2/2000 | Feler et al. |
| 6,038,475 A | 3/2000 | Sikorski et al. |
| 6,044,297 A | 3/2000 | Sheldon et al. |
| 6,045,513 A | 4/2000 | Stone et al. |
| 6,059,576 A | 5/2000 | Brann |
| 6,095,991 A | 8/2000 | Krausman et al. |
| 6,099,479 A | 8/2000 | Christopherson et al. |
| 6,102,874 A | 8/2000 | Stone et al. |
| 6,120,467 A | 9/2000 | Schallhorn |
| 6,128,534 A | 10/2000 | Park et al. |
| 6,134,459 A | 10/2000 | Roberts et al. |
| 6,157,857 A | 12/2000 | Dimpfel |
| 6,165,143 A | 12/2000 | Van Lummel |
| 6,216,537 B1 | 4/2001 | Henschel et al. |
| 6,259,948 B1 | 7/2001 | Florio et al. |
| 6,280,409 B1 | 8/2001 | Stone et al. |
| 6,296,606 B1 | 10/2001 | Goldberg et al. |
| 6,308,098 B1 | 10/2001 | Meyer |
| 6,308,099 B1 | 10/2001 | Fox et al. |
| 6,315,740 B1 | 11/2001 | Singh |
| 6,327,501 B1 | 12/2001 | Levine et al. |
| 6,341,236 B1 | 1/2002 | Osorio et al. |
| 6,351,672 B1 | 2/2002 | Park et al. |
| 6,368,284 B1 | 4/2002 | Bardy |
| 6,381,496 B1 | 4/2002 | Meadows et al. |
| 6,393,325 B1 | 5/2002 | Mann et al. |
| 6,438,408 B1 | 8/2002 | Mulligan et al. |
| 6,440,090 B1 | 8/2002 | Schallhorn |
| 6,449,508 B1 | 9/2002 | Sheldon et al. |
| 6,459,934 B1 | 10/2002 | Kadhiresan |
| 6,466,821 B1 | 10/2002 | Pianca et al. |
| 6,468,234 B1 | 10/2002 | Van der Loos et al. |
| 6,507,757 B1 | 1/2003 | Swain et al. |
| 6,514,218 B2 | 2/2003 | Yamamoto |
| 6,516,749 B1 | 2/2003 | Salasidis |
| 6,539,249 B1 | 3/2003 | Kadhiresan et al. |
| 6,547,755 B1 | 4/2003 | Lippe et al. |
| 6,572,557 B2 | 6/2003 | Tchou et al. |
| 6,574,507 B1 | 6/2003 | Bonnet |
| 6,605,038 B1 | 8/2003 | Teller et al. |
| 6,609,031 B1 | 8/2003 | Law et al. |
| 6,611,783 B2 | 8/2003 | Kelly, Jr. et al. |
| 6,620,151 B2 | 9/2003 | Blischak et al. |
| 6,625,493 B2 | 9/2003 | Kroll et al. |
| 6,635,048 B1 | 10/2003 | Ullestad et al. |
| 6,641,542 B2 | 11/2003 | Cho et al. |
| 6,658,292 B2 | 12/2003 | Kroll et al. |
| 6,659,968 B1 | 12/2003 | McClure |
| 6,662,047 B2 | 12/2003 | Sorensen |
| 6,665,558 B2 | 12/2003 | Kalgren et al. |
| 6,668,188 B2 | 12/2003 | Sun et al. |
| 6,687,538 B1 | 2/2004 | Hrdlicka et al. |
| 6,731,984 B2 | 5/2004 | Cho et al. |
| 6,740,075 B2 | 5/2004 | Lebel et al. |
| 6,748,276 B1 | 6/2004 | Daignault, Jr. et al. |
| 6,751,503 B1 * | 6/2004 | Kroll .............................. 607/18 |
| 6,752,766 B2 | 6/2004 | Kowallik et al. |
| 6,773,404 B2 | 8/2004 | Poezevera et al. |
| 6,782,315 B2 | 8/2004 | Lu et al. |
| 6,817,979 B2 | 11/2004 | Nihtilä |
| 6,820,025 B2 | 11/2004 | Bachmann et al. |
| 6,829,507 B1 | 12/2004 | Lidman et al. |
| 6,832,113 B2 | 12/2004 | Belalcazar |
| 6,834,436 B2 | 12/2004 | Townsend |
| 6,853,863 B2 | 2/2005 | Carter et al. |
| 6,878,121 B2 | 4/2005 | Krausman et al. |
| 6,884,596 B2 | 4/2005 | Civelli et al. |
| 6,890,306 B2 | 5/2005 | Poezevera |
| 6,895,341 B2 | 5/2005 | Barrey et al. |
| 6,922,587 B2 | 7/2005 | Weinberg |
| 6,923,784 B2 | 8/2005 | Stein |
| 6,928,324 B2 | 8/2005 | Park et al. |
| 6,937,899 B2 | 8/2005 | Sheldon et al. |
| 6,937,900 B1 | 8/2005 | Pianca et al. |
| 6,945,934 B2 | 9/2005 | Bardy |
| 6,964,641 B2 | 11/2005 | Cho et al. |
| 6,975,904 B1 | 12/2005 | Sloman |
| 6,997,882 B1 | 2/2006 | Parker et al. |
| 6,999,817 B2 | 2/2006 | Park et al. |
| 7,016,730 B2 | 3/2006 | Ternes |
| 7,031,772 B2 | 4/2006 | Condie |
| 7,043,305 B2 | 5/2006 | KenKnight et al. |
| 7,054,687 B1 | 5/2006 | Andersen |
| 7,066,910 B2 | 6/2006 | Bauhahn et al. |
| 7,082,333 B1 | 7/2006 | Bauhahn |
| 7,092,759 B2 | 8/2006 | Nehls et al. |
| 7,095,424 B2 | 8/2006 | Satoh et al. |

(56) References Cited

U.S. PATENT DOCUMENTS

| | | | |
|---|---|---|---|
| 7,110,820 B2 | 9/2006 | Tcheng et al. |
| 7,117,036 B2 | 10/2006 | Florio |
| 7,123,967 B2 | 10/2006 | Weinberg |
| 7,130,681 B2 | 10/2006 | Gebhardt et al. |
| 7,130,689 B1 | 10/2006 | Turcott |
| 7,141,026 B2 | 11/2006 | Aminian et al. |
| 7,142,921 B2 | 11/2006 | Mattes et al. |
| 7,149,579 B1 | 12/2006 | Koh et al. |
| 7,149,584 B1 | 12/2006 | Koh et al. |
| 7,151,961 B1 | 12/2006 | Whitehurst et al. |
| 7,155,279 B2 | 12/2006 | Whitehurst et al. |
| 7,160,252 B2 | 1/2007 | Cho et al. |
| 7,162,304 B1 | 1/2007 | Bradley |
| 7,167,743 B2 | 1/2007 | Heruth et al. |
| 7,167,751 B1 | 1/2007 | Whitehurst et al. |
| 7,181,281 B1 | 2/2007 | Kroll |
| 7,189,204 B2 | 3/2007 | Ni et al. |
| 7,207,947 B2 | 4/2007 | Koh et al. |
| 7,210,240 B2 | 5/2007 | Townsend et al. |
| 7,212,862 B2 | 5/2007 | Park et al |
| 7,214,197 B2 | 5/2007 | Prass |
| 7,218,964 B2 | 5/2007 | Hill et al. |
| 7,218,968 B2 | 5/2007 | Condie et al. |
| 7,221,979 B2 | 5/2007 | Zhou et al. |
| 7,231,254 B2 | 6/2007 | DiLorenzo |
| 7,242,983 B2 | 7/2007 | Frei et al. |
| 7,252,640 B2 | 8/2007 | Ni et al. |
| 7,266,412 B2 | 9/2007 | Stypulkowski |
| 7,308,311 B2 | 12/2007 | Sorensen et al. |
| 7,313,440 B2 | 12/2007 | Miesel |
| 7,317,948 B1 | 1/2008 | King et al. |
| 7,330,760 B2 | 2/2008 | Heruth et al. |
| 7,366,569 B2 | 4/2008 | Belalcazar |
| 7,366,572 B2 | 4/2008 | Heruth et al. |
| 7,387,610 B2 | 6/2008 | Stahmann |
| 7,389,147 B2 | 6/2008 | Wahlstrand et al. |
| 7,395,113 B2 | 7/2008 | Heruth |
| 7,403,820 B2 | 7/2008 | DiLorenzo |
| 7,406,351 B2 | 7/2008 | Wesselink |
| 7,415,308 B2 | 8/2008 | Gerber et al. |
| 7,447,545 B2 | 11/2008 | Heruth et al. |
| 7,471,290 B2 | 12/2008 | Wang et al. |
| 7,471,980 B2 | 12/2008 | Koshiol |
| 7,489,970 B2 | 2/2009 | Lee et al. |
| 7,491,181 B2 | 2/2009 | Heruth et al. |
| 7,505,815 B2 | 3/2009 | Lee et al. |
| 7,519,431 B2 | 4/2009 | Goetz et al. |
| 7,542,803 B2 | 6/2009 | Heruth et al. |
| 7,548,786 B2 | 6/2009 | Lee et al. |
| 7,559,901 B2 | 7/2009 | Maile |
| 7,572,225 B2 | 8/2009 | Stahmann |
| 7,577,479 B2 | 8/2009 | Hartley et al. |
| 7,580,752 B2 | 8/2009 | Gerber et al. |
| 7,584,808 B2 | 9/2009 | Dolgin et al. |
| 7,590,453 B2 | 9/2009 | Heruth |
| 7,590,455 B2 | 9/2009 | Heruth et al. |
| 7,590,481 B2 | 9/2009 | Lu et al. |
| 7,591,265 B2 | 9/2009 | Lee et al. |
| 7,603,170 B2 | 10/2009 | Hatlestad et al. |
| 7,623,919 B2 | 11/2009 | Goetz et al. |
| 7,634,379 B2 | 12/2009 | Noble |
| 7,664,546 B2 | 2/2010 | Hartley et al. |
| 7,672,806 B2 | 3/2010 | Tronconi |
| 7,717,848 B2 | 5/2010 | Heruth et al. |
| 7,769,464 B2 | 8/2010 | Gerber et al. |
| 7,792,583 B2 | 9/2010 | Heruth et al. |
| 7,822,481 B2 * | 10/2010 | Gerber et al. ............ 607/62 |
| 7,996,070 B2 | 8/2011 | van Dam et al. |
| 2002/0038137 A1 | 3/2002 | Stein |
| 2002/0091308 A1 | 7/2002 | Kipshidze et al. |
| 2002/0107553 A1 | 8/2002 | Hill et al. |
| 2002/0115939 A1 | 8/2002 | Mulligan et al. |
| 2002/0165586 A1 | 11/2002 | Hill et al. |
| 2002/0169485 A1 | 11/2002 | Pless et al. |
| 2002/0170193 A1 | 11/2002 | Townsend et al. |
| 2003/0004423 A1 | 1/2003 | Lavie et al. |
| 2003/0036783 A1 | 2/2003 | Bauhahn et al. |
| 2003/0045910 A1 | 3/2003 | Sorensen et al. |
| 2003/0065370 A1 | 4/2003 | Lebel et al. |
| 2003/0088185 A1 | 5/2003 | Prass |
| 2003/0149457 A1 | 8/2003 | Tcheng et al. |
| 2003/0171791 A1 | 9/2003 | KenKnight et al. |
| 2003/0181960 A1 | 9/2003 | Carter et al. |
| 2003/0204211 A1 | 10/2003 | Condie et al. |
| 2004/0015103 A1 | 1/2004 | Aminian et al. |
| 2004/0049132 A1 | 3/2004 | Barron et al. |
| 2004/0088020 A1 | 5/2004 | Condie et al. |
| 2004/0102814 A1 | 5/2004 | Sorensen et al. |
| 2004/0133248 A1 | 7/2004 | Frei et al. |
| 2004/0138716 A1 | 7/2004 | Kon et al. |
| 2004/0147975 A1 | 7/2004 | Popovic et al. |
| 2004/0199215 A1 | 10/2004 | Lee et al. |
| 2004/0199216 A1 | 10/2004 | Lee et al. |
| 2004/0199217 A1 | 10/2004 | Lee et al. |
| 2004/0199218 A1 | 10/2004 | Lee et al. |
| 2004/0215286 A1 | 10/2004 | Stypulkowski |
| 2004/0220621 A1 | 11/2004 | Zhou et al. |
| 2004/0225332 A1 | 11/2004 | Gebhardt et al. |
| 2004/0257693 A1 | 12/2004 | Ehrlich |
| 2005/0042589 A1 | 2/2005 | Hatlestad et al. |
| 2005/0043767 A1 | 2/2005 | Belalcazar |
| 2005/0060001 A1 | 3/2005 | Singhal et al. |
| 2005/0061320 A1 | 3/2005 | Lee et al. |
| 2005/0113710 A1 | 5/2005 | Stahmann et al. |
| 2005/0113887 A1 | 5/2005 | Bauhahn et al. |
| 2005/0126026 A1 | 6/2005 | Townsend et al. |
| 2005/0137627 A1 | 6/2005 | Koshiol et al. |
| 2005/0145246 A1 | 7/2005 | Hartley et al. |
| 2005/0172311 A1 | 8/2005 | Hjelt et al. |
| 2005/0177192 A1 | 8/2005 | Rezai et al. |
| 2005/0209511 A1 | 9/2005 | Heruth et al. |
| 2005/0209512 A1 | 9/2005 | Heruth et al. |
| 2005/0209513 A1 | 9/2005 | Heruth et al. |
| 2005/0209643 A1 | 9/2005 | Heruth et al. |
| 2005/0209644 A1 | 9/2005 | Heruth et al. |
| 2005/0209645 A1 * | 9/2005 | Heruth et al. ............ 607/3 |
| 2005/0215847 A1 | 9/2005 | Heruth et al. |
| 2005/0215947 A1 | 9/2005 | Heruth et al. |
| 2005/0216064 A1 | 9/2005 | Heruth et al. |
| 2005/0222522 A1 | 10/2005 | Heruth et al. |
| 2005/0222638 A1 | 10/2005 | Foley et al. |
| 2005/0228455 A1 | 10/2005 | Kramer et al. |
| 2005/0234514 A1 | 10/2005 | Heruth et al. |
| 2005/0234518 A1 | 10/2005 | Heruth et al. |
| 2005/0240242 A1 | 10/2005 | DiLorenzo et al. |
| 2005/0245988 A1 | 11/2005 | Miesel |
| 2005/0283210 A1 | 12/2005 | Blischak et al. |
| 2006/0190049 A1 | 8/2006 | Gerber et al. |
| 2006/0190050 A1 | 8/2006 | Gerber et al. |
| 2006/0190051 A1 | 8/2006 | Gerber et al. |
| 2006/0195051 A1 | 8/2006 | Schnapp et al. |
| 2006/0206167 A1 | 9/2006 | Flaherty et al. |
| 2006/0212080 A1 | 9/2006 | Hartley et al. |
| 2006/0213267 A1 | 9/2006 | Tronconi et al. |
| 2006/0235289 A1 | 10/2006 | Wesselink et al. |
| 2006/0235472 A1 | 10/2006 | Goetz et al. |
| 2006/0241513 A1 | 10/2006 | Hatlestad et al. |
| 2006/0247732 A1 | 11/2006 | Wesselink |
| 2006/0247739 A1 | 11/2006 | Wahlstrand et al. |
| 2006/0259099 A1 | 11/2006 | Goetz et al. |
| 2006/0262120 A1 | 11/2006 | Rosenberg |
| 2006/0265025 A1 | 11/2006 | Goetz et al. |
| 2006/0276848 A1 * | 12/2006 | Min et al. ............ 607/17 |
| 2006/0287686 A1 | 12/2006 | Cullen et al. |
| 2007/0015976 A1 | 1/2007 | Miesel et al. |
| 2007/0038265 A1 | 2/2007 | Tcheng et al. |
| 2007/0050715 A1 | 3/2007 | Behar |
| 2007/0073355 A1 | 3/2007 | DiLorenzo et al |
| 2007/0115277 A1 | 5/2007 | Wang et al. |
| 2007/0118056 A1 | 5/2007 | Wang et al. |
| 2007/0123758 A1 | 5/2007 | Miesel et al. |
| 2007/0129622 A1 | 6/2007 | Bourget et al. |
| 2007/0129641 A1 | 6/2007 | Sweeney |
| 2007/0129769 A1 | 6/2007 | Bourget et al. |

(56) References Cited

U.S. PATENT DOCUMENTS

| | | |
|---|---|---|
| 2007/0129774 A1 | 6/2007 | Bourget et al. |
| 2007/0150026 A1 | 6/2007 | Bourget et al. |
| 2007/0150029 A1* | 6/2007 | Bourget et al. ............ 607/62 |
| 2007/0213789 A1 | 9/2007 | Nolan et al. |
| 2007/0249968 A1 | 10/2007 | Miesel et al. |
| 2007/0250121 A1 | 10/2007 | Miesel et al. |
| 2007/0250134 A1 | 10/2007 | Miesel et al. |
| 2007/0255118 A1 | 11/2007 | Miesel et al. |
| 2007/0255154 A1 | 11/2007 | Lu et al. |
| 2007/0265664 A1 | 11/2007 | Gerber et al. |
| 2007/0265681 A1 | 11/2007 | Gerber et al. |
| 2007/0276439 A1 | 11/2007 | Miesel et al. |
| 2007/0293737 A1 | 12/2007 | Heruth et al. |
| 2007/0293917 A1 | 12/2007 | Thompson |
| 2008/0071150 A1 | 3/2008 | Miesel et al. |
| 2008/0071324 A1 | 3/2008 | Miesel et al. |
| 2008/0071326 A1 | 3/2008 | Heruth et al. |
| 2008/0071327 A1 | 3/2008 | Miesel et al. |
| 2008/0079444 A1 | 4/2008 | Denison |
| 2008/0081958 A1 | 4/2008 | Denison et al. |
| 2008/0114219 A1* | 5/2008 | Zhang et al. ............ 600/301 |
| 2008/0164979 A1 | 7/2008 | Otto |
| 2008/0177355 A1 | 7/2008 | Miesel et al. |
| 2008/0188901 A1 | 8/2008 | Sanghera et al. |
| 2008/0188909 A1 | 8/2008 | Bradley |
| 2008/0194998 A1 | 8/2008 | Holmstrom et al. |
| 2008/0204255 A1 | 8/2008 | Flexer et al. |
| 2008/0269812 A1 | 10/2008 | Gerber et al. |
| 2008/0269843 A1 | 10/2008 | Gerber |
| 2008/0281376 A1 | 11/2008 | Gerber et al. |
| 2008/0281379 A1 | 11/2008 | Wesselink |
| 2008/0281381 A1 | 11/2008 | Gerber et al. |
| 2008/0288200 A1 | 11/2008 | Noble |
| 2008/0300449 A1 | 12/2008 | Gerber et al. |
| 2008/0300470 A1 | 12/2008 | Gerber et al. |
| 2009/0030263 A1 | 1/2009 | Heruth et al. |
| 2009/0036951 A1 | 2/2009 | Heruth et al. |
| 2009/0046056 A1 | 2/2009 | Rosenberg et al. |
| 2009/0076343 A1 | 3/2009 | James et al. |
| 2009/0082829 A1 | 3/2009 | Panken et al. |
| 2009/0099627 A1 | 4/2009 | Molnar et al. |
| 2009/0105785 A1 | 4/2009 | Wei et al. |
| 2009/0118599 A1 | 5/2009 | Heruth et al. |
| 2009/0228841 A1 | 9/2009 | Hildreth |
| 2009/0233770 A1 | 9/2009 | Vincent et al. |
| 2009/0259216 A1 | 10/2009 | Drew et al. |
| 2009/0264789 A1 | 10/2009 | Molnar et al. |
| 2009/0306740 A1 | 12/2009 | Heruth et al. |
| 2010/0010380 A1 | 1/2010 | Panken et al. |
| 2010/0010381 A1 | 1/2010 | Skelton et al. |
| 2010/0010382 A1 | 1/2010 | Panken et al. |
| 2010/0010383 A1 | 1/2010 | Skelton et al. |
| 2010/0010384 A1 | 1/2010 | Panken et al. |
| 2010/0010385 A1 | 1/2010 | Skelton et al. |
| 2010/0010386 A1 | 1/2010 | Skelton et al. |
| 2010/0010387 A1 | 1/2010 | Skelton et al. |
| 2010/0010388 A1 | 1/2010 | Panken et al. |
| 2010/0010389 A1 | 1/2010 | Davis et al. |
| 2010/0010390 A1 | 1/2010 | Skelton et al. |
| 2010/0010391 A1 | 1/2010 | Skelton et al. |
| 2010/0010392 A1 | 1/2010 | Skelton et al. |
| 2010/0010432 A1 | 1/2010 | Skelton et al. |
| 2010/0010571 A1 | 1/2010 | Skelton et al. |
| 2010/0010572 A1 | 1/2010 | Skelton et al. |
| 2010/0010573 A1 | 1/2010 | Skelton et al. |
| 2010/0010574 A1 | 1/2010 | Skelton et al. |
| 2010/0010575 A1 | 1/2010 | Skelton et al. |
| 2010/0010576 A1 | 1/2010 | Skelton et al. |
| 2010/0010577 A1 | 1/2010 | Skelton et al. |
| 2010/0010578 A1 | 1/2010 | Skelton et al. |
| 2010/0010579 A1 | 1/2010 | Skelton et al. |
| 2010/0010580 A1 | 1/2010 | Skelton et al. |
| 2010/0010583 A1 | 1/2010 | Panken et al. |
| 2010/0010584 A1 | 1/2010 | Skelton et al. |
| 2010/0010585 A1 | 1/2010 | Davis et al. |
| 2010/0010586 A1 | 1/2010 | Skelton et al. |
| 2010/0010587 A1 | 1/2010 | Skelton et al. |
| 2010/0010588 A1 | 1/2010 | Skelton et al. |
| 2010/0010589 A1 | 1/2010 | Skelton et al. |
| 2010/0010590 A1 | 1/2010 | Skelton et al. |
| 2010/0030286 A1 | 2/2010 | Goetz et al. |
| 2010/0121415 A1 | 5/2010 | Skelton et al. |
| 2010/0174155 A1 | 7/2010 | Heruth et al. |

FOREIGN PATENT DOCUMENTS

| | | |
|---|---|---|
| EP | 0564803 | 10/1993 |
| EP | 0845240 | 6/1998 |
| EP | 0849715 | 6/1998 |
| EP | 1195139 | 4/2002 |
| EP | 1291036 | 3/2003 |
| EP | 1308182 | 5/2003 |
| EP | 1391846 | 2/2004 |
| EP | 1437159 | 7/2004 |
| EP | 1731088 | 12/2006 |
| EP | 1870128 | 12/2007 |
| EP | 1938862 | 7/2008 |
| GB | 2330912 | 5/1999 |
| GB | 2408342 | 5/2005 |
| GB | 2447647 | 9/2008 |
| WO | 94/05371 | 3/1994 |
| WO | 96/29007 | 9/1996 |
| WO | 97/04705 | 2/1997 |
| WO | 97/49455 | 12/1997 |
| WO | 98/00197 | 1/1998 |
| WO | 99/56820 | 11/1999 |
| WO | 01/37930 | 5/2001 |
| WO | 02/28282 | 4/2002 |
| WO | 02/41771 | 5/2002 |
| WO | 02/087433 | 11/2002 |
| WO | 02/096512 | 12/2002 |
| WO | 02/100267 | 12/2002 |
| WO | 03/051356 | 6/2003 |
| WO | 03/065891 | 8/2003 |
| WO | 2005/028029 | 3/2005 |
| WO | 2005/035050 | 4/2005 |
| WO | 2005/079487 | 9/2005 |
| WO | 2005/089646 | 9/2005 |
| WO | 2005/089647 | 9/2005 |
| WO | 2005/089860 | 9/2005 |
| WO | 2005/102499 | 11/2005 |
| WO | 2005/120348 | 12/2005 |
| WO | 2007/009088 | 1/2007 |
| WO | 2007/051196 | 5/2007 |
| WO | 2007/064682 | 6/2007 |
| WO | 2007/064936 | 6/2007 |
| WO | 2008/026970 | 3/2008 |

OTHER PUBLICATIONS

"Design Competition: Runners-Up for the Best Three Designs," EPN, vol. 26, No. 1, 1 pg., 2002.

"IBM and Citizen Watch develop Linux-Based WatchPad," http://wwwlinuxdevices.com/news/NS6580187845.html, 5 pp., 2006.

"MiniMitter® Physiological and Behavioral Monitoring for Humans and Animals," http://www.minimitter.com/Products/Actiwatch, 3 pp., 2006.

"Watch," Wikipedia, 6 pp., http://en.wikipedia.org/wiki/Watch, 2006

Aminian et al., "Physical Activity Monitoring Based on Accelerometry: Validation and Comparison with Video Observation," Medical & Biological Engineering and Computing, vol. 37, No. 2, pp. 304-308, 1999.

Amzica, "Physiology of Sleep and Wakefulness as it Relates to the Physiology of Epilepsy," Journal of Clinical Neurophysiology, American Clinical Neurophysiology Society, 19(6)1, pp. 488-503, 2002.

Ang et al., "Physical model of a MEMS accelerometer for low-g motion tracking applications," 2004 IEEE International Conference on Robotics and Automation, vol. 2, pp. 1345-1351, 2004.

Buchser et al., "Improved Physical Activity in Patients Treated for Chronic Pain by Spinal Cord Stimulation," Neuromodulation, vol. 8, Issue 1, pp. 40-48, Mar. 2005.

(56) References Cited

OTHER PUBLICATIONS

Crago et al., "An Elbow Extension Neuroprosthesis for Individuals with Tetraplegia," IEEE Transactions on Rehabilitation Engineering, vol. 6, No. 1, pp. 1-6, Mar. 1998.
Dejnabadi et al., "Estimation and Visualization of Sagittal Kinematics of Lower Limbs Orientation Using Body-Fixed Sensors," IEEE Transactions on Biomedical Engineering, vol. 53, No. 7, pp. 1385-1393, Jul. 2006.
Dinner, "Effect of Sleep on Epilepsy," Journal of Clinical Neurophysiology, American Clinical Neurophysiology Society, 19(6), pp. 504-513, 2002.
Foerster et al., "Motion Pattern and Posture: Correctly Assessed by Calibrated Accelerometers," Forschungsgrupe Psychophysiologie, Universität Freiburg, Germany, Mar. 2000, 28 pp.
Foldvary-Schaefer, "Sleep Complaints and Epilepsy: The Role of Seizures, Antiepileptic Drugs and Sleep Disorders," Journal of Clinical Neurophysiology, American Clinical Neurophysiology Society, 19(6), pp. 514-521, 2002.
Fourcade et al., "Modeling Phase Transitions in Human Posture," Studies in Perception and Action VII, Sheena Rogers & Judith Effken (eds), Lawrence Erlbaum Associated, Inc., pp. 99-103, 2003.
Giansanti et al., "The development and test of a device for the reconstruction of 3-D position and orientation by means of a kinematic sensor assembly with rate gyroscopes and accelerometers," IEEE Transactions on Biomedical Engineering, v. 52, No. 7, pp. 1271-1277, Jul. 2005.
Goodrich et al., "The Prediction of Pain Using Measures of Sleep Quality," Pain Digest, 8:23-25, 1998.
Heinz et al., "Using Wearable Sensors for Real-time Recognition Tasks in Games of Martial Arts—An Initial Experiment," Institute for Computer Systems and Networks (CSN), UMIT—University of Health Systems, Medical Informatics and Technology Hall in Tyrol, Austria, 2006 5 pp. http://eis.comp.lancs.ac.uk/fileadmin/relate/publication/2006-WearableSensors.pdf.
Hendelman et al., "Validity of Accelerometry for the Assessment of Moderate Intensity Physical Activity in the Field," Medicine & Science in Sports & Exercise, pp. S442-S449, 2000.
Hinckley, K., Pierce, J., Sinclair, M., Horvitz, E., *Sensing Techniques for Mobile Interaction*, ACM UIST 2000 Symposium on User Interface Software & Technology, CHI Letters 2 (2), pp. 91-100.
Husak, "Model of Tilt Sensor Systems," ICECS 2002, $9^{th}$ IEEE International Conference on Electronics, Circuits and Systems, vol. 1, pp. 227-230, 2002.
Karantonis et al., "Implementation of a Real-Time Human Movement Classifier Using a Triaxial Accelerometer for Ambulatory Monitoring," IEEE Transactions on Information Technology in Biomedicine, vol. 10, No. 1, pp. 156-167, Jan. 2006.
Kassam, "2005 EDP Topic "MK4": Tremor Data-Logger for Parkinson's Disease Patients," http://www.ee.ryerson.ca/~courses/edp2005/MK4.html, 3 pp., 2005.
Kerr et al., "Analysis of the sit-stand-sit movement cycle in normal subjects," Clinical Biomechanics, vol. 12, No. 4, pp. 236-245, 1977.
Kiani et al., "Computerized Analysis of Daily Life Motor Activity for Ambulatory Monitoring," Technology and Health Care 5, pp. 307-318, 1997.
Lau, "Strategies for Generating Prolonged Functional Standing Using Intramuscular Stimulation or Intraspinal Microstimulation," IEEE Transactions on Neural Systems and Rehabilitation Engineering, vol. 15 No. 2, pp. 273-285, Jun. 2007.
Leiper et al., "Sensory Feedback for Head Control in Cerebral Palsy," Physical Therapy, vol. 61, No. 4, pp. 512-518, Apr. 1981.
Lorussi, "Wearable, Redundant Fabric-Based Sensor Arrays for Reconstruction of Body Segment Posture," IEEE Sensors Journal, vol. 4, No. 6, pp. 808-817, Dec. 2004.
Mathie et al., "A Pilot Study of Long-Term Monitoring of Human Movements in the Home Using Accelerometer," Journal of Telemedicine and Telecare10:144-151, Jun. 2007.
Mathie et al., "Determining Activity Using a Triaxial Accelerometer," Proceedings of the Second Joint EMBS/BMES Conference, Houston, TX, pp. 2481-2482, Oct. 23-26, 2002.
Mattmann et al., "Recognizing Upper Body Postures Using Textile Strain Sensors," Proceedings Eleventh IEEE International Symposium on Wearable Computers, ISWC, pp. 29-36, 2007.
Mendez et al., "Interactions Between Sleep and Epilepsy," Journal of Clinical Neurophysiology, American Clinical Neurophysiology Society, 18(2), pp. 106-127, 2001.
Paraschiv-Ionescu et al., "Ambulatory System for the Quantitative and Qualitative Analysis of Patients Treated with Spinal Cord Stimulation," Gait and Posture, vol. 20, Issue 2, pp. 113-125, Oct. 2004.
Slyper et al., "Action Capture with Accelerometers," Eurographics/ACM SIGGRAPH Symposium on Computer Animation, Carnegie Mellon University, 7 pp. 2008.
Smith et al., "How do sleep disturbance and chronic pain inter-relate? Insights from the longitudinal and cognitive-behavioral clinical trials literature," Sleep Medicine Reviews, YSMRV 286, pp. 1-14, 2003.
Smith et al., "Presleep cognitions in Patients with Insomnia Secondary to Chronic Pain," Journal of Behavioral Medicine, vol. 24, No. 1, pp. 93-114, 2001.
Emmanuel Munguia Tapia, "Activity Recognition from Accelerometer Data for Videogame Applications," http://alumni.media.mit.edu/~emunguia/html/videogames.htm, 7 pp., Dec. 2, 2003, printed Oct. 1, 2009.
Trolier-Mckinstry et al., "Thin Film Piezoelectrics for MEMS," Journal of Electroceramics, v. 12, No. 1-2, pp. 7-17, Jan./Mar. 2004.
Tuck, "Implementing Auto-Zero Calibration Technique for Accelerometers," Freescale Semiconductor Application Note AN3447, 5 pp., Mar. 2007.
Tuisku, "Motor Activity Measured by Actometry in Neuropsychiatric Disorders," Department of Psychiatry, University of Helsinki, Helsinki, Finland, 115 pp., 2002.
Vega-Gonzalez, "Upper Limb Activity Monitoring," Arch Phys Med Rehabil, vol. 86, pp. 541-548, Mar. 2005.
Velten et al., "A New Three-Axis Accelerometer," Sensor '99—$9^{th}$ Int'l Traide Fair and Conference for Sensors/Transducers & Systems, Nürnberg, Germany, May 18-20, 1999, Sensor '99 Proceedings II, A 5.2, pp. 47-52, 1999.
PCT/US09/49393: International Search Report and Written Opinion dated May 7, 2010, 14 pp.
U.S. Appl. No. 12/815,834, filed Jun. 15, 2010, Gerber et al.
U.S. Appl. No. 12/433,856, filed Apr. 30, 2009, Skelton et al.
U.S. Appl. No. 12/433,750, filed Apr. 30, 2009, Skelton et al.
U.S. Appl. No. 12/433,103, filed Apr. 30, 2009, Skelton et al.
U.S. Appl. No. 12/433,632, filed Apr. 30, 2009, Skelton et al.
U.S. Appl. No. 12/433,558, filed Apr. 30, 2009, Skelton et al.
U.S. Appl. No. 12/433,623, filed Apr. 30, 2009, Skelton et al.
U.S. Appl. No. 12/433,854, filed Apr. 30, 2009, Skelton et al.
U.S. Appl. No. 12/433,749, filed Apr. 30, 2009, Skelton et al.
U.S. Appl. No. 12/433,855, filed Apr. 30, 2009, Skelton et al.
U.S. Appl. No. 12/433,520, filed Apr. 30, 2009, Skelton.
U.S. Appl. No. 12/433,551, filed Apr. 30, 2009, Davis et al.
U.S. Appl. No. 12/433,588, filed Apr. 30, 2009, Skelton et al.
U.S. Appl. No. 12/433,599, filed Apr. 30, 2009, Skelton et al.
U.S. Appl. No. 12/433,442, filed Apr. 30, 2009, Skelton et al.
U.S. Appl. No. 12/433,756, filed Apr. 30, 2009, Panken et al.
U.S. Appl. No. 12/433,808, filed Apr. 30, 2009, Skelton et al.
U.S. Appl. No. 12/433,725, filed Apr. 30, 2009, Skelton et al.
U.S. Appl. No. 12/433,530, filed Apr. 30, 2009, Skelton et al.
U.S. Appl. No. 12/433,325, filed Apr. 30, 2009, Skelton et al.
U.S. Appl. No. 12/433,373, filed Apr. 30, 2009, Skelton et al.
U.S. Appl. No. 12/433,651, filed Apr. 30, 2009, Skelton et al.
U.S. Appl. No. 12/433,673, filed Apr. 30, 2009, Skelton et al.
U.S. Appl. No. 12/433,785, filed Apr. 30, 2009, Davis et al.
U.S. Appl. No. 12/433,827, filed Apr. 30, 2009, Skelton et al.
U.S. Appl. No. 12/433,848, filed Apr. 30, 2009, Skelton et al.
U.S. Appl. No. 12/433,840, filed Apr. 30, 2009, Skelton et al.
U.S. Appl. No. 12/433,839, filed Apr. 30, 2009, Skelton et al.
U.S. Appl. No. 12/433,803, filed Apr. 30, 2009, Skelton et al.
U.S. Appl. No. 12/433,815, filed Apr. 30, 2009, Skelton et al.
U.S. Appl. No. 12/433,684, filed Apr. 30, 2009, Skelton et al.
U.S. Appl. No. 12/771,854, filed Apr. 30, 2010, Skelton.
U.S. Appl. No. 12/433,017, filed Apr. 30, 2009, Skelton et al.
U.S. Appl. No. 12/433,004, filed Apr. 30, 2009, Panken et al.
U.S. Appl. No. 12/548,227, filed Aug. 26, 2009, Skelton et al.

(56) References Cited

OTHER PUBLICATIONS

U.S. Appl. No. 12/433,038, filed Apr. 30, 2009, Panken.
U.S. Appl. No. 12/433,029, filed Apr. 30, 2009, Panken et al.
U.S. Appl. No. 12/432,993, filed Apr. 30, 2010, Panken et al.
U.S. Appl. No. 12/769,461, filed Apr. 28, 2010, Sahasrabudhe et al.
U.S. Appl. No. 12/769,391, filed Apr. 28, 2010, Sahasrabudhe et al.
U.S. Appl. No. 12/769,484, filed Apr. 28, 2010, Panken et al.
Office Action dated Dec. 19, 2011, for U.S. Appl. No. 12/433,684, (9 pgs.).
Responsive Amendment dated Mar. 19, 2012 U.S. Appl. No. 12/433,684, (12 pgs.).
Office Action dated Jun. 21, 2011 for U.S. Appl. No. 12/433,684, (8 pgs).
Responsive Amendment dated Sep. 21, 2011 U.S. Appl. No. 12/433,684 (13 pgs.).
Response dated Jul. 25, 2012 for U.S. Appl. No. 12/433,684, (6 pgs.).
Final Office Action dated May 25, 2012 for U.S. Appl. No. 12/433,684, (8 pgs.).
Notice of Allowance from U.S. Appl. No. 12/433,684 dated Jun. 24, 2014, 8 pp.

* cited by examiner

MEDICAL DEVICE THERAPY BASED ON POSTURE AND TIMING

TECHNICAL FIELD

The disclosure relates to medical devices and, more particularly, to programmable medical devices that deliver therapy.

BACKGROUND

A variety of medical devices are used for delivery of therapy to patients suffering from a variety of conditions, such as chronic pain, tremor, Parkinson's disease, epilepsy, urinary or fecal incontinence, sexual dysfunction, obesity, or gastroparesis. As examples, electrical stimulation generators are used for chronic delivery of electrical stimulation therapies such as cardiac pacing, neurostimulation, muscle stimulation, or the like. Pumps or other fluid delivery devices may be used for chronic delivery of therapeutic agents, such as drugs. Typically, such devices provide therapy continuously or periodically according to parameters contained within a program. A program may comprise respective values for each of a plurality of parameters, specified by a clinician.

In some cases, the patient may be allowed to activate and/or modify the therapy delivered by the medical device. For example, a patient may use a patient programming device to activate and/or modify the therapy of a medical device. The patient programming device communicates with a medical device to allow for therapy activation, and/or adjustments to therapy parameters. For example, an implantable medical device (IMD), such as an implantable neurostimulator, may be accompanied by an external patient programmer that permits the patient to activate and deactivate neurostimulation therapy and/or adjust the intensity of the delivered neurostimulation. The patient programmer may communicate with the IMD via wireless telemetry to control the IMD and/or retrieve information from the IMD.

SUMMARY

In general, this disclosure describes techniques implemented by an implantable medical device (IMD), such as an implantable stimulator device or an implantable drug pump, or possibly by a programmer device of the IMD. In accordance with this disclosure, the IMD is configured to detect a posture state of a patient, detect timing associated with the posture state, and deliver posture-responsive therapy based on the posture state and the timing. In particular, the IMD not only detects the posture state of a patient, but also detects timing associated with such posture state, such as the time of day, the day of the week, or a specific time of day associated with a specific day. In this way, the posture-responsive therapy delivered by the IMD may be dependent not only on the posture state of the patient, but also on the timing associated with the detected posture state.

The posture state may be determined by pre-defined posture states, which may quantify patient posture or a combination of patient posture and activity. In accordance with the timing aspects of this disclosure, the same posture state may result in delivery of different types of therapy to the patient if the same posture state occurs at different times of the day. The IMD may store data that maps posture state and timing to specific therapy parameters or therapy parameter adjustments to facilitate automated therapy responsiveness by the IMD based on both the posture state of the patient and the timing of the posture state.

In one example, this disclosure describes a method comprising detecting a posture state of a patient via a medical device, detecting timing associated with the detected posture state, selecting therapy parameters for the medical device based on both the detected posture state and the timing associated with the detected posture state, and delivering therapy to the patient via the medical device according to the selected therapy parameters.

In another example, this disclosure describes a medical device system comprising a therapy delivery unit configured to deliver therapy to a patient, a posture state module configured to detect a posture state of a patient, a timing unit configured to detect timing associated with the detected posture state, and a processor configured to select therapy parameters for a medical device based on both the detected posture state and the timing associated with the detected posture state, wherein the processor causes the therapy delivery unit to deliver therapy to the patient according to the selected therapy parameters.

In another example, this disclosure describes a system comprising means for detecting a posture state of a patient via a medical device, means for detecting timing associated with the detected posture state, means for selecting therapy parameters for the medical device based on both the detected posture state and the timing associated with the detected posture state, and means for delivering therapy to a patient via the implantable medical device according to the selected therapy parameters.

The techniques of this disclosure may be implemented by a medical device system via hardware, software, firmware, or any combination thereof. If implemented in software, this disclosure may be directed to a computer readable storage medium comprising instructions that when executed in a medical device system cause the medical device system to detect a posture state of a patient via a medical device of the medical device system, detect timing associated with the detected posture state, select therapy parameters for the medical device based on both the detected posture state and the timing associated with the detected posture state, and deliver therapy to a patient via the medical device according to the selected therapy parameters.

The details of one or more examples of systems, devices, and techniques are set forth in the accompanying drawings and the description below. Other features, objects, and advantages of the disclosure will be apparent from the description and drawings, and from the claims.

DETAILED DESCRIPTION

Figure 1A:
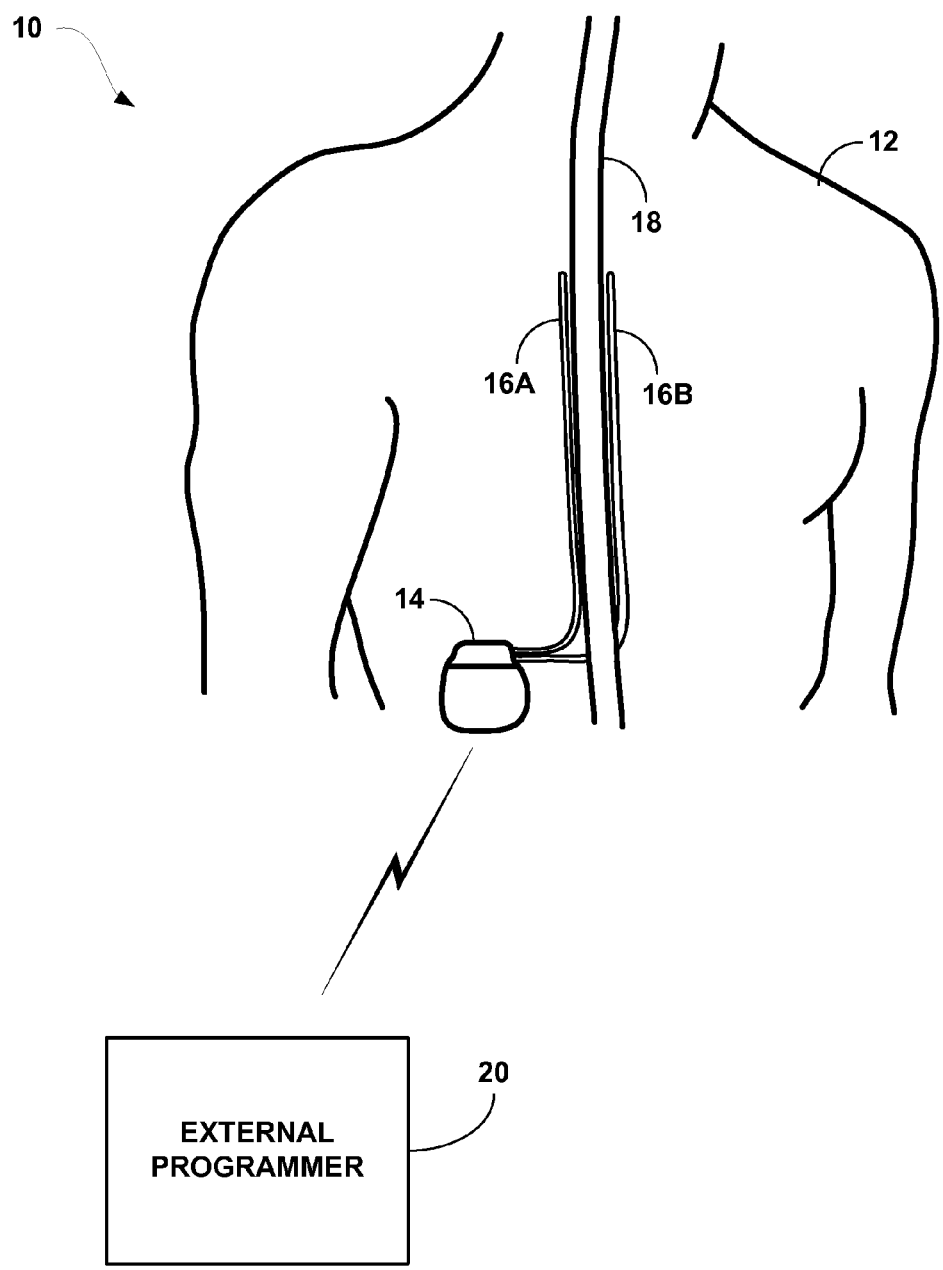
FIG. 1A is a conceptual diagram illustrating an example implantable stimulation system including two implantable stimulation leads.

In some medical devices that deliver electrical stimulation therapy or other therapies, therapeutic efficacy may change as the patient changes posture states. In this disclosure, the posture of a patient may be quantified by posture states, which may refer specifically to a patient posture or a combination of posture and activity of the patient. For example, some posture states, such as upright, may be sub-categorized as upright and active or upright and inactive. Other posture states, such as lying down posture states, may or may not have an activity component. Efficacy may refer, in general, to a combination of complete or partial alleviation of symptoms alone, or in combination with a degree of undesirable side effects.

Changes in posture state may cause changes in efficacy due to changes in distances between electrodes or other therapy delivery elements, e.g., due to temporary migration of leads or catheters caused by forces or stresses associated with different postures, or from changes in compression of patient tissue in different posture states. Also, posture state changes may present changes in symptoms or symptom levels, e.g., pain level. To maintain therapeutic efficacy, it may be desirable to adjust therapy parameters based on different postures and/or activities engaged by the patient. A therapy system may adjust therapy by modifying values for one or more therapy parameters, e.g., by specifying adjustments to a specific therapy parameter or by selecting different therapy programs or groups of programs that define different sets of therapy parameter values.

A change in efficacy due to changes in posture state may require the patient to continually manage therapy by manually adjusting certain therapy parameters, such as amplitude, pulse rate, or pulse width, or selecting different therapy programs to achieve more efficacious therapy throughout many different posture states. In some cases, a medical device employs a posture state detector that detects the patient posture state. The medical device adjusts therapy parameters in response to different posture states, which are determined with the posture state detector. Therapy adjustments in response to different posture states may be fully automatic, semi-automatic in the sense that a user may provide approval of proposed changes, or user-directed in the sense that the patient may manually adjust therapy based on the posture state indication.

In accordance with this disclosure, an implantable medical device system may be configured to detect a posture state of a patient, and detect a timing associated with the posture state. The implantable medical device system may also be configured to deliver posture-responsive therapy based on the detected posture state and the timing associated with the detected posture state. In particular, the implantable medical device system not only detects the posture state of a patient, but also detects timing associated with the posture state, such as the time of day, the day of the week, or a specific time of day associated with a specific day. In this way, the posture-responsive therapy delivered by the implantable medical device system may be dependent not only on the posture state of the patient, but also on the timing associated with the posture state. The same posture state, therefore, may result in delivery of different therapy to the patient if the same posture state occurs at different times of the day. An implantable medical device may store data, e.g., a lookup table, that maps posture states and timings to a specific therapy or therapy parameters. A detected posture state may correspond to one of a plurality of pre-defined posture states, or a detected posture state may refer to a posture state transition from one posture state to another posture state. In some examples, patient programming adjustments to the implantable medical device may be used to facilitate automated therapy response by the implantable medical device based on both the posture state of the patient and the timing of the posture state.

The posture and timing-responsive therapy techniques described in this disclosure are generally described in terms of application to electrical stimulation therapies for purposes of illustration. However, such techniques may be applied to other types of therapies, such as therapeutic fluid delivery. Therapy parameter values associated with electrical stimulation may include voltage or current amplitude, electrode configuration, and frequency. In the case of electrical stimulation pulses, therapy parameter values may include voltage or current pulse amplitude, pulse rate, pulse width and electrode configuration. Electrode configuration generally refers to a combination of electrodes and electrode polarities used to deliver stimulation.

Stimulation therapy delivered to a patient may be modified for any of a variety of reasons. In some cases, symptoms such as pain intensity change based on the posture state of the patient. For example, a patient may experience a greater degree of pain while walking compared to standing, while standing compared to sitting, or while sitting compared to lying. In such cases, it may be desirable to adjust one or more therapy parameter values in order to maintain therapeutic efficacy across multiple posture states. If pain is more intense in a given posture state at a specific time of day (e.g., upright and active during the day), for example, stimulation amplitude may be increased to provide more effective pain relief. Posture state changes, in addition to presenting changes in symptoms, may cause implanted therapy elements such as leads and electrodes to migrate relative to one another or relative to a target tissue site. Moreover, such migration may be more prevalent during specific times of day and less prevalent at other times of day or week, even for the same posture. Also, migration may be more or less prevalent for different activities or activity levels, which may be correlated with different times of day or week.

For example, compression, expansion, or other changes to tissue may render therapy more or less intense due to lead or catheter migration. As an illustration, for spinal cord stimulation (SCS), when a patient transitions from an upright posture state to a lying posture state in which the patient is lying on his back, leads may be compressed inward toward the spinal cord, possibly resulting in an acute increase in stimulation intensity. Changes from upright to lying during the daytime may be more likely to cause lead migration than the same changes during the nighttime, e.g., due to a likelihood of more strenuous or aggressive posture changes during the day relative to the nighttime.

To maintain therapeutic efficacy, the stimulation therapy delivered to a patient may be posture-responsive in the sense that one or more therapy parameter values may be modified when a patient transitions between different posture states. For example, an implantable electrical stimulation system may be configured to detect a posture state of a patient and automatically modify stimulation therapy based on the detected posture state. Furthermore, in accordance with this disclosure, not only the posture state but also timing associated with the posture state may be used to define therapy. In this way, the same posture state (more specifically, the same detected posture state or the same detected posture state transition) may result in different therapy parameters or different therapy parameter adjustments at different timing intervals of a given day. Timing intervals may be defined for every day, for different days of the week, for special days (such as vacation days) relative to normal days (such as workdays), for weekdays and weekend days, or any other interval of time for which therapy parameter adjustments may be desirable for the same posture. Different timing intervals or the same timing intervals may be defined for a wide variety of different types of days, and the types of days may be defined by a patient or clinician. Posture states that occur during such time intervals of specific days may result in automatic therapy adjustments.

Also, this disclosure contemplates a user's ability to define postures states and different therapies for specific days. For example, the user may be able to define activity-specific postures at specific times of day, and therapies may be associated with such postures and times of day. A patient, for example, may have work posture states or activity-specific posture states (e.g., bowling posture states or quilting posture states) programmed into the IMD. Each patient-specific posture state at a particular timing may define different tolerances for the same vector, different vectors, and/or different hysteresis zones. In this case, enabling different posture states at different times of day may provide processing efficiency. For instance, posture state classification or selection may be conducted more quickly when different posture states define different tolerances because postures typically used at a given time of day may be identified more quickly. Processing efficiency and power conservation may also be promoted when different posture states and timings associated with the posture states define different tolerances for purposes of posture state detection.

As a result of the posture-responsive therapy delivery, the values of one or more stimulation parameters of a stimulation signal being delivered as part of a therapy may change over time, e.g., according to a patient's posture state sensed by an implantable stimulation system at specific times. As an example, a patient may experience relatively greater pain while walking compared to standing, and this pain may be more prevalent during the daytime when walking is common. In such cases, an IMD may be configured to automatically modify the stimulation therapy to a relatively higher stimulation intensity when it detects that the patient has transitioned from a standing posture state to a walking posture state during a daytime interval, e.g., by delivering therapy having a higher stimulation amplitude value when the patient is walking during the day compared to the stimulation amplitude value when the patient is standing during the day, to address the increased pain experienced by the patient. These same posture changes, however, may not result in stimulation amplitude adjustments at nighttime. Accordingly, the same posture states may result in different therapy parameters or settings by the implantable medical device if such postures states are associated with different times of the day, different days, different times of specific days, different times of different days, and so forth.

As another example, posture states associated with times of a work day may be used to categorize a particular type of behavior for which a particular type of therapy is desired. The same posture state on a non-work day, however, may not be indicative of that particular type of behavior for which that particular type of therapy is desired. Take, for example, a bank teller that moves from a stationary upright position to a moving upright position in the daytime afternoon. This posture state change may result in increased levels of pain to the patient specifically related to the patient being upright and stationary for a long period of time followed by upright movement. This same posture state transition on a weekend or vacation day, however, may be much less likely to cause pain, e.g., due to the fact that the patient may not be standing as a bank teller on weekend or vacation days. Accordingly, by associating therapy not only with posture states or posture state transition, but also with the timing (e.g., a time of day, a day of the week, a specific type of day, or a specific time of a specific day), automated therapy adjustments by the implantable medical device may be more accurately tied to the likely occurrence of pain.

As a further example, an IMD may be configured to automatically modify the stimulation therapy to a relatively lower stimulation intensity when the stimulation system detects that the patient has ceased walking and returned to a standing posture state at a specific time. In this manner, stimulation therapy delivered to a patient via an implantable medical device may be automatically modified to deliver stimulation appropriate to the posture state exhibited by a patient during a specifically defined time interval.

Therapy may be modified according to a modification profile. The profile of the modification may refer to any of a variety of characteristics of the modification, such as timing, slope, or the like. For some posture state transitions, for example, the modification profile may be characterized by a gradual slope in the therapy parameter value over an extended period of time. For other posture state transitions, the modification profile is characterized by an abrupt increase or decrease in a therapy parameter value. In this case, the therapy parameter value may be more immediately (e.g., instantaneously) modified, rather than gradually ramped upward or downward. Regardless of the manner of therapy modification, however, this disclosure recognizes that pain or other symptoms remedied by an implantable medical device are commonly associated not only with changes in posture state, but more specifically with changes in posture state at specific times of day. Accordingly, this disclosure provides for the association of therapy or therapy adjustments with both patient posture and the timing of such posture.

FIG. 1A is a schematic diagram illustrating an implantable medical device system 10 including a pair of implantable electrode arrays in the form of stimulation leads 16A and 16B. Although the techniques described in this disclosure are generally applicable to a variety of medical devices including external and implantable medical devices (IMDs), application of such techniques to IMDs and, more particularly, implantable electrical stimulators such as neurostimulators will be described for purposes of illustration. More particularly, the disclosure will refer to an implantable SCS system for purposes of illustration, but without limitation as to other types of medical devices including implantable fluid delivery devices such as implantable drug pumps.

As shown in FIG. 1A, system 10 includes an IMD 14 and external programmer 20 shown in conjunction with a patient 12, who is ordinarily a human patient. In the example of FIG. 1A, IMD 14 is an implantable electrical stimulator that delivers SCS, e.g., for relief of chronic pain or other symptoms. Again, although FIG. 1A shows an IMD, other examples may include an external stimulator, e.g., with percutaneously implanted leads. Stimulation energy is delivered from IMD 14 to spinal cord 18 of patient 12 via one or more electrodes of implantable leads 16A and 16B (collectively "leads 16"). In some applications, such as spinal cord stimulation (SCS) to treat chronic pain, the adjacent implantable leads 16 may have longitudinal axes that are substantially parallel to one another.

Although FIG. 1A is directed to SCS therapy, system 10 may alternatively be directed to any other condition that may benefit from stimulation therapy. For example, system 10 may be used to treat tremor, Parkinson's disease, epilepsy, urinary or fecal incontinence, sexual dysfunction, obesity, gastroparesis, or psychiatric disorders (e.g., depression, mania, obsessive compulsive disorder, anxiety disorders, and the like). In this manner, system 10 may be configured to provide therapy taking the form of deep brain stimulation (DBS), pelvic floor stimulation, gastric stimulation, or any other stimulation therapy. For any such therapy, the posture state of the patient and timing associated with the posture state may be used collectively to define therapy parameters to be applied by the implantable medical device.

Each of leads 16 illustrated in FIG. 1 may include electrodes (not shown in FIG. 1), and the parameters for a program that controls delivery of stimulation therapy by IMD 14 may include information identifying which electrodes have been selected for delivery of stimulation according to a stimulation program, the polarities of the selected electrodes, i.e., the electrode configuration for the program, and voltage or current amplitude, pulse rate, and pulse width of stimulation delivered by the electrodes. Delivery of stimulation pulses will be described for purposes of illustration. However, stimulation may be delivered in other forms, such as continuous waveforms. Programs that control delivery of other therapies by IMD 14 may include other parameters, e.g., such as dosage amount, rate, or the like for drug delivery.

In the example of FIG. 1A, leads 16 carry one or more electrodes that are placed adjacent to the target tissue of the spinal cord. One or more electrodes may be disposed at a distal tip of a lead 16 and/or at other positions at intermediate points along the lead. Electrodes of leads 16 transfer electrical stimulation generated by IMD 14 to tissue of patient 12. The electrodes may be electrode pads on a paddle lead, circular (e.g., ring) electrodes surrounding the body of leads 16, conformable electrodes, cuff electrodes, segmented electrodes, or any other type of electrodes capable of forming unipolar, bipolar or multipolar electrode configurations for therapy. In general, ring electrodes arranged at different axial positions at the distal ends of leads 16 will be described for purposes of illustration.

Leads 16 may be implanted within patient 12 and directly or indirectly (e.g., via a lead extension) coupled to IMD 14. Alternatively, as mentioned above, leads 16 may be implanted and coupled to an external stimulator, e.g., through a percutaneous port. In some cases, an external stimulator is a trial or screening stimulation that used on a temporary basis to evaluate potential efficacy to aid in consideration of chronic implantation for a patient. In additional examples, IMD 14 may be a leadless stimulator with one or more arrays of electrodes arranged on a housing of the stimulator rather than leads that extend from the housing.

IMD 14 delivers electrical stimulation therapy to patient 12 via selected combinations of electrodes carried by one or both of leads 16. The target tissue for the electrical stimulation therapy may be any tissue affected by electrical stimulation energy, which may be in the form of electrical stimulation pulses or waveforms. In some examples, the target tissue includes nerves, smooth muscle, and skeletal muscle. In the example illustrated by FIG. 1A, the target tissue is tissue proximate spinal cord 18, such as within an intrathecal space or epidural space of spinal cord 18, or, in some examples, adjacent nerves that branch off of spinal cord 18. Leads 16 may be introduced into spinal cord 18 via any suitable region, such as the thoracic, cervical or lumbar regions. Stimulation of spinal cord 18 may, for example, prevent pain signals from traveling through the spinal cord and to the brain of the patient. Patient 12 may perceive the interruption of pain signals as a reduction in pain and, therefore, efficacious therapy results.

The deployment of electrodes via leads 16 is described for purposes of illustration, but arrays of electrodes may be deployed in different ways. For example, a housing associated with a leadless stimulator may carry arrays of electrodes, e.g., rows and/or columns (or other patterns). Such electrodes may be arranged as surface electrodes, ring electrodes, or protrusions. As a further alternative, electrode arrays may be formed by rows and/or columns of electrodes on one or more paddle leads. In some examples, electrode arrays may include electrode segments, which may be arranged at respective positions around a periphery of a lead, e.g., arranged in the form of one or more segmented rings around a circumference of a cylindrical lead.

In the example of FIG. 1A, stimulation energy is delivered by IMD 14 to the spinal cord 18 to reduce the amount of pain perceived by patient 12. As described above, IMD 14 may be used with a variety of different therapies, such as peripheral nerve stimulation (PNS), peripheral nerve field stimulation (PNFS), DBS, cortical stimulation (CS), pelvic floor stimulation, gastric stimulation, and the like. The electrical stimulation delivered by IMD 14 may take the form of electrical stimulation pulses or continuous stimulation waveforms, and may be characterized by controlled voltage levels or controlled current levels, as well as pulse width and pulse rate in the case of stimulation pulses.

In some examples, IMD 14 generates and delivers stimulation therapy according to one or more programs. A program defines values for one or more parameters that define an aspect of the therapy delivered by IMD 14 according to that program. For example, a program that controls delivery of stimulation by IMD 14 in the form of pulses may define a voltage or current pulse amplitude, a pulse width, a pulse rate, for stimulation pulses delivered by IMD 14 according to that program. Moreover, therapy may be delivered according to multiple programs, wherein multiple programs are contained within each of a plurality of groups.

Each program group may support an alternative therapy selectable by patient 12, and IMD 14 may deliver therapy according to the multiple programs. IMD 14 may rotate through the multiple programs of the group when delivering stimulation such that numerous conditions of patient 12 are treated. As an illustration, in some cases, stimulation pulses formulated according to parameters defined by different programs may be delivered on a time-interleaved basis. For example, a group may include a program directed to leg pain, a program directed to lower back pain, and a program directed to abdomen pain. In this manner, IMD 14 may treat different symptoms substantially simultaneously.

During use of IMD 14 to treat patient 12, movement of patient 12 among different posture states may affect the ability of IMD 14 to deliver consistent efficacious therapy. For example, posture state changes may present changes in symptoms or symptom levels, e.g., pain level. As another example, a patient posture state may affect the relative location between the electrodes of leads 16 and a target therapy site. For example, leads 16 may migrate toward IMD 14 when patient 12 bends at the waist, resulting in displacement of electrodes relative to the target stimulation site and possible disruption in delivery of effective therapy. Stimulation energy transferred to target tissue may be reduced due to electrode migration, which may reduce therapeutic efficacy in terms of relief of symptoms (e.g., pain) or an increase in undesirable side effects. Furthermore, in accordance with this disclosure, IMD 14 is configured with therapy programs that operate not only on the basis of patient posture, but also on the timing associated with such posture. Accordingly, the same posture state or posture state transition of patient 12 may result in the execution of different therapy programs or application of adjustments to parameter values associated with such therapy programs depending on the time of day that such posture states or posture state transitions are detected.

A change from a lying down posture state to an upright and moving state at nighttime may result in a slight upward adjustment in stimulation intensity, but may be otherwise very similar to a set of sleeptime stimulation parameters. In this case, the posture change may be the likely result of the patient leaving bed to use the bathroom or to retrieve a glass of water. The same change from a lying down state to an upright and moving state in the daytime, however, may result in a different type of therapy protocol change. In this case, the posture change may be more likely a transition into a more aggressive activity, during the day, and therefore, the therapy parameters may change to result in a more aggressive therapy protocol at this time of day even though the change in posture is similar to that mentioned above during nighttime.

As an example of how posture state may affect the relative location between the electrodes of leads 16 and a target therapy site, leads 16 may be compressed towards spinal cord 18 when patient 12 lies down. Such compression may cause an increase in the amount of stimulation energy transferred to the target tissue. An increase in stimulation energy transferred to the target stimulation site may cause unusual sensations or an otherwise undesirable intensity of therapy, which may both be considered undesirable side effects that undermine overall efficacy. Thus, in some examples, the amplitude of stimulation therapy may need to be decreased when patient 12 is lying down to avoid causing patient 12 additional pain or unusual sensations resulting from the increased compression near electrodes of leads 16. The additional pain or unusual sensations may be considered undesirable side effects that undermine overall efficacy.

IMD 14 includes a posture state module that detects the patient posture state. In addition, IMD 14 may include a timing unit (such as a clock or counter) that is used to monitor the timing associated with any given posture state or posture state transition. IMD 14 automatically adjusts stimulation according to the detected posture state and the associated timing. The patient posture and activity level can, but need not include an activity component. Example posture states may include "Upright," "Upright and Active," "Lying Down," and so forth.

IMD 14 includes a posture responsive therapy mode that, when activated, results in adjustment of one or more stimulation parameter values based on a detected posture state and the timing associated with the detected posture state. The posture responsive therapy may help mitigate changes in the efficacy of therapy attributable to patient posture changes, and may differ depending on the timing. The posture state module may include one or more accelerometers that detect when patient 12 occupies a posture state for which it is appropriate to decrease the stimulation amplitude, e.g., when patient 12 lies down. IMD 14 may automatically reduce stimulation amplitude upon detecting patient 12 is lying down at a specific time of the day, thereby eliminating the need for patient 12 to manually adjust the therapy, which may be cumbersome. In addition, automatic adjustment of stimulation parameters based on a detected patient posture and timing may also provide more responsive therapy because IMD 14 may detect a change in patient posture and modify therapy parameters faster than patient 12 may be able to manually modify the therapy parameter values.

Many other examples of reduced efficacy due to increase coupling or decreased coupling of stimulation energy to target tissue may occur due to changes in posture and/or activity level associated with patient posture state. Moreover, the efficacy may be tied not only to changes in posture and/or activity level, but also to the timing associated with such changes. Therefore, to avoid or reduce possible disruptions in effective therapy due to posture state changes at specific times of day, IMD 14 includes a posture state module that detects the posture state of patient 12 and a timing unit that monitors the timing associated with the posture state. There could be different levels of fatigue or inflammation common at different times of the day for a particular posture, or on different days altogether, such that pain levels are predictably different at such times for the particular posture.

A processor within IMD 14 (or possibly within the programmer) may cause automatic adjustments to stimulation according to the detected posture state and timing. For example, a posture state module may include a posture state sensor such as an accelerometer that detects when patient 12 lies down, stands up, or otherwise changes posture, and a timing unit (such as a clock or counter) may continuously monitor the timing of such posture changes.

In response to a posture state indication by the posture state module at specific times of day, IMD 14 may change program group, program, stimulation amplitude, pulse width, pulse rate, and/or one or more other parameters, groups or programs to maintain therapeutic efficacy. When a patient lies down, for example, IMD 14 may automatically reduce stimulation amplitude so that patient 12 does not need to reduce stimulation amplitude manually. Moreover, in accordance with this disclosure, changes from standing to lying down may result in different types of therapy adjustments if such changes occur at different times, e.g., at different times of day, at the same time of different days, and so forth.

In some cases, IMD 14 may communicate with external programmer 20 to present a proposed change in stimulation in response to a posture state change, and receive approval or rejection of the change from a user, such as patient 12 or a clinician, before automatically applying the therapy change. In this case, IMD 14 may record and associate the therapy change not only with the posture state transition, but more specifically with the posture state transition at the time that the user-approved therapy change occurred. Then, when that same timing and posture is encountered, e.g., in a subsequent day, the same therapy change may be executed automatically by IMD 14. In some examples, posture state detection may also be used to provide notifications to a patient or care giver, such as providing notification via a wireless link to the care giver that a patient has potentially experienced a fall at a particular time. Also, posture state and timing may be categorized into patient-defined activities, e.g., "bowling night" that occurs periodically, e.g., once per week. Such patient-defined activities may have posture and timing responsive therapy at the patient-defined times, and IMD 14 may allow for simple schedule changes by the patient to auto-program a "bowling night" therapy into a different night.

Referring still to FIG. 1A, a user, such as a clinician or patient 12, may interact with a user interface of external programmer 20 to program IMD 14. Programming of IMD 14 may refer generally to the generation and transfer of commands, programs, or other information to control the operation of IMD 14. For example, external programmer 20 may transmit programs, parameter adjustments, program selections, group selections, or other information to control the operation of IMD 14, e.g., by wireless telemetry. As one example, external programmer 20 may transmit parameter adjustments to support therapy modifications relating to changes in the posture state of patient 12 at particular times of day. As another example, a user may select programs or program groups, and such selections may be associated with the time of day and the posture state when such selections occurred. Again, a program may be characterized by an electrode combination, electrode polarities, voltage or current amplitude, pulse width, pulse rate, and/or duration. A group may be characterized by multiple programs that are delivered simultaneously or on an interleaved or rotating basis.

In some cases, external programmer 20 may be characterized as a physician or clinician programmer if it is primarily intended for use by a physician or clinician. In other cases, external programmer 20 may be characterized as a patient programmer if it is primarily intended for use by a patient. A patient programmer is generally accessible to patient 12 and, in many cases, may be a portable device that may accompany the patient throughout the patient's daily routine. In general, a physician or clinician programmer may support selection and generation of programs by a clinician for use by IMD 14, whereas a patient programmer may support adjustment and selection of such programs by a patient during ordinary use.

In some aspects of this disclosure, an external programmer 20 may facilitate automatic learning of posture and timing-responsive therapy by IMD 14. If a user adjusts a given therapy at a given time of the day for a given posture, via external programmer 20, IMD 14 (or programmer 20) may be configured to store the configuration defined by the adjustment. Then, in a subsequent day, at the same given time if the same given posture is detected, IMD 14 may automatically adjust to the configuration that was selected by the user on the previous day. In this way, posture and time-responsive therapy by IMD 14 specifically programmed by a user may be automatically programmed into IMD 14 to occur in a periodic manner in subsequent days, assuming that the same the timing and posture is detected on the subsequent days. Posture changes that occur at different times of such subsequent days, in this case, may not result in any automatic therapy adjustments in IMD 14. Similarly, if the given time is detected in subsequent days, but the posture change is not detected, automatic therapy adjustments in IMD 14 may not occur. Patient-programmed therapy may be stored for particular posture states and timings, and may be assigned names associated with the activity to which the therapy is directed (e.g., bowling night therapy). A user may be able to select an assigned therapy name to provide that same therapy, possibly even during an atypical time.

IMD 14 may be constructed with a biocompatible housing, such as titanium or stainless steel, or a polymeric material such as silicone or polyurethane, and surgically implanted at a site in patient 12, e.g., near the pelvis. IMD 14 may also be implanted in patient 12 at other locations, preferably in locations that would be minimally noticeable to patient 12. Alternatively, IMD 14 may be external with percutaneously implanted leads. For SCS, IMD 14 may be located in the lower abdomen, lower back, upper buttocks, or other location to secure IMD 14. Leads 16 may be tunneled from IMD 14 through tissue to reach the target tissue adjacent to spinal cord 18 for stimulation delivery.

Figure 1B:
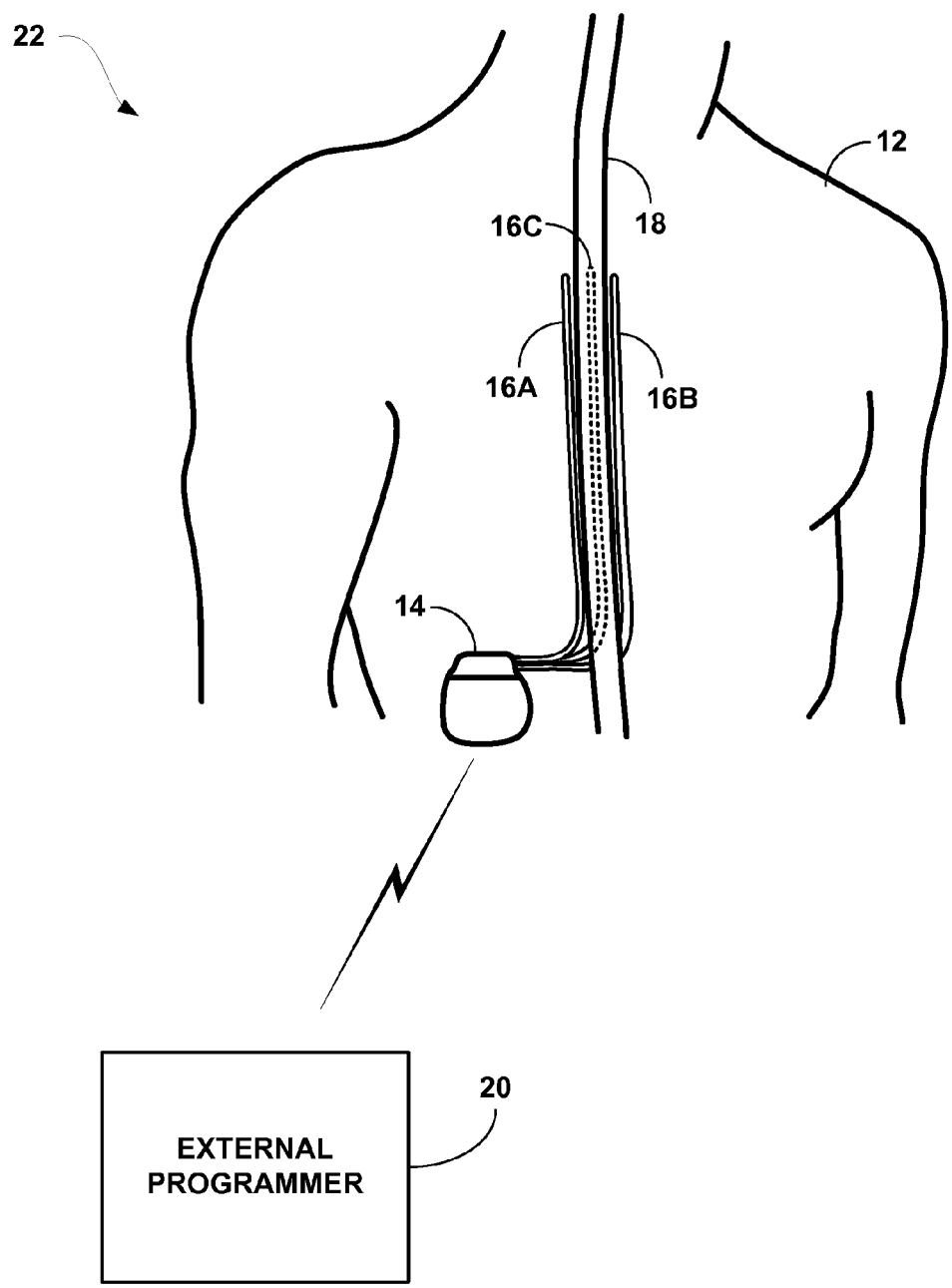
FIG. 1B is a conceptual diagram illustrating an example implantable stimulation system including three implantable stimulation leads.

FIG. 1B is a conceptual diagram illustrating an implantable medical device system 22 including three implantable stimulation leads 16A, 16B, 16C (collectively leads 16). System 22 generally conforms to system 10 of FIG. 1A, but includes a third lead. Accordingly, IMD 14 may deliver stimulation via combinations of electrodes carried by all three leads 16, or a subset of the three leads. The third lead, e.g., lead 16C, may include a greater number of electrodes than leads 16A and 16B and be positioned between leads 16A and 16B or on one side of either lead 16A or 16B. The number and configuration of leads 16 may be stored within external programmer 20 to allow programmer 20 to appropriately program stimulation therapy or assist in the programming of stimulation therapy.

In some examples, leads 16A and 16B each include four electrodes, while lead 16C includes eight or sixteen electrodes, thereby forming a so-called 4-8-4 or 4-16-4 lead configuration. Other lead configurations, such as 8-16-8, 8-4-8, 16-8-16, 16-4-16, are possible, whereby the number in the configuration indication refers to the number of electrodes in a particular electrode column, which may be defined by a lead 16A-16C. In some cases, electrodes on lead 16C may be smaller in size and/or closer together than the electrodes of leads 16A or 16B. Movement of lead 16C due to changing activities or postures of patient 12 may, in some instances, more severely affect stimulation efficacy than movement of leads 16A or 16B. Patient 12 may further benefit from the ability of IMD 14 to detect posture states, timings of detected posture states, and associated changes, and automatically adjust stimulation therapy to maintain therapy efficacy in a three lead system 22.

Figure 1C:
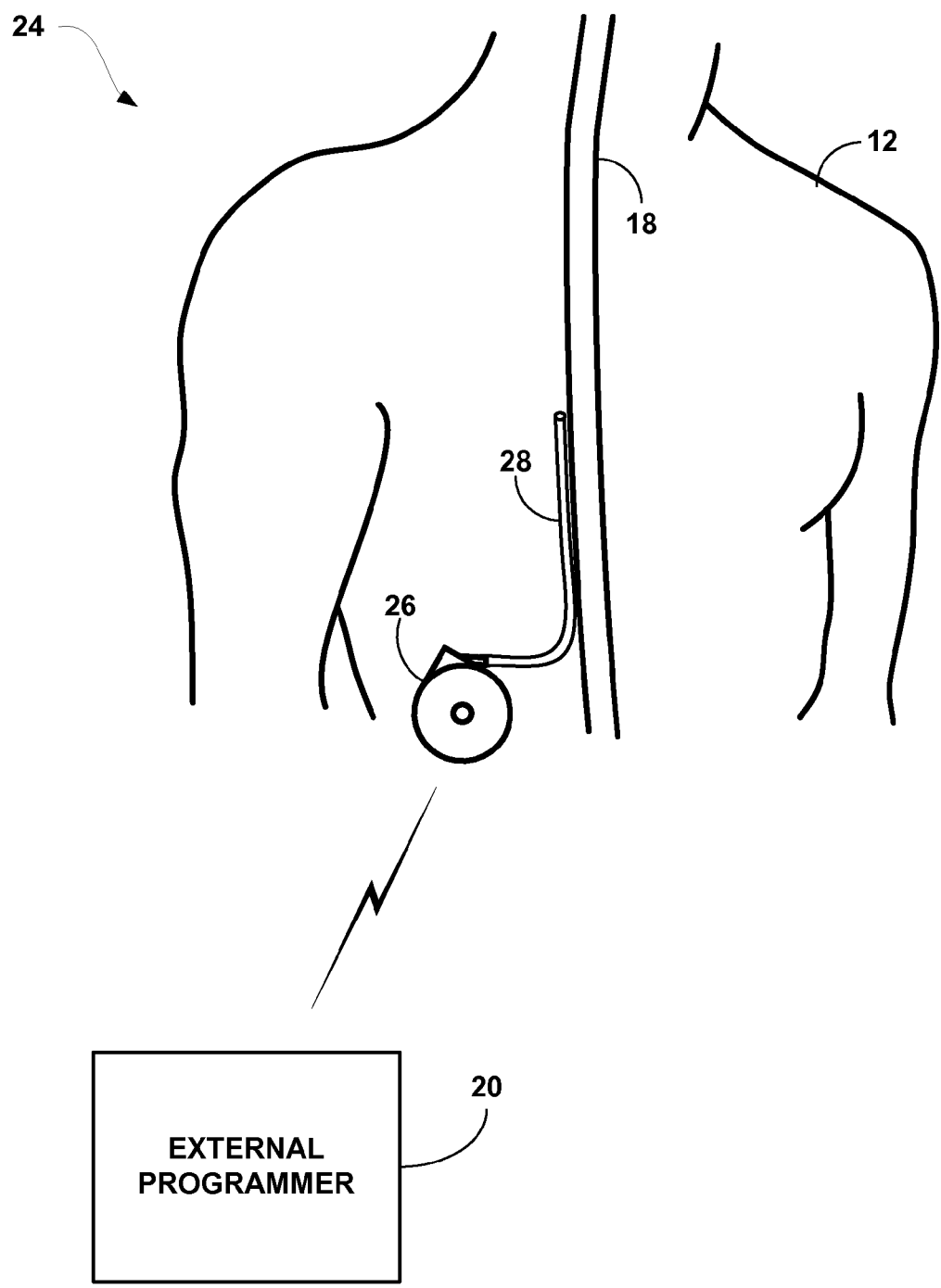
FIG. 1C is a conceptual diagram illustrating an example implantable drug delivery system including a delivery catheter.

FIG. 1C is a conceptual diagram illustrating an implantable medical device system 24 including one delivery catheter 28 coupled to IMD 26. As shown in the example of FIG. 1C, system 24 is substantially similar to systems 10 and 22. However, system 24 is a drug delivery system that performs the therapy functions via delivery of one or more therapeutic agents instead of electrical stimulation therapy. IMD 26 functions as a drug pump in the example of FIG. 1C, and IMD 26 communicates with external programmer 20 to initialize therapy or modify therapy during operation. In addition, IMD 26 may be refillable to allow chronic drug delivery.

A fluid delivery port of catheter 28 may be positioned within an intrathecal space or epidural space of spinal cord 18, or, in some examples, adjacent nerves that branch off of spinal cord 18. Although IMD 26 is shown as coupled to only one catheter 28 positioned along spinal cord 18, additional catheters may also be coupled to IMD 26. Multiple catheters may deliver drugs or other therapeutic agents to the same anatomical location or the same tissue or organ. Alternatively, each catheter may deliver therapy to different tissues within patient 12 for the purpose of treating multiple symptoms or conditions. In some examples, IMD 26 may be an external device that includes a percutaneous catheter that delivers a therapeutic agent to patient 12, e.g., in the same manner as catheter 28. Alternatively, the percutaneous catheter can be coupled to catheter 28, e.g., via a fluid coupler. In other examples, IMD 26 may include both electrical stimulation capabilities as described in IMD 14 (FIG. 1A) and drug delivery therapy.

IMD 26 may also operate using parameters that define the method of drug delivery. IMD 26 may include programs, or groups of programs, that define different delivery methods for patient 12. For example, a program that controls delivery of a drug or other therapeutic agent may include a titration rate or information controlling the timing of bolus deliveries. Patient 12 may use external programmer 20 to adjust the programs or groups of programs to regulate the therapy delivery.

Similar to IMD 14, IMD 26 includes a posture state module that monitors the posture state of patient 12 and adjusts therapy accordingly. In addition, IMD 26 includes a timing unit, such as a clock or counter that monitors the timing associated with any posture state so that both timing and posture states may define therapy to be delivered. For example, the posture state module may indicate that patient 12 transitions from a lying down posture state to a standing up posture state, and the timing unit may determine the timing associated with this posture state transition. IMD 26 may automatically increase the rate of drug delivered to patient 12 in the standing position if patient 12 has indicated that pain increased when standing at a particular time of the day. This automated adjustment to therapy based upon posture state and timing may be activated for all or only a portion of the programs used by IMD 26 to deliver therapy.

Similar to the examples described with respect to adjustment of one or more electrical stimulation parameters to modify electrical stimulation therapy during a transition period, based on patient's 12 detected posture state and timing, one or more parameters associated with the drug delivery therapy provided by IMD 26 may be modified with different modification profiles.

As an example, the rate of drug delivery to patient 12 may be increased to a desirable rate from a lesser rate based on a detected patient transition from a lying down posture state to a standing up posture state in the middle of the night. Daytime transitions from lying down to standing up, however, may not result in such changes, or may result in different types of therapy changes. In any case, IMD 26 (or the programmer) considers not only the posture state of patient 22, but also the timing associated with the posture state in making automated therapy adjustments. In detecting posture states, this disclosure contemplates detecting a posture state from a plurality of pre-defined posture states, or detecting a posture state transition. Posture states may be defined based on posture alone, or based on posture and activity. For example, a first posture state and a second posture state may define different postures, or a first posture state and a second posture state may define the same postures with different types of activity (e.g., upright and moving versus upright and stationary)

In the example of FIG. 1C, the drug delivery rate may be adjusted to the desired level by ramping up the rate of drug delivery at a constant rate of change. Such adjustments to the drug delivery rate parameter may be automatically made by IMD 26 to modify the drug delivery therapy provided to patient 12 based on the posture state detected by IMD 26 at a given time. In some cases, IMD 26 may store two or more different drugs, and may administer different drugs based on posture state and timing. Different dosages of one or more drugs may also be administered to patient 22 based on detected posture state and the timing of the detected posture state.

The techniques described herein for modifying therapy delivery by IMD 14 (FIG. 1A), which provides electrical stimulation therapy, may also be implemented to modify therapy delivery by IMD 26 selected based on a type of detected patient posture transition and the timing associated therewith. In some cases, a posture state transition may cause therapy adjustments at one time of the day, but the same posture state transition may not cause any therapy adjustments at another time of the day. For example, a change from a lying down posture state to an upright and moving posture state may not cause a therapy change at nighttime, but this same change from the lying down posture state to the upright and moving posture state may cause a change to more aggressive therapy in the daytime. Changes in therapy may be defined by an absolute set of therapy parameters for a given posture state (or transition between two or more posture states) and timing, or may be defined by one or more adjustments to current therapy parameters for a given posture state (or transition between two or more posture states) and timing.

Figure 2:
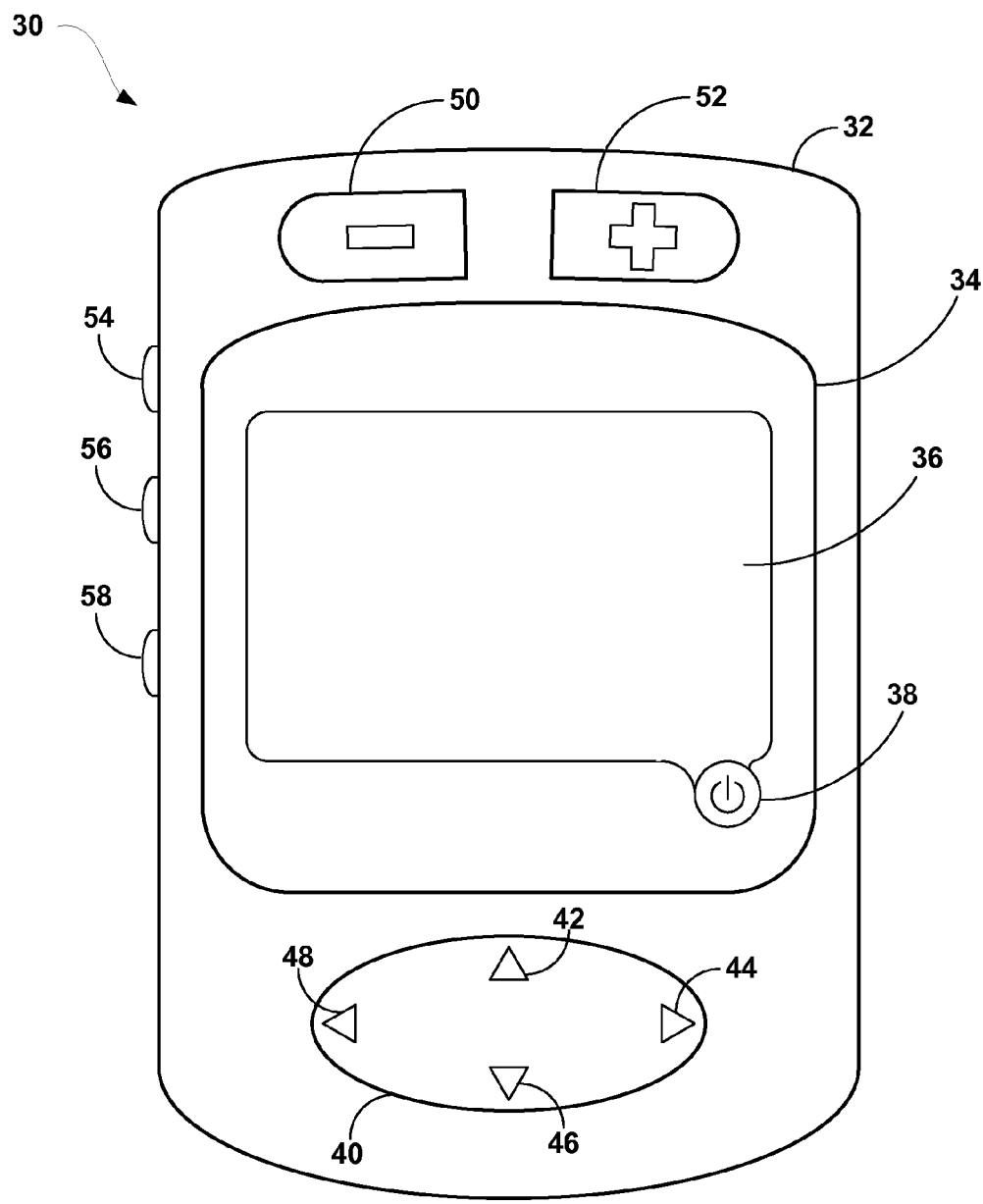
FIG. 2 is a conceptual diagram illustrating an example patient programmer for programming stimulation therapy delivered by an implantable medical device.

FIG. 2 is a conceptual diagram illustrating an example patient programmer 30 for programming stimulation therapy delivered by an IMD. Patient programmer 30 is an example of external programmer 20 illustrated in FIGS. 1A, 1B and 1C and may be used with either IMD 14 or IMD 26. In alternative examples, patient programmer 30 may be used with an external medical device. As shown in FIG. 2, patient programmer 30 provides a user interface (not shown) for a user, such as patient 12, to manage and program stimulation therapy. Patient programmer 30 is protected by housing 32, which encloses circuitry necessary for patient programmer 30 to operate.

Patient programmer 30 also includes display 36, power button 38, increase button 52, decrease button 50, sync button 58, stimulation ON button 54, and stimulation OFF button 56. Cover 34 protects display 36 from being damaged during use of patient programmer 30. Patient programmer 30 also includes control pad 40 which allows a user to navigate through items displayed on display 36 in the direction of arrows 42, 44, 46, and 48. In some examples, the buttons and pad 40 may take the form of soft keys (e.g., with functions and contexts indicated on display 36), with functionality that may change, for example, based on current programming operation or user preference. In alternative examples, display 36 is a touch screen with which patient 12 may directly interact without the use of control pad 40. A touch screen display may eliminate the use of buttons, such as increase button 52 and decrease button 50, although buttons may be used in addition to a touch screen display.

In the illustrated example, patient programmer 30 is a hand held device. Patient programmer 30 may accompany patient 12 throughout a daily routine. In some cases, patient programmer 30 may be used by a clinician when patient 12 visits the clinician in a hospital or clinic. In other examples, patient programmer 30 may be a clinician programmer that remains with the clinician or in the clinic and is used by the clinician and/or patient 12 when the patient is in the clinic. In the case of a clinician programmer, small size and portability may be less important. Accordingly, a clinician programmer may be sized larger than a patient programmer, and it may provide a larger screen for more full-featured programming.

Housing 32 may be constructed of a polymer, metal alloy, composite, or combination material suitable to protect and contain components of patient programmer 30. In addition, housing 32 may be partially or completely sealed such that fluids, gases, or other elements may not penetrate the housing and affect components therein. Power button 38 may turn patient programmer 30 ON or OFF as desired by patient 12. Patient 12 may control the illumination level, or backlight level, of display 36 by using control pad 40 to navigate through the user interface and increase or decrease the illumination level with decrease and increase buttons 50 and 52.

In some examples, illumination may be controlled by a knob that rotates clockwise and counter-clockwise to control patient programmer 30 operational status and display 36 illumination. Patient programmer 30 may be prevented from turning OFF during telemetry with IMD 14 or another device to prevent the loss of transmitted data or the stalling of normal operation. Alternatively, patient programmer 30 and IMD 14 may include instructions that handle possible unplanned telemetry interruption, such as battery failure or inadvertent device shutdown.

Display 36 may include any one or more of a liquid crystal display (LCD), dot matrix display, organic light-emitting diode (OLED) display, touch screen, or similar monochrome or color display capable of providing visible information to patient 12. Display 36 may provide a user interface regarding current stimulation therapy, posture state information, provide a user interface for receiving feedback or medication input from patient 12, display an active group of stimulation programs, and display operational status of patient programmer 30 or IMDs 14 or 26. For example, patient programmer 30 may provide a scrollable list of groups, and a scrollable list of programs within each group, via display 36. In addition, display may present a visible posture state indication.

Patient 12 or another user may interact with control pad 40 to navigate through items displayed on display 36. Patient 12 may press control pad 40 on any of arrows 42, 44, 46, and 48 in order to move between items presented on display 36 or move to another screen not currently shown on the display. In some examples, pressing the middle of control pad 40 selects any items highlighted in display 36. In other examples, scroll bars, a scroll wheel, individual buttons, or a joystick may perform the complete or partial functions of control pad 40. In alternative examples, control pad 40 may be a touch pad that allows patient 12 to move a cursor within the user interface displayed on display 36 to manage therapy.

Decrease button 50 and increase button 52 provide an input mechanism for patient 12. In general, activation of decrease button 50 (e.g., by pressing button 50) decreases the value of a highlighted stimulation parameter every time the decrease button is pressed. In contrast, activation of increase button 52 increases the value of a highlighted stimulation parameter one step every time the increase button is pressed. While buttons 50 and 52 may be used to control the value of any stimulation parameter, buttons 50 and 52 may also control patient feedback input. When either button 50 or 52 is selected, patient programmer 30 may initialize communication with IMD 14 or 26 to change therapy accordingly.

When depressed by patient 12, stimulation ON button 54 directs programmer 30 to generate a command for communication to IMD 14, where the command instructs IMD 14 to turn on stimulation therapy. Stimulation OFF button 56 turns off stimulation therapy when depressed by patient 12. Sync button 58 forces patient programmer 30 to communicate with IMD 14. When patient 12 enters an automatic posture response screen of the user interface, pressing sync button 58 turns on the automatic posture response to allow IMD 14 to automatically change therapy according to the posture state of patient 12 at various times of the day. Pressing sync button 58 again, when the automatic posture response screen is displayed, turns off the automatic posture response. Different automatic posture responses may be stored in patient programmer for different posture states (or the same posture states) at different times of the day. In the example of FIG. 2, patient 12 may use control pad 40 to adjust the volume, contrast, illumination, time, and measurement units of patient programmer 30.

If the patient changes therapy for a particular posture state at a particular time of day, patient programmer 30 may provide the user with an option of storing this setting for similar postures at the same time of day (e.g., by presenting this option to the user via a user interface of a patient programmer). The time of day may be categorized by a time slot, e.g., in hourly increments or other defined increments or blocks of time, which may be defined by a physician. The time increments may vary over the course of a day, or vary in different types of days. If the user causes programmer 30 to store this setting (or the setting is stored automatically), programmer 30 may automatically program IMD 14 to similar settings upon IMD 14 detecting the same patient posture and time slot in a subsequent day. In accordance with this disclosure, the ability to automate therapy based on posture state and timing may occur solely in IMD 14, may occur in IMD 14 in response to an initial programming of therapy by programmer 30, may occur in IMD 14 in response to automated time-controlled programming sessions initiated by programmer 30, or may occur in IMD in response to therapy adjustments by the user via programmer 30.

In some examples, buttons 54 and 56 may be configured to perform operational functions related to stimulation therapy or the use of patient programmer 30. For example, buttons 54 and 56 may control the volume of audible sounds produced by programmer 20, wherein button 54 increases the volume and button 56 decreases the volume. Button 58 may be pressed to enter an operational menu that allows patient 12 to configure the user interface of patient programmer 30 to the desires of patient 12. For example, patient 12 may be able to select a language, backlight delay time, display brightness and contrast, or other similar options. In alternative examples, buttons 50 and 52 may control all operational and selection functions, such as those related to audio volume or stimulation therapy.

Patient programmer 30 may take other shapes or sizes not described herein. For example, patient programmer 30 may take the form of a clam-shell shape, similar to some cellular phone designs. When patient programmer 30 is closed, some or all elements of the user interface may be protected within the programmer. When patient programmer 30 is opened, one side of the programmer may contain a display while the other side may contain input mechanisms. In any shape, patient programmer 30 may be capable of performing the requirements described herein. Alternative examples of patient programmer 30 may include other input mechanisms such as a keypad, microphone, camera lens, or any other media input that allows the user to interact with the user interface provided by patient programmer 30.

In alternative examples, the buttons of patient programmer 30 may perform different functions than the functions provided in FIG. 2 and/or may have a different arrangement. In addition, other examples of patient programmer 30 may include different button layouts or different numbers of buttons. For example, patient programmer 30 may even include a single touch screen that incorporates all user interface functionality with a limited set of buttons or no other buttons.

Figure 3:
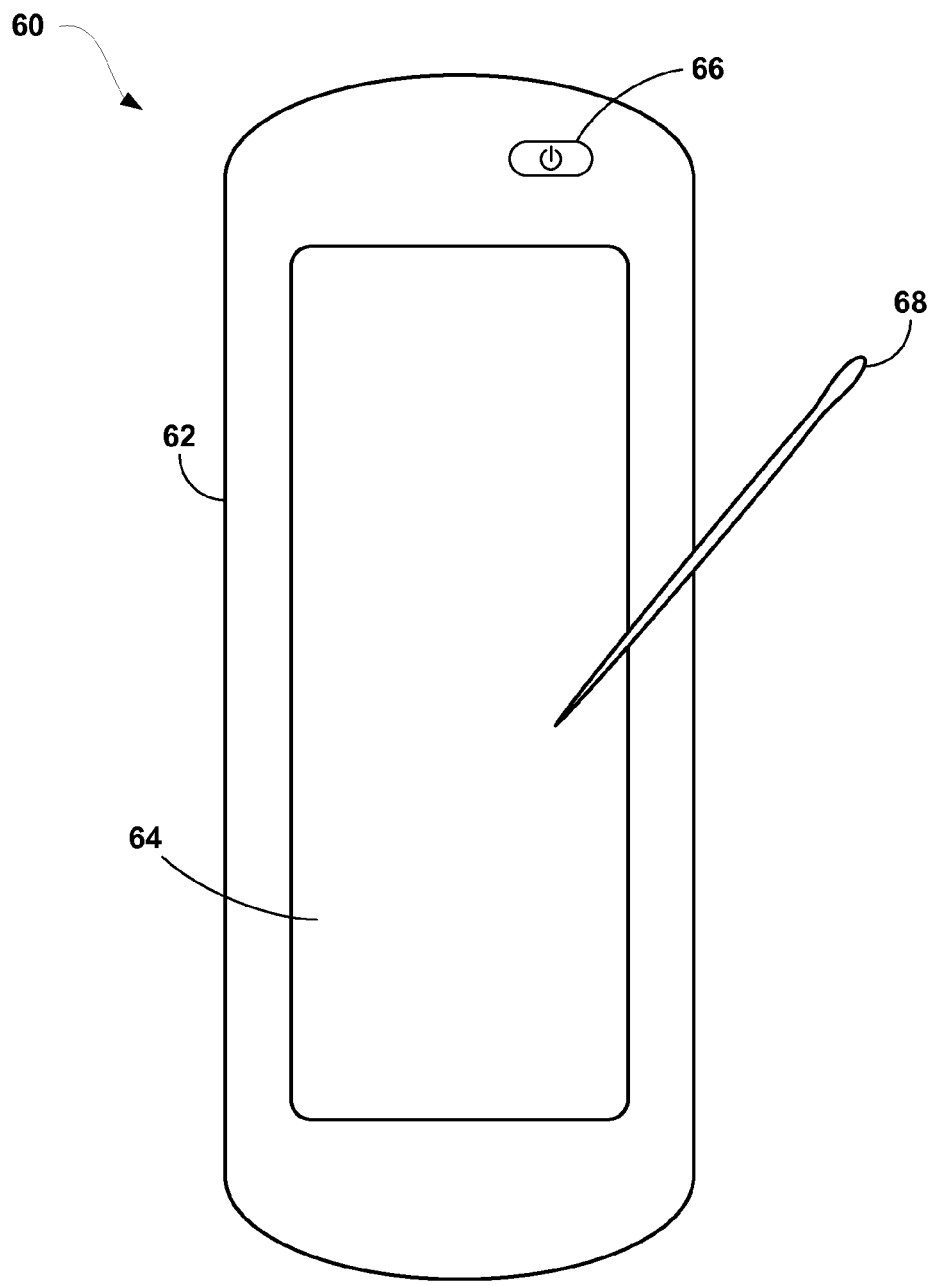
FIG. 3 is a conceptual diagram illustrating an example clinician programmer for programming stimulation therapy delivered by an implantable medical device.

FIG. 3 is a conceptual diagram illustrating an example clinician programmer 60 for programming stimulation therapy delivered by an IMD. Clinician programmer 60 is an example of external programmer 20 illustrated in FIGS. 1A, 1B and 1C and may be used with either IMD 14 or IMD 26. In alternative examples, clinician programmer 60 may be used with an external medical device. As shown in FIG. 3, clinician programmer 60 provides a user interface (not shown) for a user, such as a clinician, physician, technician, or nurse, to manage and program stimulation therapy. Clinician programmer 60 is protected by housing 62, which encloses circuitry necessary for clinician programmer 60 to operate.

Clinician programmer 60 includes display 64 and power button 66. In the example of FIG. 3, display 64 is a touch screen that accepts user input via touching certain areas within display 64. The user may use stylus 68 to touch display 64 and select virtual buttons, sliders, keypads, dials, or other such representations presented by the user interface shown by display 64. In some examples, the user may be able to touch display 64 with a finger, pen, or any other pointing device. In alternative examples, clinician programmer 60 may include one or more buttons, keypads, control pads, touch pads, or other devices that accept user input, similar to patient programmer 30.

In the illustrated example, clinician programmer 60 is a hand held device. Clinician programmer 60 may be used within the clinic or on in-house patient calls. Clinician programmer 60 may be used to communicate with multiple IMDs 14 and 26 within different patients. In this manner, clinician programmer 60 may be capable of communicating with many different devices and retain patient data separate for other patient data. In some examples, clinician programmer 60 may be a larger device that may be less portable, such as a notebook computer, workstation, or even a remote computer that communicates with IMD 14 or 26 via a remote telemetry device.

Most, if not all, of clinician programmer 60 functions may be completed via the touch screen of display 64. The user may program stimulation therapy (e.g., selecting stimulation parameter values), modify programs or groups, retrieve stored therapy data, retrieve posture state information from an IMD or another device, define posture states and other activity information, change the contrast and backlighting of display 64, or any other therapy related function. In addition, clinician programmer 60 may be capable of communicating with a networked server in order to send or receive an email or other message, retrieve programming instructions, access a help guide, send an error message, or perform any other function that may be beneficial to prompt therapy. In accordance with this disclosure, clinician programmer 60 may store different stimulation programs or different sets of therapy parameters to be applied at different times of the day (or times of specific days of the week) based on posture at a given time of the day. The techniques of this disclosure, which concern therapy delivery based on both posture state and timing associated with the posture state, may occur solely in IMD 14, or may occur in IMD 14 in response to programming of therapy by programmer 60. Programmer 60 may store several protocols, programs or sets of therapy parameters that define different therapy, and may associate the different protocols, programs or sets of therapy parameters with different posture states and times of day. Programmer 60 may upload the protocols, programs or sets of therapy parameters to IMD 14 so that IMD will perform the desired therapy deliver for a given posture state and timing of the given posture state.

Also, this disclosure contemplates a user's ability to define postures states and different therapies for specific days. For example, the user may be able to define activity-specific postures at specific times of day, and therapies may be associated with such posture states and times of day. A patient or physician, for example, may define work posture states or activity-specific posture states (e.g., bowling posture states or quilting posture states), and these posture states may be programmed into the IMD.

Housing 62 may be constructed of a polymer, metal alloy, composite, or combination material suitable to protect and contain components of clinician programmer 60. In addition, housing 62 may be partially or completely sealed such that fluids, gases, or other elements may not penetrate the housing and affect components therein. Power button 66 may turn clinician programmer 60 ON or OFF as desired by the user. Clinician programmer 60 may require a password, biometric input, or other security measure to be entered and accepted before the user can use clinician programmer 60.

Clinician programmer 60 may take other shapes or sizes not described herein. For example, clinician programmer 60 may take the form of a clam-shell shape, similar to some cellular phone designs. When clinician programmer 60 is closed, at least a portion of display 64 is protected within housing 62. When clinician programmer 60 is opened, one side of the programmer may contain a display while the other side may contain input mechanisms. In any shape, clinician programmer 60 may be capable of performing the requirements described herein.

Figure 4:
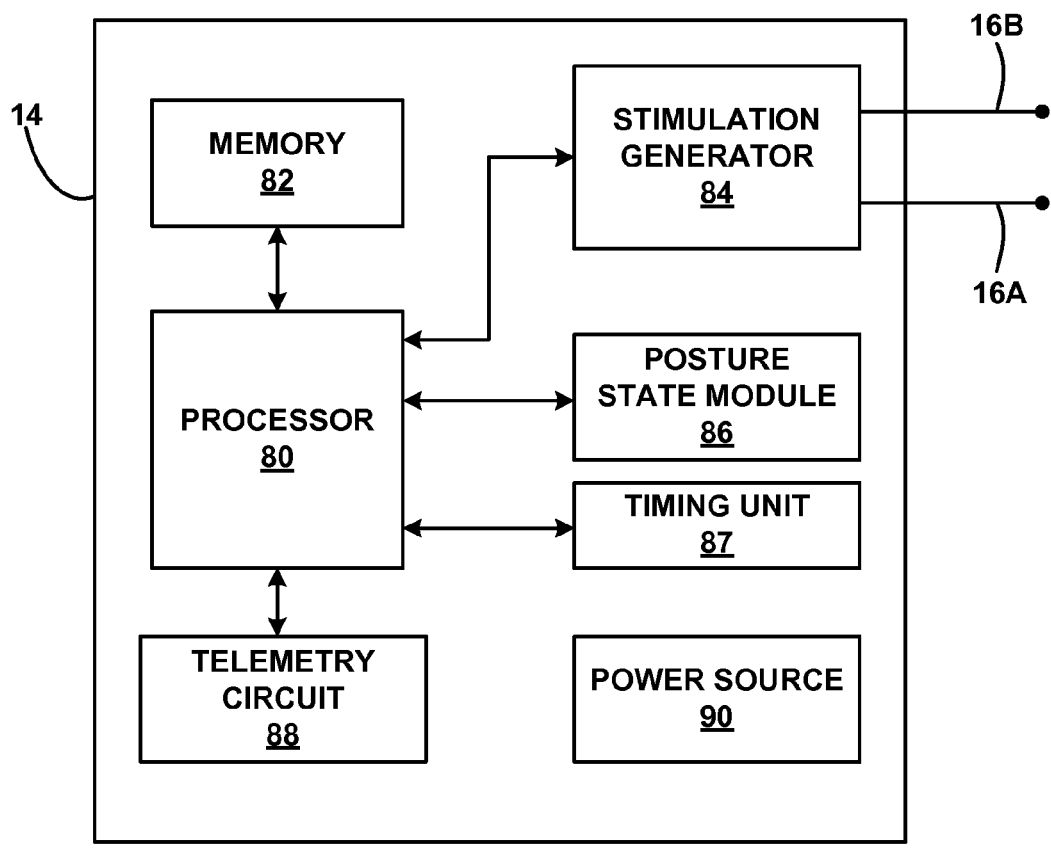
FIG. 4 is a functional block diagram illustrating various components of an example implantable electrical stimulator consistent with this disclosure.

FIG. 4 is a functional block diagram illustrating various components of an IMD 14. In the example of FIG. 4, IMD 14 includes a processor 80, memory 82, stimulation generator 84, posture state module 86, timing unit 87, telemetry circuit 88, and power source 90. The stimulation generator 84 forms a therapy delivery module.

Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media. Memory 82 may store instructions for execution by processor 80, stimulation therapy data, posture state information (e.g., posture state definitions, information associating posture states with therapy programs at specific times of the day or days of the week, and the like), posture state indications, and any other information regarding therapy or patient 12. Therapy information may be recorded for long-term storage and retrieval by a user, and the therapy information may include any data created by or stored in IMD 14. Memory 82 may include separate memories for storing instructions, posture state information, program histories, and any other data that may benefit from separate physical memory modules.

As one example, memory 82 may store a lookup table (LUT) or other data structure that associates posture states (e.g., posture states or posture state transitions) and specific times of the day with specific stimulation parameter protocols. For example, posture states and time slots for times of day may be indices to the LUT such that, given a posture state and time slot, processor 80 may locate an associated set of therapy parameters. The same posture state may map to different sets of therapy parameters at different times of day within LUT. Also, different posture states and timings may be defined for different days of the week, or for different types of days (e.g., weekend days, vacation days or sick days relative to normal work days). By providing this type of flexibility in the programming of IMD 14, IMD 14 may be more responsive to a specific routine of the patient. Accordingly, therapy may be improved by facilitating posture and timing-responsive therapy by IMD 14.

The techniques of this disclosure may also be extended for other types of therapy delivery features, such as disable cycling (e.g., cycling between an "on" period of therapy delivery and an "off" period without therapy delivery), pulse rate adjustment, and/or pulse width adjustments. The phrase "therapy delivery parameters" is mean to cover any of these types of therapy features, including a disable cycling feature, in addition to the various other types of therapy parameters discussed herein.

Processor 80 controls stimulation generator 84 to deliver electrical stimulation via electrode combinations formed by electrodes in one or more electrode arrays. For example, stimulation generator 84 may deliver electrical stimulation therapy via electrodes on one or more leads 16, e.g., as stimulation pulses or continuous waveforms. Components described as processors within IMD 14, external programmer 20 or any other device described in this disclosure may each comprise one or more processors, such as one or more microprocessors, digital signal processors (DSPs), application specific integrated circuits (ASICs), field programmable gate arrays (FPGAs), programmable logic circuitry, or the like, either alone or in any suitable combination. The functions attributed to processors described herein may be embodied as software, firmware, hardware, or any combination thereof.

Stimulation generator 84 may include stimulation generation circuitry to generate stimulation pulses or continuous waveforms and, in some examples, switching circuitry to switch the stimulation across different electrode combinations, e.g., in response to control by processor 80. In particular, processor 80 may control the switching circuitry on a selective basis to cause stimulation generator 84 to deliver electrical stimulation to selected electrode combinations and to shift the electrical stimulation to different electrode combinations in a first direction or a second direction when the therapy must be delivered to a different location within patient 12. Different electrode combinations, different stimulation settings, or other parameter settings may be defined based on posture and timing associated with the posture. In some examples, stimulation generator 84 may include multiple current sources to drive more than one electrode combination at one time. In this case, stimulation generator 84 may decrease current to the first electrode combination and simultaneously increase current to the second electrode combination to shift the stimulation therapy, e.g., in response to a change in posture, a change in time, or a change in both posture and timing. Ultimately, the therapy may be defined based not on posture state alone, not on timing alone, but on both the posture state and the timing associated with the posture state.

An electrode configuration, e.g., electrode combination and associated electrode polarities, may be represented by a data stored in a memory location, e.g., in memory 82, of IMD 14. Processor 80 may access the memory location to determine the electrode combination for a detected posture and timing of the detected posture state, and may control stimulation generator 84 to deliver electrical stimulation via the indicated electrode combination. To adjust electrode combinations, amplitudes, pulse rates, or pulse widths, processor 80 may command stimulation generator 84 to make the appropriate changes to therapy according to instructions within memory 82 and rewrite the memory location to indicate the changed therapy. Any such change in electrode combinations, amplitudes, pulse rates, or pulse widths may be responsive to a change in posture-timing inputs to a lookup table stored in memory 82. The lookup table, as mentioned above, may map posture state and time slots to sets of therapy parameters, settings or therapy protocol. Other types of data structures (e.g., other than a lookup table) could also be used to map posture state and time slots to sets of therapy parameters.

In other examples, rather than rewriting a single memory location, processor 80 may make use of two or more memory locations. As previously mentioned, in some example, the instructions stored in memory 82 may allow processor 80 to control stimulation generator 84 to make parameter adjustments at specific times when specific postures are detected during such specific times. Again, the specific times may correspond to specific times of a day, times of a particular day (e.g., specific times of a weekday or a weekend day), specific days of the week, specific days of the month, days defined or selected by the patient (e.g., vacation days, travel days, sick days, special days), and so forth. Special days may be defined for specific patients, e.g., bowling night, quilting night, and so forth, to define activities that the particular patient engages on such days. A particular posture state at 8:00 PM on bowling night may result in different therapy parameters for the IMD than that same posture state at 8:00 PM on quilting night, and vice versa. Therapy during patient-specific activities may be defined based on posture and timing, and the patient may be able to select a specific activity in order to cause therapy associated with that activity. The IMD may automatically default to the therapy of any patient-specific activity when timing and posture state correspond to a pre-defined time slot and posture state for the activity When activating stimulation, processor 80 may access not only the memory location specifying the electrode combination but also other memory locations specifying various stimulation parameters such as voltage or current amplitude, pulse width and pulse rate. Stimulation generator 84, e.g., under control of processor 80, then makes use of the electrode combination and parameters in formulating and delivering the electrical stimulation to patient 12.

According to examples described herein, such stimulation parameters may be adjusted upon detecting a posture state transition that corresponds to a specific pre-defined time slot. In some examples, processor 80 may detect a posture state of patient 12 via posture state module 86 that indicates that a modification of the stimulation therapy is appropriate, e.g., according to instructions stored in memory 82. Processor 80 may access instructions for modifying the stimulation therapy based on the patient 12 posture state, e.g., by changing from a stimulation program appropriate for the previous posture state at the current time of day to a stimulation program appropriate for patient's current posture state at the current time of day.

Depending on the parameter values defined by the respective program, an adjustment may be made to one or more or the parameter values as a result of a detected change in patient posture at a particular time. Processor 80 may also access for execution of the parameter adjustment over a transition period, e.g., by ramping the parameter from the existing value to the desired value of the new program according to a specific rate of change. Based on those instructions, processor 80 may control the stimulation parameter adjustment by sending an appropriate command to stimulation generator 84, which receives the command and ramps the respective stimulation parameter according to specified rate of change, thereby modifying the stimulation therapy being delivered to patient 12 based on the detected posture state of patient 12 at a given time. Time of day, day of the week, or any other timing parameter may be monitored by timing unit 87. Processor 80 may access timing unit 87 anytime that posture state module 86 detects a posture state transition so that processor 80 may associate the posture state transition with the correct time of day. The posture state transition and the time of day, then, may be used by processor 80 as indices of a lookup table stored in memory 82, wherein the lookup table maps posture state transitions and time slots of the day to specific therapies or therapy adjustments. The timing unit (as with the processor that performs the therapy parameter selections) may be alternatively located in a programmer. Also, a programmer could include a precise clock that periodically synchronizes a rough clock in the implantable medical device.

An exemplary range of electrical stimulation parameters likely to be effective in treating chronic pain, e.g., when applied to spinal cord 18, are listed below. While stimulation pulses are described, stimulation signals may be of any of a variety of forms such as sine waves or the like.

1. Pulse Rate: between approximately 0.5 Hz and approximately 1200 Hz, more preferably between approximately 5 Hz and approximately 250 Hz, and still more preferably between approximately 30 Hz and approximately 130 Hz.

2. Amplitude: between approximately 0.1 volts and approximately 50 volts, more preferably between approximately 0.5 volts and approximately 20 volts, and still more preferably between approximately 1 volt and approximately 10 volts. In other examples, a current amplitude may be defined as the biological load in the voltage that is delivered. For example, the range of current amplitude may be between approximately 0.1 milliamps (mA) and approximately 50 mA.

3. Pulse Width: between approximately 10 microseconds and approximately 5000 microseconds, more preferably between approximately 100 microseconds and approximately 1000 microseconds, and still more preferably between approximately 180 microseconds and approximately 450 microseconds.

In other applications, different ranges of parameter values may be used. For DBS, as one example, alleviation or reduction of symptoms associated with Parkinson's disease, essential tremor, epilepsy, psychiatric disorders or other disorders may make use of stimulation having a pulse rate in the range of approximately 0.5 to approximately 1200 Hz, such as between approximately 5 to approximately 250 Hz, or between approximately 30 to approximately 185 Hz, and a pulse width in the range of approximately 10 microseconds and 5000 microseconds, such as between approximately 60 microseconds and approximately 1000 microseconds, or between approximately 60 microseconds and approximately 450 microseconds, or between approximately 60 microseconds and approximately 150 microseconds. Amplitude ranges such as those described above with reference to SCS, or other amplitude ranges, may be used for different DBS applications.

Processor 80 accesses stimulation parameters in memory 82, e.g., as programs and groups of programs defined for particular posture states at specific times. Upon selection of a particular program group, processor 80 may control stimulation generator 84 to generate and deliver stimulation according to the programs in the groups, e.g., simultaneously or on a time-interleaved basis. A group may include a single program or multiple programs. As mentioned previously, each program may specify a set of stimulation parameters, such as amplitude, pulse width and pulse rate. In addition, each program may specify a particular electrode combination for delivery of stimulation. Again, the electrode combination may specify particular electrodes in a single array or multiple arrays, e.g., on a single lead or among multiple leads. Processor 80 also may control telemetry circuit 88 to send and receive information to and from external programmer 20. For example, telemetry circuit 88 may send information to and receive information from patient programmer 30.

Posture state module 86 allows IMD 14 to sense the patient posture state, e.g., posture, activity or any other static position or motion of patient 12. In the example of FIG. 4, posture state module 86 includes one or more accelerometers, such as three-axis accelerometers, capable of detecting static orientation or vectors in three-dimensions. Example accelerometers include a micro-electro-mechanical accelerometer. In other examples, posture state module 86 may alternatively or additionally include one or more gyroscopes, piezoelectric crystals, pressure transducers or other sensors to sense the posture state of patient 12. Posture state information generated by posture state module 86 and processor 80 may correspond to an activity and/or posture undertaken by patient 12 or a gross level of physical activity, e.g., activity counts based on footfalls or the like.

Posture state information from posture state module 86 may be stored in memory 82 for later review by a clinician, used to adjust therapy, present a posture state indication to patient 12 (e.g., via patient programmer 30), or some combination thereof. As an example, processor 80 may record the posture state parameter value, or output, of the 3-axis accelerometer and assign the posture state parameter value to a certain predefined posture indicated by the posture state parameter value. In this manner, IMD 14 may be able to track how often patient 12 remains within a certain posture. IMD 14 may also store which group or program was being used to deliver therapy when patient 12 was in the sensed posture. Further, processor 80 may also adjust therapy for a new posture when posture state module 86 indicates that patient 12 has in fact changed postures. Therefore, IMD 14 may be configured to provide posture responsive stimulation therapy to patient 12. Stimulation adjustments in response to posture state may be automatic or semi-automatic (subject to patient approval). In many cases, fully automatic adjustments may be desirable so that IMD 14 may react more quickly to posture state changes.

A posture state parameter value from posture state module 86 that indicates the posture state may constantly vary throughout the day of patient 12. However, a certain activity (e.g., walking, running, or biking) or a posture (e.g., standing, sitting, or lying down) may include multiple posture state parameter values from posture state module 86. Memory 82 may include definitions for each posture state of patient 12 and may associate posture states at specific times of day (or other times) with particular stimulation parameter values, particular stimulation protocols, or other settings or configurations. A timing unit 87 (such as a clock or counter) may provide timing information to processor 80 associated with any posture or posture transition detected by posture state module 86. In this way, processor may associate posture states at specific times of day (or other times) with particular stimulation parameter protocols, settings or configurations, and may store the posture state, the timing, and the stimulation parameter protocols, settings or configurations associated with that posture state and timing in memory 82. The next time that the same posture state is encountered at that same timing (e.g., at a similar time of the day), then automatic switching to an associated stimulation parameter values, settings or configurations by stimulation generator 84 may occur at the direction of processor 80.

In one example, the definition of each posture state may be illustrated as a cone in three-dimensional space. Whenever the posture state parameter value, e.g., a vector, from the three-axis accelerometer of posture state module 86 resides within a predefined cone, processor 80 indicates that patient 12 is in the posture state of the cone. In other examples, posture state parameter value from the 3-axis accelerometer may be compared to a look-up table or equation to determine the posture state in which patient 12 currently resides.

Posture responsive stimulation may allow IMD 14 to implement a certain level of automation in therapy adjustments. Automatically adjusting stimulation may free patient 12 from the constant task of manually adjusting therapy each time patient 12 changes posture or starts and stops a certain posture state. Such manual adjustment of stimulation parameters can be tedious, requiring patient 12 to, for example, depress one or more keys of patient programmer 30 multiple times during the patient posture state to maintain adequate symptom control. In some examples, patient 12 may eventually be able to enjoy posture state responsive stimulation therapy without the need to continue making changes for different postures via patient programmer 30. Instead, patient 12 may transition immediately or over time to fully automatic adjustments based on posture state. Moreover, the adjustments for any posture state may differ, depending on the time of day, the day of the week, or other specific timing parameter consistent with this disclosure. In this way, IMD 14 may provide posture and timing-responsive therapy that is specifically defined and adapted to the daily/weekly routine of the patient. The patient may also be able to override the normal settings of a given day to provide secondary settings for that day, e.g., changing the protocol of a workday to that of a vacation day. Vacation days, holidays or weekend days, for example, may have different therapy for a given posture and timing than would be defined for work days. Patent-specific days or activities may also be defined for automatic execution at the corresponding time, and such patent-specific days or activities may also be selectable by the patient at any time.

Although posture state module 86 is described as containing the 3-axis accelerometer, posture state module 86 may contain multiple single-axis accelerometers, dual-axis accelerometers, 3-axis accelerometers, or some combination thereof. In some examples, an accelerometer or other sensor may be located within or on IMD 14, on one of leads 16 (e.g., at the distal tip or at an intermediate position), an additional sensor lead positioned somewhere within patient 12, within an independent implantable sensor, or even worn on patient 12. For example, one or more microsensors may be implanted within patient 12 to communicate posture state information wirelessly to IMD 14. In this manner, the posture state of patient 12 may be determined from multiple posture state sensors placed at various locations on or within the body of patient 12.

In other examples, posture state module 86 may additionally or alternatively be configured to sense one or more physiological parameters of patient 12. For example, physiological parameters may include heart rate, electromyography (EMG), an electroencephalogram (EEG), an electrocardiogram (ECG), temperature, respiration rate, or pH. These physiological parameters may be used by processor 80, in some examples, to confirm or reject changes in sensed posture state that may result from vibration, patient travel (e.g., in an aircraft, car or train), or some other false positive of posture state.

In some examples, processor 80 processes the analog output of the posture state sensor in posture state module 86 to determine activity and/or posture data. For example, where the posture state sensor comprises an accelerometer, processor 80 or a processor of posture state module 86 may process the raw signals provided by the posture state sensor to determine activity counts. In some examples, processor 80 may process the signals provided by the posture state sensor to determine velocity of motion information along each axis.

In one example, each of the x, y, and z signals provided by posture state module 86 may have both DC components and AC components. The DC components describe the gravitational force exerted upon the sensor and can thereby be used to determine orientation of the sensor within the gravitational field of the earth. Assuming the orientation of the sensor is relatively fixed with respect to the patient, the DC components of the x, y and z signals may be utilized to determine the patient's orientation within the gravitational field, and hence to determine the posture of the patient.

The AC components of the x, y and z signals yields information about patient motion. In particular, the AC components of a signal may be used to derive a value for an activity describing the patient's motion. This activity may involve a level, direction of motion, or acceleration of the patient.

One method for determining the patient activity is by determining an activity count. An activity count may be used to indicate the activity or activity level of patient 12. For example, a signal processor may sum the magnitudes of the AC portion of an accelerometer signal for N consecutive samples. For instance, assuming sampling occurs as 25 Hz, N may be set to 25, so that count logic provides the sum of the samples that are obtained in one second. This sum may be referred to as an "activity count". The number "N" of consecutive samples may be selected by the processor based on the current posture state at a given time, if desired. The activity count may be the activity portion of the activity parameter value that is added to the posture portion. The resulting activity parameter value may then incorporate activity, posture and timing of the activity and posture to generate an accurate indication of the motion of patient 12 at a specific time of the day or at a specific time on a specific day.

As another example, the activity parameter value may be defined describing direction of motion. This activity parameter value may be associated with a vector and an associated tolerance, which may be a distance from the vector. Another example of an activity parameter value relates to acceleration. The value quantifying a level of change of motion over time in a particular direction may be associated with this parameter referenced in the activity parameter value.

IMD 14 wirelessly communicates with external programmer 20, e.g., patient programmer 30 or clinician programmer 60, or another device by radio frequency (RF) communication or proximal inductive interaction of IMD 14 with external programmer 20. Telemetry circuit 88 may send information to and receive information from external programmer 20 on a continuous basis, at periodic intervals, at non-periodic intervals, or upon request from the stimulator or programmer. To support RF communication, telemetry circuit 88 may include appropriate electronic components, such as amplifiers, filters, mixers, encoders, decoders, and the like.

Power source 90 delivers operating power to the components of IMD 14. Power source 90 may include a small rechargeable or non-rechargeable battery and a power generation circuit to produce the operating power. Recharging may be accomplished through proximal inductive interaction between an external charger and an inductive charging coil within IMD 14. In some examples, power requirements may be small enough to allow IMD 14 to utilize patient motion and implement a kinetic energy-scavenging device to trickle charge a rechargeable battery. In other examples, traditional batteries may be used for a limited period of time. As a further alternative, an external inductive power supply could transcutaneously power IMD 14 when needed or desired.

Figure 5:
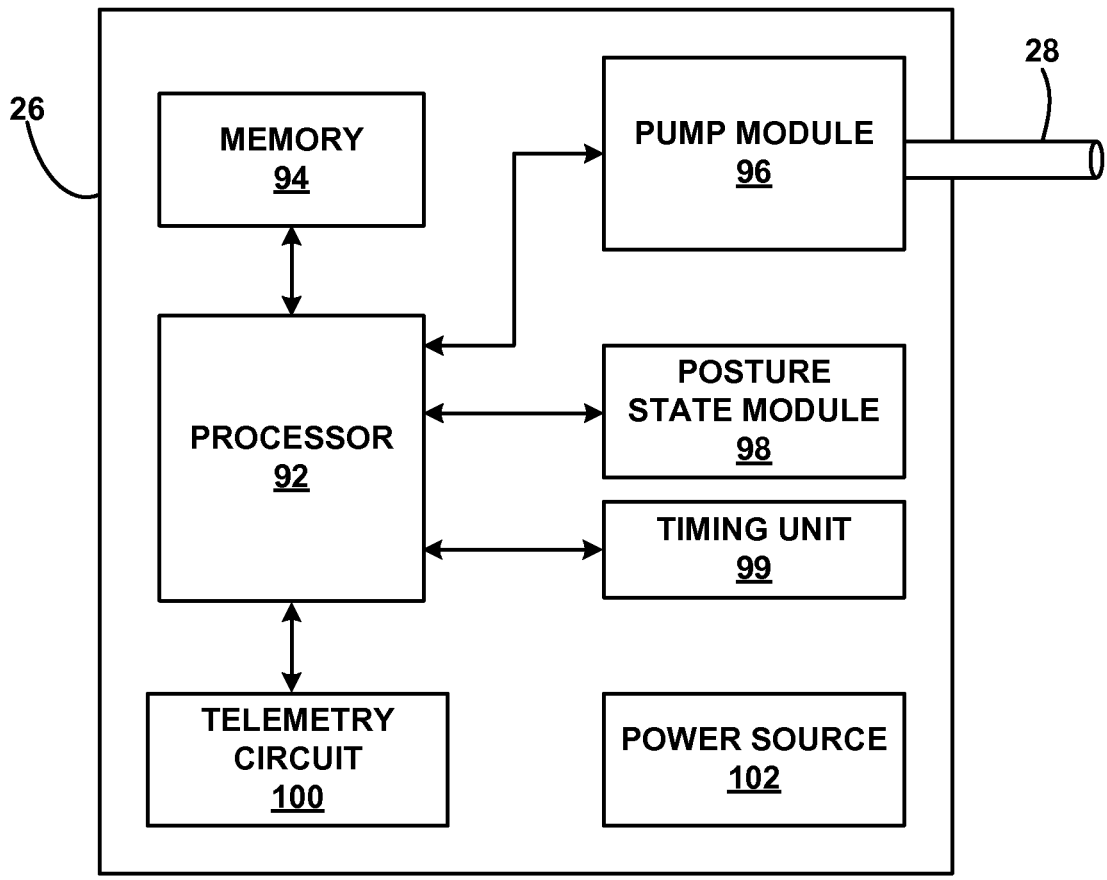
FIG. 5 is a functional block diagram illustrating various components of an example implantable drug pump consistent with this disclosure.

FIG. 5 is a functional block diagram illustrating various components of an IMD 26, which delivers a therapeutic agent to patient 12. IMD 26 is a drug pump that operates substantially similar to IMD 14 of FIG. 4, but delivers a therapeutic agent instead of electrical stimulation. IMD 26 includes processor 92, memory 94, pump module 96, posture state module 98, timing unit 99, telemetry circuit 100, and power source 102. Instead of stimulation generator 84 of IMD 14, IMD 26 includes pump module 96 for delivering drugs or some other therapeutic agent via catheter 28. Pump module 96 may include a reservoir to hold the drug and a pump mechanism to force drug out of catheter 28 and into patient 12.

Processor 92 controls pump module 96 according to therapy instructions stored within memory 94. For example, memory 94 may contain the programs or groups of programs that define the drug delivery therapy for patient 12. A program may indicate the bolus size or flow rate of the drug, and processor 92 may accordingly deliver therapy. Processor 92 may also use posture state information from posture state 98 to adjust drug delivery therapy when patient 12 changes posture states, e.g., adjusts his or her posture or activity. Furthermore, the posture states may be associated with times of day or other times recorded by timing unit 99. In this way, the bolus size or flow rate of a drug, or the type of drug administered may be based on posture and timing associated with that posture.

Figure 6:
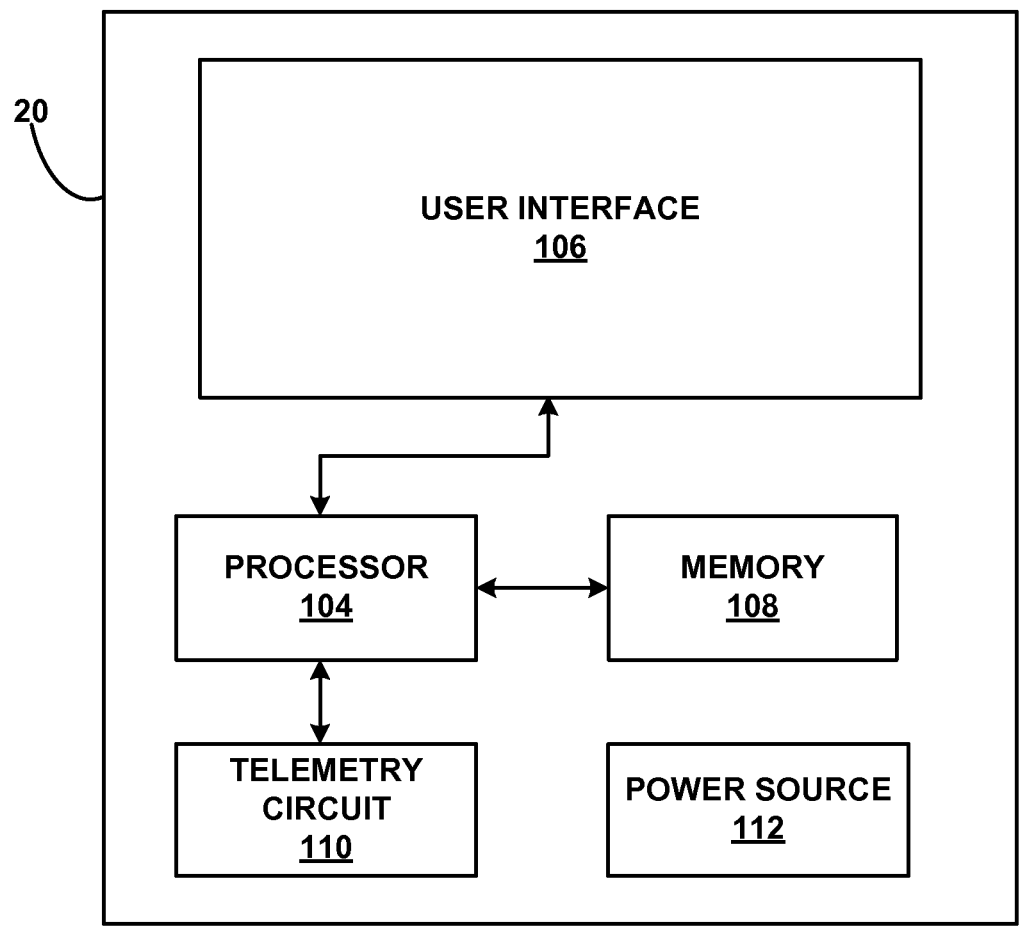
FIG. 6 is a functional block diagram illustrating various components of an example external programmer for an implantable medical device consistent with this disclosure.

FIG. 6 is a functional block diagram illustrating various components of an external programmer 20 for IMDs 14 or 26. Programmer 20 may be a handheld computing device, a workstation or another dedicated or multifunction computing device. For example, programmer 20 may be a general purpose computing device (e.g., a personal computer, personal digital assistant (PDA), cell phone, and so forth) or may be a computing device dedicated to programming the IMD. As shown in FIG. 6, external programmer 20 includes processor 104, memory 108, telemetry circuit 110, user interface 106, and power source 112. External programmer 20 may be embodied as patient programmer 30 (FIG. 2) or clinician programmer 60 (FIG. 3).

Processor 104 processes instructions by memory 108 and may store user input received through user interface 106 into the memory when appropriate for the current therapy. In addition, processor 104 provides and supports any of the functionality described herein with respect to each example of user interface 106. Processor 104 may comprise any one or more of a microprocessor, DSP, ASIC, FPGA, or other digital logic circuitry, and the functions attributed to programmer 104 may be embodied as software, firmware, hardware or any combination thereof.

Memory 108 may include any one or more of a RAM, ROM, EEPROM, flash memory or the like. Memory 108 may include instructions for operating user interface 106, telemetry module 110 and managing power source 112. Memory 108 may store program instructions that, when executed by processor 104, cause processor 104 and programmer 20 to provide the functionality ascribed to them herein. Memory 108 also includes instructions for generating and delivering programming commands to IMD 14, such as a programming command that instructs IMD 14 to activate or deactivate a posture responsive therapy mode, wherein postures are also associated with a specific time that a given posture was detected and recorded. Memory 108 may also include a removable memory portion that may be used to provide memory updates or increases in memory capacities. A removable memory may also allow patient data to be easily transferred to another computing device, or to be removed before programmer 20 is used to program therapy for another patient.

A clinician, patient 12 or another user (e.g., a patient caretaker) interacts with user interface 106 in order to manually change the stimulation parameter values of a program, change programs within a group, turn posture responsive stimulation ON or OFF, view therapy information, view posture state information defined at different times of day, or otherwise communicate with IMDs 14 or 26.

User interface 106 may include a screen and one or more input mechanisms, such as buttons as in the example of patient programmer, 30 that allows external programmer 20 to receive input from a user. Alternatively, user interface 106 may additionally or only utilize a touch screen display, as in the example of clinician programmer 60. The screen may be a liquid crystal display (LCD), dot matrix display, organic light-emitting diode (OLED) display, touch screen, or any other device capable of delivering and/or accepting information. For visible posture state indications, a display screen may suffice. For audible and/or tactile posture state indications, programmer 20 may further include one or more audio speakers, voice synthesizer chips, piezoelectric buzzers, or the like.

Telemetry circuit 110 allows the transfer of data to and from IMD 14, or IMD 26. Telemetry circuit 110 may communicate automatically with IMD 14 at a scheduled time or when the telemetry circuit detects the proximity of the stimulator. Alternatively, telemetry circuit 110 may communicate with IMD 14 when signaled by a user through user interface 106. To support RF communication, telemetry circuit 110 may include appropriate electronic components, such as amplifiers, filters, mixers, encoders, decoders, and the like. Power source 112 may be a rechargeable battery, such as a lithium ion or nickel metal hydride battery. Other rechargeable or conventional batteries may also be used. In some cases, external programmer 20 may be used when coupled to an alternating current (AC) outlet, i.e., AC line power, either directly or via an AC/DC adapter.

Although not shown in FIG. 6, in some examples, external programmer 20 may include a charger module capable of recharging a power source, such as a rechargeable battery that may be included in power source 90 of IMD 14. Hence, in some cases, the programmer may be integrated with recharging components to form a combined programmer/recharger unit.

Figure 7:
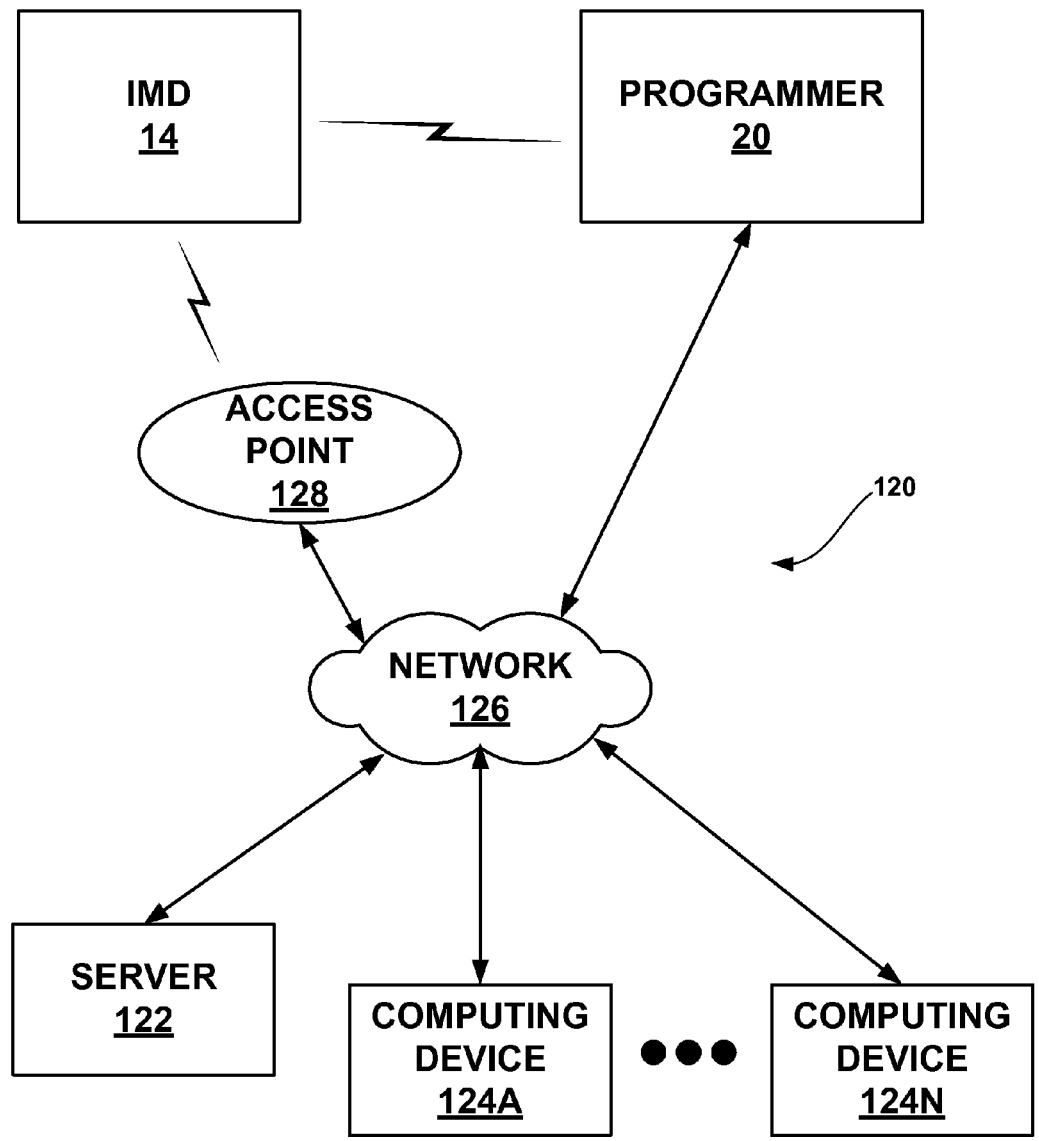
FIG. 7 is a block diagram illustrating an example system that includes an external device, such as a server, and one or more computing devices that are coupled to an implantable medical device and external programmer shown in FIGS. 1A-1C via a network.

FIG. 7 is a block diagram illustrating an example system 120 that includes an external device, such as a server 122, and one or more computing devices 124A-124N, that are coupled to IMD 14 and external programmer 20 shown in FIGS. 1A-1C via a network 126. In this example, IMD 14 may use its telemetry circuit 88 (FIG. 4) to communicate with external programmer 20 via a first wireless connection, and to communicate with an access point 128 via a second wireless connection. In other examples, IMD 26 may also be used in place of IMD 14, and external programmer 20 may be either patient programmer 30 or clinician programmer 60.

In the example of FIG. 7, access point 128, external programmer 20, server 122, and computing devices 124A-124N are interconnected, and able to communicate with each other, through network 126. In some cases, one or more of access point 128, external programmer 20, server 122, and computing devices 124A-124N may be coupled to network 126 through one or more wireless connections. IMD 14, external programmer 20, server 122, and computing devices 124A-124N may each comprise one or more processors, such as one or more microprocessors, DSPs, ASICs, FPGAs, programmable logic circuitry, or the like, that may perform various functions and operations, such as those described in this disclosure.

Access point 128 may comprise a device, such as a home monitoring device, that connects to network 126 via any of a variety of connections, such as telephone dial-up, digital subscriber line (DSL), or cable modem connections. In other examples, access point 128 may be coupled to network 126 through different forms of connections, including wired or wireless connections.

During operation, IMD 14 may collect and store various forms of data. For example, IMD 14 may collect sensed posture state information during therapy that indicate how patient 12 moves throughout each day. The posture information may be associated with timing at which such posture information is collected, and therapy may be defined for different posture-timing combinations. Accordingly, the same posture state may result in delivery of different therapies, e.g., with one or more different therapy parameter settings, at different times of day, similar times of different days of the week, or any different times generally.

In some cases, IMD 14 may directly analyze the collected data to evaluate the patient 12 posture state, such as what percentage of time patient 12 was in each identified posture and when such posture occurred. In other cases, however, IMD 14 may send stored data relating to posture state information and timing of the posture state information to external programmer 20 and/or server 122, either wirelessly or via access point 128 and network 126, for remote processing and analysis. For example, IMD 14 may sense, process, trend and evaluate the sensed posture state information. This communication may occur in real time, and network 126 may allow a remote clinician to review the current patient posture state or a past posture state at a particular time by receiving a presentation of a posture state indication on a remote display, e.g., computing device 124A. Alternatively, processing, trending and evaluation functions may be distributed to other devices such as external programmer 20 or server 122, which are coupled to network 126. In addition, posture state information may be archived by any of such devices, e.g., for later retrieval and analysis by a clinician, and the timing of such posture state information may aid such analysis.

In some cases, IMD 14, external programmer 20 or server 122 may process posture state information or raw data and/or therapy information into a displayable posture state report, which may be displayed via external programmer 20 or one of computing devices 124A-124N. The posture state report may contain trend data for evaluation by a clinician, e.g., by visual inspection of graphic data. In some cases, the posture state report may include the number of activities patient 12 conducted, a percentage of time patient 12 was in each posture state, the timing of each given occurrence of a posture state transition, the average time patient 12 was continuously within a posture state, what group or program was being used to deliver therapy during each activity the timing of such activities, the number of adjustments to therapy during each respective posture state and the timing of such adjustments, or any other information relevant to patient 12 therapy, based on analysis and evaluation performed automatically by IMD 14, external programmer 20 or server 122. A clinician or other trained professional may review and/or annotate the posture state report, and possibly identify any problems or issues with the therapy that should be addressed.

In the manner of FIG. 7, a clinician, physician, technician, or even patient 12, may review objectivity data with respect to the posture states of patient 12 and the timing thereof. The objectivity data may be sleep quality information or proportional posture information that indicates how patient 12 has been moving during the symptom diagnosis or delivered therapy at any given time and posture. The user may remotely monitor the progress and trends of patient 12, limiting the number of times that patient 12 may need to physically visit the clinician. The remote monitoring supported by system 120 may also reduce the time needed to find efficacious therapy parameters by allowing the clinician to more frequently monitor sleep quality information and proportional posture information. Any of the user interfaces described herein with respect to patient programmer 30 or clinician programmer 60 may also be presented via any of computing devices 124A-124N.

In some cases, server 122 may be configured to provide a secure storage site for archival of posture state information that has been collected from IMD 14 and/or external programmer 20. Network 126 may comprise a local area network, wide area network, or global network, such as the Internet. In some cases, external programmer 20 or server 122 may assemble posture state information in web pages or other documents for viewing by trained professionals, such as clinicians, via viewing terminals associated with computing devices 124A-124N. System 120 may be implemented, in some aspects, with general network technology and functionality similar to that provided by the Medtronic CareLink® Network developed by Medtronic, Inc., of Minneapolis, Minn.

Although some examples of the disclosure may involve posture state information and timing information, system 120 may be employed to distribute any information relating to the treatment of patient 12 and the operation of any device associated therewith. For example, system 120 may allow therapy errors or device errors to be immediately reported to the clinician. In addition, system 120 may allow the clinician to remotely intervene in the therapy and reprogram IMD 14, patient programmer 30, or communicate with patient 12. In an additional example, the clinician may utilize system 120 to monitor multiple patients and share data with other clinicians in an effort to coordinate rapid evolution of effective treatment of patients.

Furthermore, although the disclosure is described with respect to SCS therapy, such techniques may be applicable to IMDs that convey other therapies in which posture state information is important, such as, e.g., DBS, pelvic floor stimulation, gastric stimulation, occipital stimulation, functional electrical stimulation, and the like. Also, in some aspects, techniques for evaluating posture state information, as described in this disclosure, may be applied to IMDs that are generally dedicated to sensing or monitoring and do not include stimulation or other therapy components. For example, an implantable monitoring device may be implanted in conjunction with an implantable stimulation device, and be configured to evaluate sensing integrity of leads or electrodes associated with the implantable monitoring device based on sensed signals evoked by delivery of stimulation by the implantable stimulation device.

Figure 8A:
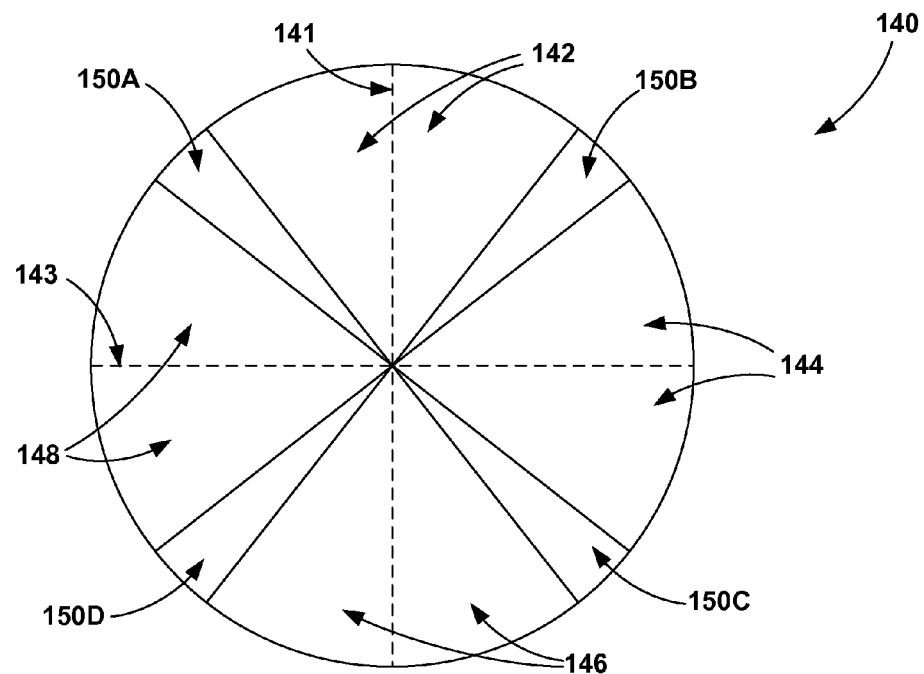
FIGS. 8A-8C are conceptual illustrations of posture state spaces that may be used to define a posture state of a patient based on one or more signals generated by a posture state module.
Figure 8B:
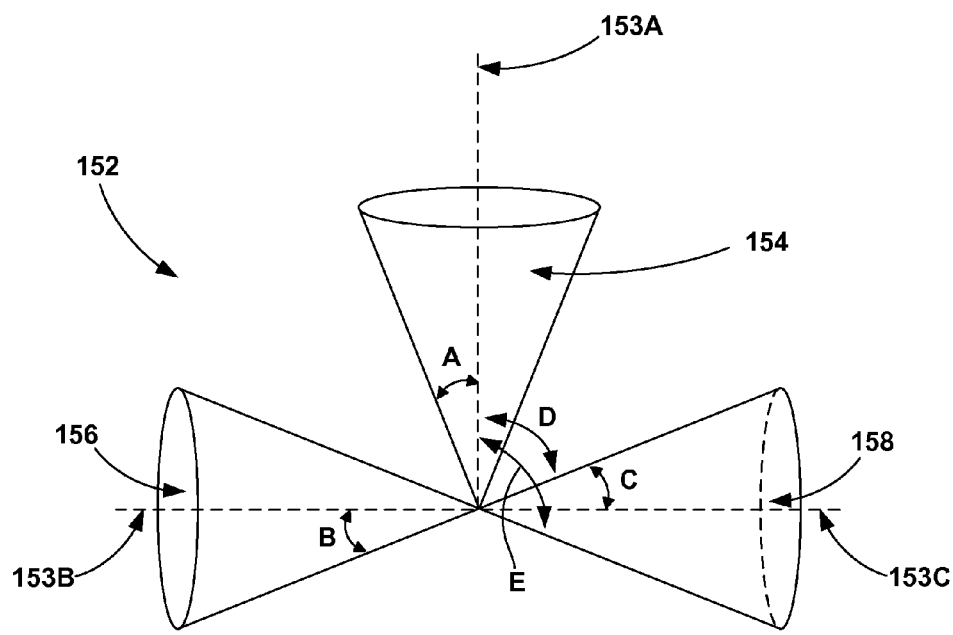
Figure 8C:
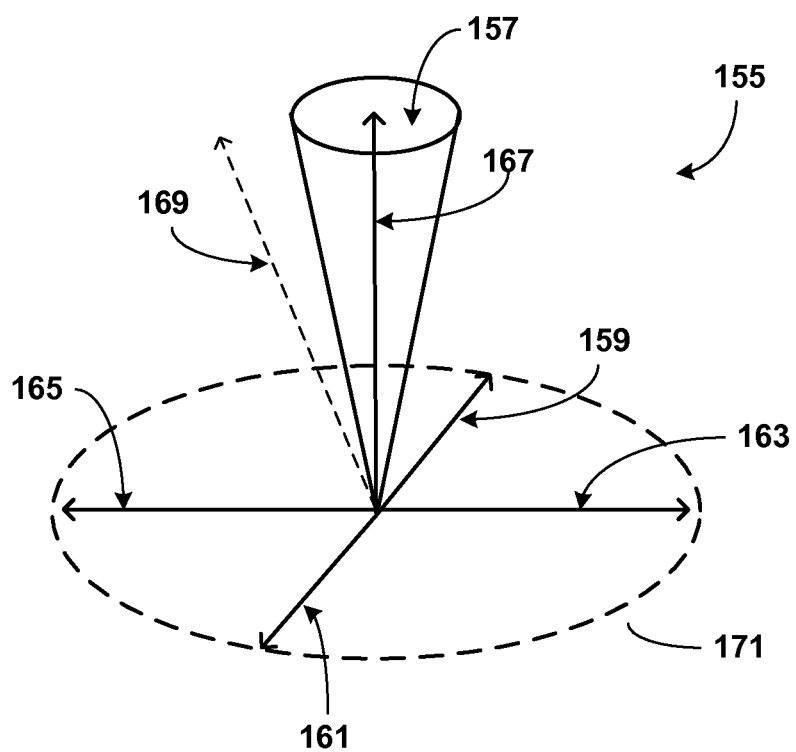

FIGS. 8A-8C are conceptual illustrations of posture state spaces 140, 152, 155 within which posture state reference data may define the posture state of patient 12. Posture state reference data may define certain regions associated with particular posture states of patient 12 within the respective posture state spaces 140, 152, 155. The output of one or more posture state sensors may be analyzed by posture state module 86 with respect to posture state spaces 140, 152, 155 to determine the posture state of patient 12. For example, if the output of one or more posture state sensors is within a particular posture region defined by posture state reference data, posture state module 86 may determine that patient 12 is within the posture state associated with the respective posture state region.

In some cases, one or more posture state regions may be defined as posture state cones. Posture state cones may be used to define a posture state of patient 12 based on the output from a posture state sensor of a posture state according to an example method for posture state detection. A posture state cone may be centered about a posture state reference coordinate vector that corresponds to a particular posture state. In the examples of FIGS. 8A and 8B, the posture state module 86 of IMD 14 or IMD 26 may use a posture state sensor, e.g., a three-axis accelerometer that provides data indicating the posture state of patient 12, to sense posture vectors. While the sensed data may be indicative of any posture state, postures of patient 12 will generally be used below to illustrate the concept of posture cones. As shown in FIG. 8A, posture state space 140 represents a vertical plane dividing patient 12 from left and right sides, or the sagittal plane. A posture state parameter value from two axes of the posture state sensor may be used to determine the current posture state of patient 12 according to the posture state space 140. The posture state data may include x, y and z coordinate values.

A posture cone may be defined by a reference coordinate vector for a given posture state in combination with a distance or angle defining a range of coordinate vectors within a cone surrounding the posture reference coordinate vector. Alternatively, a posture cone may be defined by a reference coordinate vector and a range of cosine values computed using the reference coordinate vector as an adjacent vector and any of the outermost vectors of the cone as a hypotenuse vector. If a sensed posture state vector is within an applicable angle or distance of the reference coordinate vector, or if the sensed posture state vector and the reference coordinate vector produce a cosine value in a specified cosine range, then posture state vector is determined to reside within the posture cone defined by the reference coordinate vector.

Posture state space 140 is segmented into different posture cones that are indicative of a certain posture state of patient 12. In the example of FIG. 8A, upright cone 142 indicates that patient 12 is sitting or standing upright, lying back cone 148 indicates that patient 12 is lying back down, lying front cone 144 indicates that patient 12 is lying chest down, and inverted cone 146 indicates that patient 12 is in an inverted position. Other cones may be provided, e.g., to indicate that patient 12 is lying on the right side or left side. For example, a lying right posture cone and a lying left posture cone positioned outside of the sagittal plane illustrated in FIG. 8A. In particular, the lying right and lying left posture cones may be positioned in a coronal plane substantially perpendicular to the sagittal plane illustrated in FIG. 8A. For ease of illustration, lying right and lying left cones are not shown in FIG. 8A.

Vertical axis 141 and horizontal axis 143 are provided for orientation of posture state area 140, and are shown as orthogonal for purposes of illustration. However, posture cones may have respective posture reference coordinate vectors that are not orthogonal in some cases. For example, individual reference coordinate vectors for cones 142 and 146 may not share the same axis, and reference coordinate vectors for cones 144 and 148 may not share the same axis. Also, reference coordinate vectors for cones 144 and 148 may or may not be orthogonal to reference coordinates vectors for cones 142, 146. Therefore, although orthogonal axes are shown in FIG. 8A for purposes of illustration, respective posture cones may be defined by individualized reference coordinate vectors for the cones.

IMD 14 may monitor the posture state parameter value of the posture state sensor to produce a sensed coordinate vector and identify the current posture of patient 12 by identifying which cone the sensed coordinated vector of the posture state sensor module 86 resides. For example, if the posture state parameter value corresponds to a sensed coordinate vector that falls within lying front cone 144, IMD 14 determines that patient 12 is lying down on their chest. IMD 14 may store this posture information as a determined posture state or as raw output from the posture state sensor associated with a given time, change therapy according to the posture at that given time, or both. Additionally, IMD 14 may communicate the posture information to patient programmer 30 along with the timing associated with the posture information so that the patient programmer can present a posture state indication to patient 12 for that time.

In addition, posture state area 140 may include hysteresis zones 150A, 150B, 150C, and 150D (collectively "hysteresis zones 150"). Hysteresis zones 150 are positions within posture state area 140 where no posture cones have been defined. Hysteresis zones 150 may be particularly useful when IMD 14 utilizes the posture state information and posture cones to adjust therapy automatically at a particular time or time interval. If the posture state sensor indicates that patient 12 is in upright cone 142, IMD 14 would not detect that patient 12 has entered a new posture cone until the posture state parameter value indicates a different posture cone. For example, if IMD 14 determines that patient 12 moves to within hysteresis zone 150A from upright cone 142, IMD 14 retains the posture as upright. In this manner, IMD 14 does not change the corresponding therapy until patient 12 fully enters a different posture cone for a particular time or time interval. Hysteresis zones 150 prevent IMD 14 from continually oscillating between different therapies when patient 12's posture state resides near a posture cone boundary.

Each posture cone 142, 144, 146, 148 may be defined by an angle in relation to a reference coordinate vector defined for the respective posture cone. Alternatively, some posture cones may be defined by an angle relative to a reference coordinate vector for another posture cone. For example, lying postures may be defined by an angle with respect to a reference coordinate vector for an upright posture cone. In each case, as described in further detail below, each posture cone may be defined by an angle in relation to a reference coordinate posture vector defined for a particular posture state. The reference coordinate vector may be defined based on posture sensor data generated by a posture state sensor while patient 12 occupies a particular posture state desired to be defined using the reference coordinate vector. For example, a patient may be asked to occupy a posture so that a reference coordinate vector can be sensed for the respective posture. In this manner, vertical axis 141 may be specified according to the patient's actual orientation. Then, a posture cone can be defined using the reference coordinate vector as the center of the cone.

Vertical axis 141 in FIG. 8A may correspond to a reference coordinate vector sensed while the patient was occupying an upright posture state. Similarly, a horizontal axis 143 may correspond to a reference coordinate vector sensed while the patient is occupying a lying posture state. A posture cone may be defined with respect to the reference coordinate vector. Although a single axis is shown extending through the upright and inverted cones 142, 146, and another single axis is shown extending through the lying down and lying up cones 144, 148, individual reference coordinate vectors may be used for respective cones, and the reference coordinate vectors may not share the same axes, depending on differences between the reference coordinate vectors obtained for the posture cones.

Posture cones may be defined by the same angle or different angles, symmetrical to either axis, or asymmetrical to either axis. For example, upright cone 142 may have an angle of eighty degrees, +40 degrees to −40 degrees from the positive vertical axis 141. In some cases, lying cones may be defined relative to the reference coordinate vector of the upright cone 142. For example, lying up cone 148 may have an angle of eighty degrees, −50 degrees to −130 degrees from the positive vertical axis 141. Inverted cone 146 may have an angle of eighty degrees, −140 degrees to +140 degrees from vertical axis 141. In addition, lying down cone 144 may have an angle of eighty degrees, +50 degrees to +130 degrees from the positive vertical axis 141. In other examples, each posture cone may have varying angle definitions, and the angles may change during therapy delivery to achieve the most effective therapy for patient 12 for any given time or time interval.

Alternatively or additionally, instead of an angle, posture cones 144, 146, 148, 148 may be defined by a cosine value or range of cosine values in relation to vertical axis 141, horizontal axis 143, or some other axis, such as, e.g., individual reference coordinate vectors for the respective cones. For example, a posture cone may be defined by a cosine value that defines the minimum cosine value, calculated using a reference coordinate vector and a respective coordinate vector sensed by a posture state sensor at any point in time. In the cosine computation, the value (adjacent/hypotenuse) can be computed using the magnitude of the coordinate reference vector as the adjacent and a vector at the outermost extent of the cone as the hypotenuse to define a range of cosine values consistent with the outer bound of the cone.

For upright cone 142, the cosine range may extend from the maximum cosine value of 1.0, corresponding to a sensed vector that matches the reference coordinate vector of the upright cone, to a minimum cosine value that corresponds to a sensed vector at the outer limit of the upright cone. As another example, for lying cone 144, the cosine range may extend from the maximum cosine value of 1.0, corresponding to a sensed vector that matches the reference coordinate vector of the lying cone, to a minimum cosine value that corresponds to a sensed vector at the outer limit of the lying cone. Alternatively, the lying cone 144 may be defined with reference to the upright cone 142, such that the cosine range may extend between a maximum and minimum values determined relative to the reference coordinate vector for the upright cone.

In other examples, posture state area 140 may include additional posture cones than those shown in FIG. 8A. For example, a reclining cone may be located between upright cone 142 and lying back cone 148 to indicate when patient 12 is reclining back (e.g., in a dorsal direction). In this position, patient 12 may need a different therapy to effectively treat symptoms. Different therapy programs may provide efficacious therapy to patient 12 when patient 12 is in each of an upright posture (e.g., within upright cone 142), lying back posture (e.g., within lying back cone 148), and a reclining back posture. Thus, a posture cone that defines the reclining back posture may be useful for providing efficacious posture-responsive therapy to patient 12. In other examples, posture state area 140 may include fewer posture cones than cones 142, 144, 146, 148 shown in FIG. 8A. For example, inverted cone 146 may be replaced by a larger lying back cone 148 and lying front cone 144. In any case, according to this disclosure, both the detected posture and the timing associated with such detected posture may be used to define therapy parameters.

FIG. 8B illustrates an example posture state space 152 that is a three-dimensional space in which the posture state parameter value from the posture state sensor is placed in relation to the posture cones. Posture state space 152 is substantially similar to posture state area 140 of FIG. 8A. However, the posture state parameter value derived from all three axes of a 3-axis accelerometer may be used to accurately determine the posture state of patient 12. In the example of FIG. 8B, posture state space 152 includes upright cone 154, lying back cone 156, and lying front cone 158. Posture state space 152 also includes hysteresis zones (not shown) similar to those of posture state area 140. In the example of FIG. 8B, the hysteresis zones are the spaces not occupied by a posture cone, e.g., upright cone 154, lying back cone 156, and lying front cone 158.

Posture cones 154, 156 and 158 also are defined by a respective center line 153A, 153B, or 153C, and associated cone angle A, B or C. For example, upright cone 154 is defined by center line 153A that runs through the center of upright cone 154. Center line 153A may correspond to an axis of the posture state sensor or some other calibrated vector. In some embodiments, each center line 153A, 153B, 153C may correspond to a posture reference coordinate vectors defined for the respective postures, e.g., the upright posture. For instance, assuming that patient 12 is standing, the DC portion of the x, y, and z signals detected by the posture state sensor of posture state module 86 define a posture vector that corresponds to center line 153A. The x, y, and z signals may be measured while patient 12 is known to be in a specified position, e.g., standing, and the measured vector may be correlated with the upright posture state. Thereafter, when the DC portions of the posture state sensor signal are within some predetermined cone tolerance or proximity, e.g., as defined by an angle, distance or cosine value, of the posture reference coordinate vector (i.e., center line 153A), it may be determined that patient 12 is in the upright posture. In this manner, a sensed posture coordinate vector may be initially measured based on the output of one or more posture state sensors of posture state module 86, associated with a posture state, such as upright, as a reference coordinate vector, and then later used to detect a patient's posture state.

As previously indicated, it may be desirable to allow some tolerance to be associated with a defined posture state, thereby defining a posture cone or other volume. For instance, in regard to the upright posture state, it may be desirable to determine that a patient who is upright but leaning slightly is still in the same upright posture state. Thus, the definition of a posture state may generally include not only a posture reference coordinate vector (e.g., center line 153A), but also a specified tolerance. One way to specify a tolerance is by providing an angle, such as cone angle A, relative to coordinate reference vector 153A, which results in posture cone 154 as described herein. Cone angle A is the deflection angle, or radius, of upright cone 154. The total angle that each posture cone spans is double the cone angle. The cone angles A, B, and C may be generally between approximately 1 degree and approximately 70 degrees. In other examples, cone angles A, B, and C may be between approximately 10 degrees and 30 degrees. In the example of FIG. 8B, cone angles A, B, and C are approximately 20 degrees. Cone angles A, B, and C may be different, and center lines 153A, 153B, and 153C may not be orthogonal to each other.

In some examples, a tolerance may be specified by a cosine value or range of cosine values. The use of cosine values, in some cases, may provide substantial processing efficiencies. As described above, for example, a minimum cosine value, determined using the reference coordinate vector as adjacent and sensed coordinate vector as hypotenuse, indicates the range of vectors inside the cone. If a sensed coordinate vector, in conjunction with the reference coordinate vector for a posture cone, produces a cosine value that is less than the minimum cosine value for the posture cone, the sensed coordinate vector does not reside within the pertinent posture cone. In this manner, the minimum cosine value may define the outer bound of a range of cosine values within a particular posture cone defined in part by a reference coordinate vector.

While center lines 153A, 153B, 153C of each of the posture cones 154, 156, 158, respectively, are shown in FIG. 8B as being substantially orthogonal to each other, in other examples, center lines 153A, 153B, and 153C may not be orthogonal to each other. Again, the relative orientation of center lines 153A, 153B, 153C may depend on the actual reference coordinate vector output of the posture state sensor of posture state module 86 of IMD 14 when patient 12 occupies the respective postures.

In some cases, all of the posture cones may be individually defined based on actual reference coordinate vectors. Alternatively, in some cases, some posture cones may be defined with reference to one or more reference coordinate vectors for one or more other posture cones. For example, lying reference coordinate vectors could be assumed to be orthogonal to an upright reference coordinate vector. Alternatively, lying reference coordinate vectors could be individually determined based on sensed coordinate vectors when the patient is in respective lying postures. Hence, the actual reference coordinate vectors for different postures may be orthogonal or non-orthogonal with respect to one another.

In addition to upright cone 154, lying back cone 156, and lying front cone 158, posture state space 152 may include additional posture cones. For example, a lying right cone may be provided to define a patient posture in which patient 12 is lying on his right side and a lying left cone may be provided to define a patient posture in which patient 12 is lying on his left side. In some cases, the lying right cone and lying left cone may be positioned approximately orthogonal to upright cones 154, in approximately the same plane as lying back cone 156 and lying front cone 158. Moreover, posture state space 152 may include an inverted cone positioned approximately opposite of upright cone 154. Such a cone indicates that the patient's posture is inverted from the upright posture, i.e., upside down.

In some examples, to detect the posture state of a patient, posture state module 86 of IMD 14 may determine a sensed coordinate vector based on the posture sensor data generated by one or more posture state sensors, and then analyze the sensed coordinate vector with respect to posture cones 154, 156, 158 of FIG. 8B. For example, in a case in which a posture cone is defined by a reference coordinate vector and a tolerance angle, e.g., tolerance angle "A," posture state module 86 may determine whether the sensed coordinate vector is within upright posture cone 154 by calculating the angle between the sensed coordinate vector and reference coordinate vector, and then determine whether the angle is less than the tolerance angle "A." If so, posture state module 86 determines that the sensed coordinate vector is within upright posture cone 154 and detects that patient 12 is in the upright posture. If posture state module 86 determines that sensed coordinate vector is not within upright posture cone 154, posture state module 86 detects that patient 12 is not in the upright posture.

Posture state module 86 may analyze the sensed coordinate vector in posture state space 152 with respect to each individual defined posture cone, such as posture cones 156 and 158, in such a manner to determine the posture state of patient 12. For example, posture state module 86 may determine the angle between the sensed coordinate vector and reference coordinate vector of individual posture cones defined for the posture state, and compare the determined angle to the tolerance angle defined for the respective posture cone. In this manner, a sensed coordinate vector may be evaluated against each posture cone until a match is detected, i.e., until the sensed coordinate vector is found to reside in one of the posture cones. Hence, a cone-by-cone analysis is one option for posture detection.

In other examples, different posture detection analysis techniques may be applied. For example, instead of testing a sensed coordinate vector against posture cones on a cone-by-cone basis, a phased approach may be applied where the sensed coordinate vector is classified as either upright or not upright. In this case, if the sensed coordinate vector is not in the upright cone, posture state module 86 may determine whether the sensed coordinate vector is in a lying posture, either by testing the sensed coordinate vector against individual lying posture cones or testing the sensed coordinate vector against a generalized lying posture volume, such as a donut- or toroid-like volume that includes all of the lying postures, and may be defined using an angle or cosine range relative to the upright vector, or relative to a modified or virtual upright vector as will be described. In some cases, if lying postures are defined by cones, the lying volume could be defined as a logical OR of the donut- or toroid-like volume and the volumes of the lying posture cones. If the cones are larger such that some portions extend beyond the lying volume, then those portions can be added to the lying volume using the logical OR-like operation.

If the sensed coordinate vector resides within the donut- or toroid-like lying volume, then the sensed coordinate vector may be tested against each of a plurality of lying posture cones in the lying volume. Alternatively, the posture detection technique may not use lying cones. Instead, a posture detection technique may rely on a proximity test between the sensed coordinate vector and each of the reference coordinate vectors for the respective lying postures. The proximity test may rely on angle, cosine value or distance to determine which of the lying posture reference coordinate vectors is closest to the sensed coordinate vector. For example, the reference coordinate vector that produces the largest cosine value with the sensed coordinate vector as hypotenuse and the reference coordinate vector as adjacent is the closest reference coordinate vector. In this case, the lying posture associated with the reference coordinate vector producing the largest cosine value is the detected posture. Hence, there are a variety of ways to detect posture, such as using posture cones, using an upright posture cone with lying volume and lying posture cone test, or using an upright posture cone with lying volume and lying vector proximity test.

As a further illustration of an example posture detection technique, posture state module 86 may first determine whether patient 12 is generally in a lying posture state or upright posture state by analyzing the sensed coordinate vector in posture state space 152 with respect to an axis 153A for the upright posture state. Axis 153A may correspond to the upright reference coordinate vector. For example, angle "A" may be used to define upright posture cone 154, as described above, and angles "D" and "E" may be used to define the vector space in which patient 12 may be generally considered to be in the lying posture state, regardless of the particular posture state cone, e.g., lying front cone 158, lying back cone 156, lying right cone (not shown), or lying left cone (not shown), in which the sensed coordinate vector falls.

If it is determined that a sensed coordinate vector is not within an angle A of the axis 153A, then it may be determined that the patient is not in the upright posture indicated by the upright posture cone. In this case, it may next be determined whether a sensed coordinated vector is generally in a lying posture space volume, which may be considered somewhat donut- or toroid-like, and may be defined relative to the upright reference coordinate vector 153A. As shown, angles "D" and "E" define the minimum and maximum angle values, respectively, that a sensed vector may form with respect to axis 153A of patient 12 for a determination to be made that the patient is generally in the lying posture state. Again, cosine values may be used instead of angles to determine the positions of sensed coordinate vectors relative to posture cones or other posture volumes, or relative to reference coordinate vectors.

As illustrated, angles "D" and "E" may be defined with respect to vertical axis 153A (which may correspond to an upright reference coordinate vector), which is the reference coordinate vector for the upright posture cone, rather than with respect to a reference coordinate vector of a lying posture state cone. If a sensed vector is within the angular range of D to E, relative to axis 153A, then it can be determined by posture state module 86 that the patient is generally in a lying posture. Alternatively, in some examples, an angle C could be defined according to a generally horizontal axis 153C (which may correspond to one of the lying reference coordinate vectors). In this case, if a sensed vector is within angle C of axis 153C, it can be determined by posture state module 86 that the patient is in a lying posture. In each case, the region generally defining the lying posture state may be referred to as a posture donut or posture toroid, rather than a posture cone. The posture donut may generally encompass a range of vectors that are considered to be representative of various lying down postures.

As an alternative, posture state module 86 may rely on cosine values or a range of cosine values to define the posture donut or toroid with respect to axis 153A. When the sensed vector falls within the vector space defined by axis 153A and angles "D" and "E", or produces a cosine value with the reference coordinate vector 153A in a prescribed range, posture state module 86 may determine that patient 12 is generally in a lying posture state. For example, if the sensed vector and reference coordinate vector 153 produce a cosine value in a first range, the posture is upright. If the cosine value is in a second range, the posture is lying. If the cosine value is outside of the first and second ranges, the posture may be indeterminate. The first range may correspond to the range of cosine values that would be produced by vectors in posture cone 154 defined by angle A, and the second range may be correspond to cosine values that would be produced by vectors in the posture donut defined by angles D and E.

When the sensed vector fall within the vector space defined by axis 153A and angles "D" and "E", as indicated by angle or cosine value, posture state module 86 may then determine the particular lying posture state occupied by patient 12, e.g., lying front, lying back, lying right, or lying left. To determine the particular lying posture state occupied by patient 12, posture state module 86 may analyze the sensed vector with respect to reference coordinate vectors for individual lying posture state cones, e.g., lying front cone 156, lying back cone 158, lying right cone (not shown), and lying left cone (not shown), using one more techniques previously described, such as angle or cosine techniques. For example, posture state module 86 may determine whether the sensed coordinated vector resides within one of the lying posture state cones and, if so, select the posture state corresponding to that cone as the detected posture state.

FIG. 8C illustrates an example posture state space 155 that is a three-dimensional space substantially similar to posture state space 152 of FIG. 8B. Posture state space 155 includes upright posture cone 157 defined by reference coordinate vector 167. The tolerance that defines upright posture cone 157 with respect to reference coordinate vector 167 may include a tolerance angle or cosine value, as described above. In contrast to determining whether a sensed coordinate vector resides in a lying cone, FIG. 8C illustrates a method for detecting a lying posture based on proximity of a sensed coordinate vector to one of the reference coordinate vectors for the lying postures.

As shown in FIG. 8C, posture state space 155 includes four reference coordinate vectors 159, 161, 163, 165, which are associated with lying left, lying right, lying front, and lying back posture states, respectively. Posture state module 86 may have defined each of the four reference coordinated vector 159, 161, 163, 165 based on the output of one or more posture sensors while patient 12 occupied each of the corresponding posture states. Unlike lying front and lying back posture cones 158, 156 in the example of FIG. 8B, the posture state reference data for the four defined posture states corresponding to reference vectors 159, 161, 163, 165 need not include angles defined relative to the respective reference vector in a manner that defines a posture cone. Rather, as will be described below, the respective posture state reference vectors may be analyzed with respect to one another in terms of cosine values to determine which particular reference coordinate vector is nearest in proximity to a sensed coordinate vector.

In some examples, to determine the posture state of patient 12, posture state module 85 may determine whether a sensed coordinate vector is within upright posture cone 157 by analyzing the sensed coordinate vector in view of the tolerance angle or cosine value(s) defined with respect to upright posture reference coordinate vector 167, or whether the sensed vector is within a posture donut or toroid defined by a range of angles (as in FIG. 8B) or cosine values with respect to upright posture reference coordinate vector 167, in which case posture state module 86 may determine that patient 12 is in a general lying posture state.

If posture state module 86 determines that patient 12 is occupying a general lying posture state, posture state module 86 may then calculate the cosine value of the sensed coordinate vector with respect to each lying reference coordinate vectors 159, 161, 163, 165. In such a case, posture state module 86 determines the particular lying posture state of patient 12, i.e., lying left, lying right, lying front, lying back, based on which cosine value is the greatest of the four cosine values. For example, if the cosine value calculated with the sensed vector as the hypotenuse and the lying front reference vector 163 as the adjacent vector is the largest value of the four cosine values, the sensed vector may be considered closest in proximity to lying front reference vector out of the four total reference vectors 159, 161, 163, 165. Accordingly, posture state module 85 may determine that patient 12 is occupying a lying front posture state.

In some examples, posture state module 86 may determine whether patient 12 is generally in a lying posture state based on the relationship of a sensed vector to upright reference vector 167. For example, as described above, a lying posture donut or toroid may be defined with respect to upright posture reference vector 167, e.g., using angles D and E as in FIG. 8B. Such a technique may be appropriate when lying posture reference vectors 159, 161, 163, 165 define a common plane substantially orthogonal to upright posture reference vector 167. However, the lying posture reference vectors 159, 161, 163, 165 may not in fact be orthogonal to the upright reference coordinate vector 167. Also, the lying posture reference vectors 159, 161, 163, 165 may not reside in the same plane.

To account for non-orthogonal reference vectors, in other examples, a lying posture donut or toroid may be defined with respect to a modified or virtual upright reference vector 169 rather than that actual upright posture reference vector 167. Again, such a technique may be used in situations in which the lying reference vectors 159, 161, 163, 165 are not in a common plane, or the common plane of reference vector 159,

161, 163, 165 is not substantially orthogonal to upright reference vector 167. However, use of the example technique is not limited to such situations.

To define virtual upright reference vector 169, posture state module 86 may compute the cross-products of various combinations of lying reference vectors 159, 161, 163, 165 and average the cross product values. In the example of FIG. 8C, posture state module 86 may compute four cross products and average the four cross product vectors to yield the virtual upright vector. The cross product operations that may be performed are: lying left vector 159 x lying back vector 165, lying back vector 165 x lying right vector 161, lying right vector 161 x lying front vector 163, and lying front vector 163 x lying left vector 159. Each cross product yields a vector that is orthogonal to the two lying reference vectors that were crossed. Averaging each of the cross product vectors yields a virtual upright reference vector that is orthogonal to lying plane 171 approximately formed by lying reference vectors 159, 161, 163, 165.

Using virtual upright reference vector 169, posture state module 86 may define a lying posture donut or toroid in a manner similar to that described with respect to upright reference vector 167, but instead with respect to virtual upright reference vector 169. In particular, when posture state module 86 determines that the patient is not in the upright posture, the posture state module determines whether the patient is in a lying posture based on an angle or cosine value with respect to the virtual upright reference vector 169.

Posture state module 86 may still determine whether patient 12 is in an upright posture state using upright posture cone 157. If posture state module 86 determines that patient 12 is occupying a general lying posture state based on the analysis of the sensed coordinate vector with respect to virtual upright reference vector 169, posture state module 86 may then calculate the cosine value of the sensed coordinate vector (as hypotenuse) with respect to each lying reference coordinate vectors 159, 161, 163, 165 (as adjacent).

In such a case, posture state module 86 determines the particular lying posture state of patient 12, i.e., lying left, lying right, lying front, lying back, based on which cosine value is the greatest of the four cosine values. For example, if the cosine value calculated with the lying front reference vector 163 is the largest value of the four cosine values, the sensed vector may be considered closest in proximity to lying front reference vector out of the four total reference vectors 159, 161, 163, 165. Accordingly, posture state module 85 may determine that patient 12 is occupying a lying front posture state.

Additionally, posture state definitions are not limited to posture cones. For example, a definition of a posture state may involve a posture vector and a tolerance, such as a maximum distance from the posture vector. So long as a detected posture vector is within this maximum distance from the posture vector that is included in the definition of the posture state, patient 12 may be classified as being in that posture state. This alternative method may allow posture states to be detected without calculating angles, as is exemplified above in the discussion related to posture cones.

Further to the foregoing, posture states may be defined that are specific to a particular patient's activities and/or profession. For instance, a bank teller may spend a significant portion of his working day leaning forward at a particular angle. A patient-specific "Leaning Forward" posture state including this angle may be defined in order to provide efficacious therapy to the patient for the posture state frequented by the patient at work. However, if this same posture is detected in times unassociated with work, therapy may be applied differently under the presumption that the patient only works during work hours. The cone angle or other tolerance value selected for this posture state may be specific to the particular posture state definition for this patient. In this manner, the defined posture states may be tailored to a specific user's lifestyle and common daily routine, and need not be "hard-coded" in the IMD.

In some examples, individual posture states (or posture states at specific times) may be linked together, thereby tying posture states to a common set of posture reference data and a common set of therapy parameter values. This may, in effect, merge multiple posture cones for purposes of posture state-based selection of therapy parameter values. For example, all lying posture state cones (back, front, left, right) could be treated as one cone or a donut/toroid, e.g., using a technique the same as or similar to that described with respect to FIGS. 8B and 8C to define a donut, toroid or other volume. One program group or common set of therapy parameter values may apply to all posture states in the same merged cone for a given time interval (e.g., time of day), according to the linking status of the posture states, as directed via programmer 20.

Merging posture cones or otherwise linking a plurality of posture states together may be useful for examples in which a common set of therapy parameter values provides efficacious therapy to patient 12 for the plurality of posture states. In such an example, linking a plurality of posture states together may help decrease the power consumption required to provide posture-responsive therapy to patient 12 because the computation required to track patient posture states and provide responsive therapy adjustments may be minimized when a plurality of posture states are linked together.

Linking of posture states also may permit a therapy parameter value adjustment in one posture state to be associated with multiple posture states at the same time or at similar time intervals of different days. For example, the same amplitude level for one or more programs may be applied to all of the posture states in a linked set of posture states at a given time of day. Alternatively, the lying down posture states may all reside within a "donut" or toroid that would be used instead of separate comes 156 and 158, for example. The toroid may be divided into sectional segments that each correspond to different posture states, such as lying (back), lying (front), lying (right), lying (left) instead of individual cones. In this case, different posture reference data and therapy parameter values may be assigned to the different sectional segments of the toroid.

Yet another aspect of this disclosure contemplates that posture states at particular times may define different tolerances for the same vector, different vectors, and/or different hysteresis zones. In other words, the posture states themselves, and/or the manner in which posture states are defined, may be dependent upon the time of day or day of week or month. In this case, posture state detection may differ at different times of day, which may provide processing efficiency. For instance, posture state classification or selection may be conducted more quickly when different posture states define different tolerances because postures typically used at a given time of day may be identified more quickly. Processing efficiency and power conservation may also be promoted when different posture states and timings associated with the posture states define different tolerances for purposes of posture state detection. At nighttime, for example, the lying down posture may be more quickly defined than during daytime. In this case, at nighttime, when lying down is more expected, the detection of lying down posture state may be performed more quickly, while at daytime, when lying down less more expected, the detection of lying down posture state may be performed more slowly and more accurately to make more sure that lying down is actually occurring. In some cases, posture states associated with given time periods may be expected. Therefore, expected posture states may be favored for detection at expected times and other types of posture states may be favored at other times. Sampling rates or other parameters associated with posture state detection and/or classification may also be changed at different times of day, e.g., to save power by sampling at lower rates at nighttime.

Furthermore, the posture state classification techniques (such as described above in the context of FIGS. 8A-8C) may also change based on time of day, day of the week, day of the month, week of the month, or the like. For instance, the sensor sampling rate could be decreased at nighttime to save power since the patient is likely not moving very much at night time. In other examples, sensor signals may use different filtering techniques at different times of day in order to take into account more noisy environments that may exist during the day. DC signals used to detect posture states may be averaged over a time period T as a smoothing technique, and the time T could be changed based on time of day, as required. Similarity, AC signals used to detect activity may be associated with a noise threshold, with signals having an amplitude smaller than the noise threshold being disregarded. In this case, this noise threshold could be changed based on time of day, or day of week. As an example, sampling rates may be increased and noises thresholds may be increased during an activity time period, such as during bowling night. Selecting operations, in this manner, could save power, and/or result in more accurate posture state detection.

Figure 9:
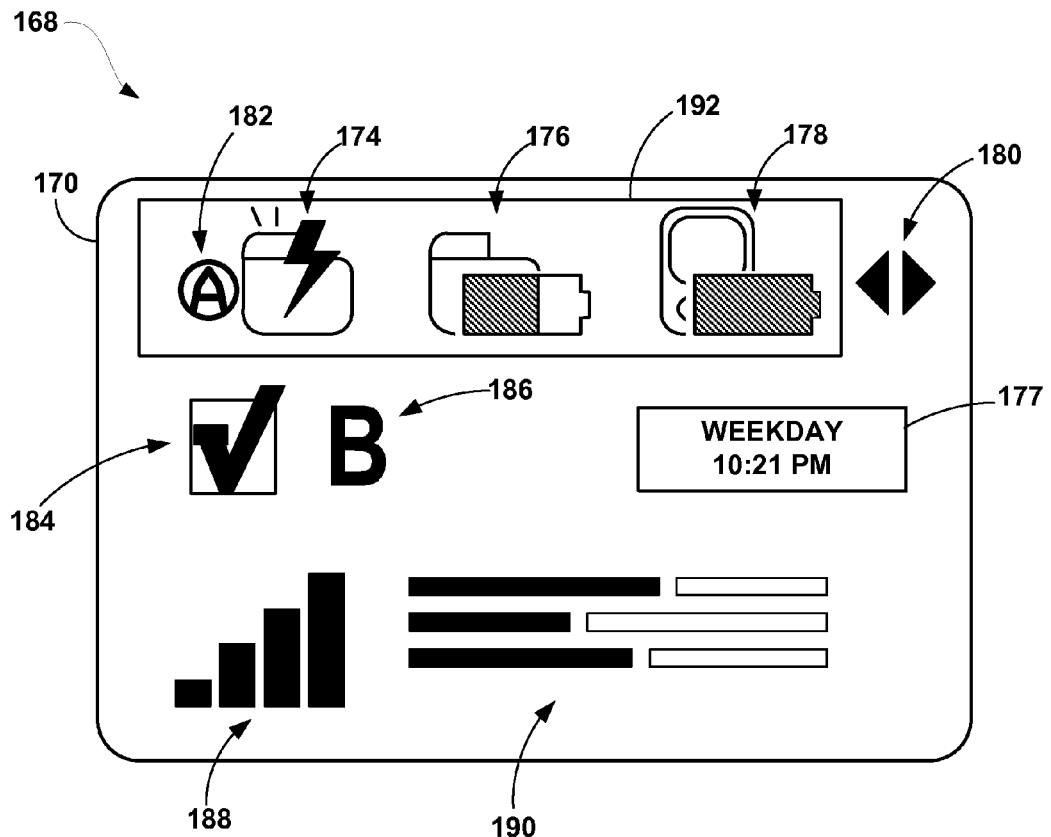
FIG. 9 is a conceptual diagram illustrating an example user interface of a patient programmer for delivering therapy information to the patient.

FIG. 9 is a conceptual diagram illustrating an example user interface 168 of a patient programmer 30 for delivering therapy information to patient 12. In other examples, a user interface similar to user interface 168 may also be presented by clinician programmer 60. In the example of FIG. 9, display 36 of patient programmer 30 provides user interface 168 to the user, such as patient 12, via screen 170. Screen 170 includes stimulation icon 174, IMD battery icon 176, programmer battery icon 178, navigation arrows 180, automatic posture response icon 182, group selection icon 184, group identifier 186, program identifier 188, amplitude graph 190, and selection box 192. User interface 168 provides information to patient 12 regarding group, program, amplitude, and automatic posture response status. User interface 168 may be configurable, such that more or less information may be provided to patient 12, as desired by the clinician or patient 12. Timing (e.g., time of day, day of the week, specific type of day, specific time slot of specific types of days, or the like) associated with any detected posture state may be displayed in accordance with this disclosure. Timing is illustrated in user interface 168 as element 177.

Selection box 192 allows patient 12 to navigate to other screens, groups, or programs using navigation arrows 180 to manage the therapy. In the example, of screen 170, selection box 192 is positioned so that patient 12 may use arrows 44 and 48 (FIG. 2) of control pad 40 of programmer 30 to move to the automatic posture response screen, the volume screen, the contrast or illumination screen, the time screen, and the measurement unit screen of patient programmer 30. In these screens, patient 12 may be able to control the use of the automatic posture response feature and adjust the patient programmer 30 features. Patient 12 may only adjust the features surrounded by selection box 192.

Group identifier 186 indicates one of possibly several groups of programs that can be selected for delivery to patient 12. Group selection icon 184 indicates whether the displayed group, e.g., group B in FIG. 9, is actually selected for delivery to patient 12. If a presently displayed group is selected, group selection icon 184 includes a box with a checkmark. If a presently displayed group is not selected, group selection icon 184 includes a box without a checkmark. To navigate through the stored program groups, a user may use control pad 40 to move selection box 192 to select the group identifier 186 and then use control pad 40 to scroll through the various groups, e.g., A, B, C, and so forth. IMD 14 may be programmed to support a small number of groups or a large number of groups, where each group contains a small number of programs or a large number of programs that are delivered simultaneously, in sequence, or on a time-interleaved basis.

For each group, group selection icon 184 indicates the appropriate status. For a given group, program identifier 188 indicates one of the programs associated with the group. In the example of FIG. 9, no program number is indicated in program identifier 188 because all of the programs' amplitudes are shown in each bar of amplitude graph 190. Solid portions of the bars indicate the relative amplitude IMD 14 currently is using to deliver stimulation therapy to patient 12, while open portions of the bars indicate the remaining amplitude available to each program. In some examples, numerical values of each program's amplitude may be show in addition to or in place of amplitude graph 190. In other examples of user interface 168 specific to drug delivery using IMD 26, amplitude graph 190 may show the flow rate of drugs or frequency of bolus delivery to patient 12. This information may be show in numerical format as well. Patient 12 may encompass group selection icon 184 with selection box 192 to scroll between the different programs of the selected group.

Automatic posture response icon 182 indicates that IMD 14 is generally activated, such that processor 80 automatically modifies therapy to patient 12 based upon the posture state detected by posture state module 86 and timing recorded by timing unit 87. Icon 177 may indicate information about this timing, and such information (weekday 10:21 PM) may be used to select a pre-defined time slot. Automatic posture responsive therapy may involve adjusting one or more therapy parameter values, selecting different programs or selecting different program groups based on the detected posture state of the patient at a given time slot. By providing time as a separate factor to such automatic posture response, IMD 14 may provide different therapies to the patient at different times of day even if the same posture is detected at such different times of day. For example, therapy may be most aggressive when standing during the day, less aggressive when lying down during the day, even less aggressive when standing at night, and still even less aggressive when lying down at night. In another example, the upright position at 9:30 AM on the weekend may be mapped to less aggressive therapy than the same upright position at 9:30 AM on a weekday, e.g., in the case where the patient commonly works on his or her feet during the week and typically relaxes on the weekend. More aggressive therapy may refer to higher amplitudes for the stimulation. In any case, posture and timing may both factor into the therapy that is provided to patient 12. Timing may refer to time of day, day of the week, day of the month, time of day on a particular day (e.g., weekday versus weekend, or vacation day versus work day). Patient 12 may be able to adapt the therapy for different postures at different times. If automatic posture response icon 182 is not present next to group identifier 186, indicating that group "B" does not have automatic posture responsive therapy activated for any of the programs within group "B."

In addition, IMD 14 may enable a "work set" of posture states and a "home set" of posture states, each of which define different times of the day and different therapies for posture states and times of day. Also, the posture states themselves may be defined by the timing such that at different times of day, different posture detection protocols are implemented. Work posture states may be similar to home posture states, but may have different therapies associated with a given posture state and timing.

Some groups or individual programs in groups may support automatic posture responsive therapy. For example, automatic adjustment of one or more therapy parameter values in response to posture state indication and timing may be selectively activated or deactivated based on settings entered by a clinician, or possibly patient 12. Hence, some programs or groups may be configured for use with posture and timing-responsive therapy while other programs or groups may not be configured for use with posture and timing-responsive therapy. In some cases, if posture and timing-responsive therapy supported by the automatic posture response feature is desired, patient 12 may need to switch therapy to a different group that has automatic posture and timing-responsive therapy activated for IMD 14 to adjust therapy according to the patient 12 posture state and timing associated therewith.

Figure 10:
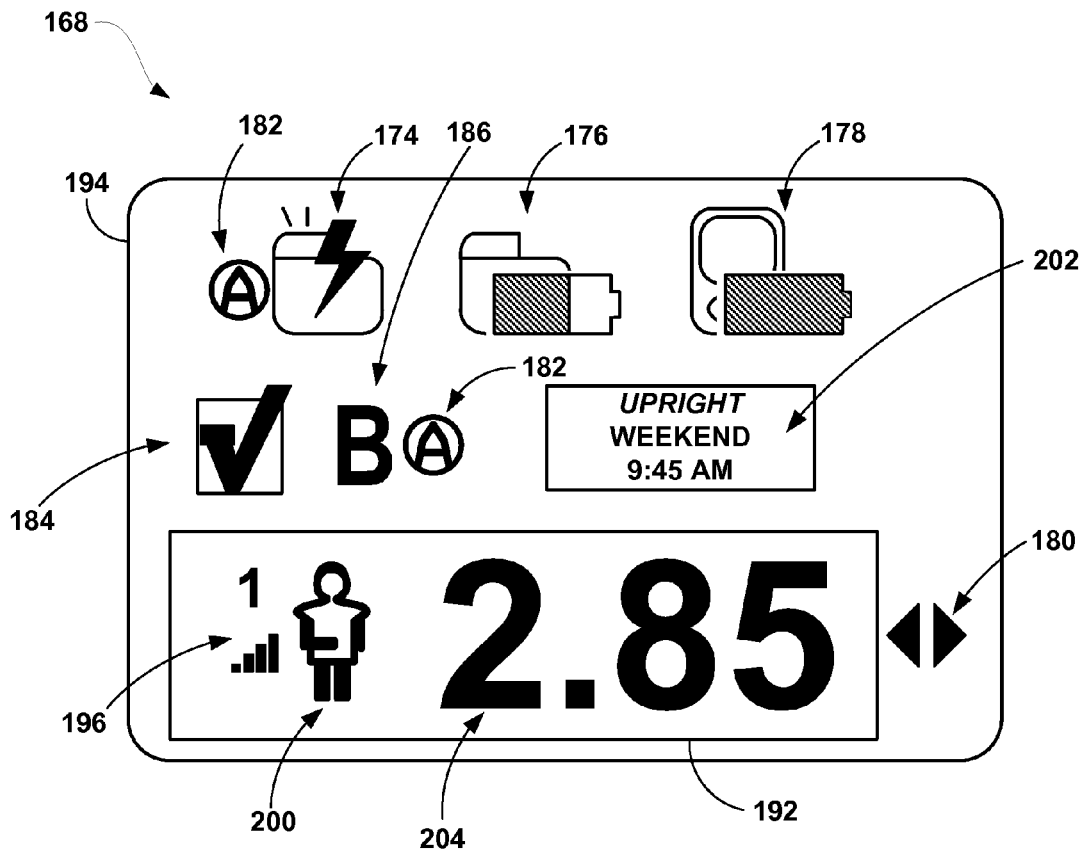
FIG. 10 is a conceptual diagram illustrating an example user interface of a patient programmer for delivering therapy information that includes posture information and timing of such posture information to the patient.

FIG. 10 is a conceptual diagram illustrating an example user interface 168 of a patient programmer 30 for delivering therapy information that includes posture information to the patient. Again, the posture information may be associated with timing of such posture information so that therapy can be defined based on posture and timing. In this case, interface 168 of patient programmer 30 may include an icon 202 that indicates the current posture and the current time. In other examples, user interface 168 may also be shown on clinician programmer 60. In the example of FIG. 10, display 36 of patient programmer 30 provides user interface 168 to the user, such as patient 12, via screen 194. Screen 194 includes stimulation icon 174, IMD battery icon 176, programmer battery icon 178, and automatic posture response icon 182, similar to screen 170 of FIG. 9. In addition, screen 194 includes group selection icon 184, group identifier 186, posture state and timing icon 202, program identifier 196, posture state indication 200, amplitude value 204, selection box 192, and selection arrows 180. User interface 168 provides information to patient 12 regarding group, program, amplitude, automatic posture response status, and posture state information. More or less information may be provided to patient 12, as desired by the clinician or the patient.

Group identifier 186 indicates that group "B" is active, and automatic posture response icon 182 indicates group "B" (containing one or more programs) is activated to allow IMD 14 to automatically adjust therapy according to the patient 12 posture state at a defined time or time interval. In the example shown in FIG. 10, user interface 168 indicates the posture state determined by IMD 14, e.g., via posture state indication 200 and posture state and timing icon 202. Program identifier 196 illustrates that information regarding program "1" of group "B" is displayed on screen 194, such as amplitude value 204 illustrating the current voltage amplitude of program "1" is 2.85 Volts. Patient 12 may scroll through different programs of the group by using navigation arrows 180 via arrows 44 and 48 of control pad 40.

In addition, posture state indication 200 shows that IMD 14 is detecting that patient 12 is in the upright or standing posture based on the output of posture state module 86 (FIG. 4). Posture state and timing icon 202 supplements posture state indication 200 by explaining in words to patient 12 the exact posture being detected by posture state module 86 of IMD 14 at any given time or time interval, which may also be displayed in icon 202. In the example of FIG. 10, for example, icon 202 includes the time of day. Time slots, e.g., from pre-defined time slots, or the day of the week, or type of day (e.g., vacation day, weekend day, weekday, or workday) may also be displayed. Posture state indication 200 and posture state and timing icon 202 presented via user interface 168 change according to the sensed, or detected, posture state detected by IMD 14 and the timing associated therewith. The posture state may be communicated to the external programmer immediately after IMD 14 detects a posture change, or communicated periodically or non-periodically by IMD 14 unilaterally or upon receiving a request from the programmer. Any timing information may also be communicated whenever posture state information is communicated. The posture state indication 200 and/or posture state and timing icon 202 may present a current, up-to-the minute status, or a status as of the most recent communication of posture state from IMD 14. Posture state indication 200 is shown as a graphical representation, but the posture state indication may alternatively be presented as any one of a symbolic icon, a word, a letter, a number, an arrow, or any other representation of the posture state. In some cases, posture state indication 200 may be presented without posture state and timing icon 202, in which case the timing information would still be used for therapy selection. Past posture states and timing associated with past posture states may be stored along with the corresponding therapy that was used for a given posture and time.

Selection box 192 indicates that patient 12 view other programs within group "B" using selection arrows 180. Selection box 192 may be moved to select other screen levels with control pad 40 (FIG. 2) of patient programmer 30 in order to navigate through other stimulation groups or adjustable elements of the therapy. When patient 12 selects a different program with control pad 40, program identifier 196 is updated to correctly identify the current program viewed on screen 194.

In addition to graphical, textual or other visible indications of posture state, the external programmer may present audible and/or tactile indications of posture state via any of a variety of audible or tactile output media. An audible indication may be spoken words stating a posture state, or different audible tones, different numbers of tones, or other audible information generated by the programmer to indicate posture state. A tactile indication may be, for example, a somatosensory indication, such as a different numbers of vibratory pulses delivered in sequence or vibratory pulses of different lengths, amplitudes, or frequencies.

Figure 11:
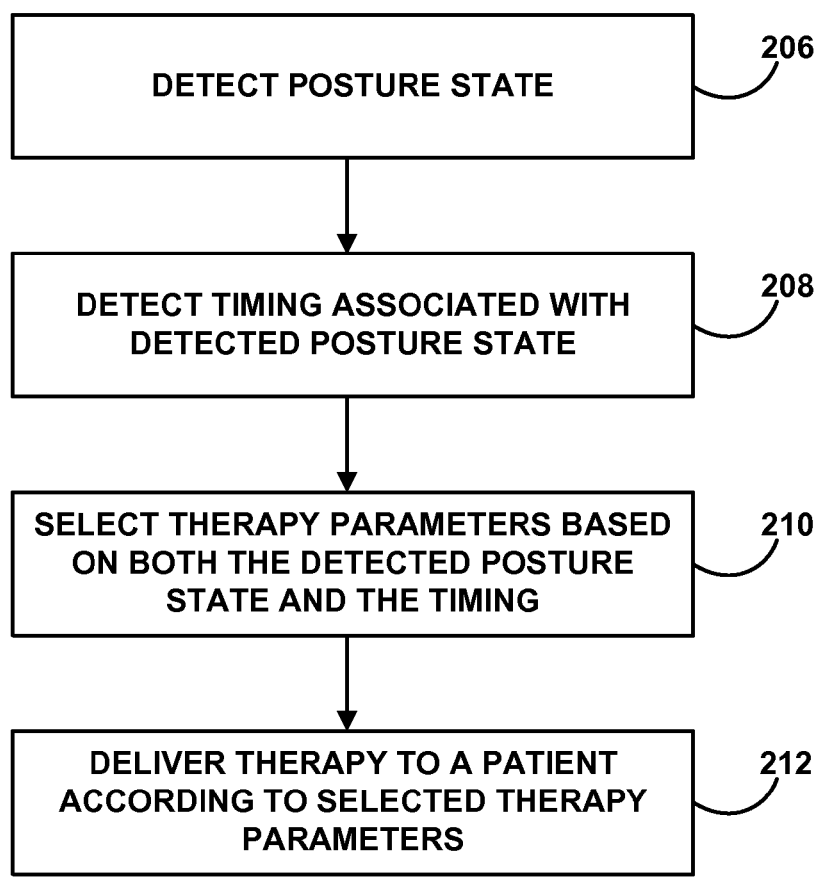
FIG. 11 is a flowchart illustrating an example technique for delivering therapy to a patient based on patient posture state and timing associated with such posture state.

FIG. 11 is a flowchart illustrating an example technique that may be implemented by IMD 14 of implantable stimulation system 10 in an automated fashion. The technique of FIG. 11 will be described from the perspective of IMD 14 of FIG. 4, although other devices could implement the same technique. As shown, posture state module 86 detects the posture state of the patient (206) and timing unit 87 detects the timing associated with the detected posture state (208). In some cases, posture state module 86 may detect not only the patient's posture but also activity associated with such posture. Thus, detection of posture state may involve the detection of a posture that quantifies both the orientation of the patient relative to the earth's surface and also movement or acceleration of the person on the earth's surface.

In one example, posture state module 86 may define pre-programmed posture states, e.g., as explained above with reference to FIGS. 8A-8C. The timing identified by timing unit 87 is timing associated with the detected posture. This timing may comprise a time of day, one of a plurality of pre-defined time slots of a day, week or other time interval, a time of a particular day such as a weekday, weekend day, holiday or vacation day, a time of a particular day of the week, a time of a particular day of the month, a time of a particular day of the year, or any other time or time interval.

In one example, days may be sub-divided into different time slots and different days may be sub-divided differently depending on the type of day. Work days associated with the patient's normal routine, for example, may be divided into morning, evening and night. Weekend or pre-selected vacation days may be similarly divided, or possibly divided into different intervals. In any case, posture state module 86 and timing unit 87 provide the detected posture state (206) and the detected timing associated with the detected posture state (208) to processor 80 for use in selecting therapy.

In particular, processor 80 selects therapy parameters for IMD 14 based on both the detected posture state and the timing (210). In this way, IMD 14 provides posture-responsive therapy that can differ depending not only on the posture of the patient, but also on the timing that such posture is detected. The selection of therapy parameters may involve selecting a set of parameters, selecting parameter adjustments, selecting therapy delivery features such as whether to enable cycling, or possibly selecting an entirely different therapy program, setting or protocol. In the case where IMD comprises an implantable electrical stimulator device, the therapy parameters may include any of a wide variety of stimulation parameters, such as pulse rate, pulse width, pulse intensity, electrode configuration, and the like. In the case where IMD comprises an implantable drug pump, the therapy parameters may include any of a wide variety of drug delivery parameters, such as delivery site, dosage, drug type, and the like. Once processor 80 has selected the therapy parameters based on the detected posture state and the timing (210), IMD 14 may deliver therapy to a patient according to the selected therapy parameters (212).

For example, processor 80 may access a lookup table or other data structure in memory 82 that maps therapy protocols to different combinations of posture state and timing. The therapy protocols may define different sets of therapy parameters to be applied by stimulation generator 84 via electrodes 16A and 16B. In the case of an implantable drug pump (FIG. 5), processor 92 may access a lookup table in memory 94 that maps therapy protocols to different combinations of posture and timing. In this case, the therapy protocols may define different sets of therapy parameters to be applied by pump module 96 via catheter 28.

Referring again to FIG. 4, processor 80 of IMD 14 controls stimulation generator 84 (FIG. 4) to generate and deliver therapy to a patient (212), e.g., in the form of electrical stimulation pulses delivered to patient 12 via stimulation leads 16A and 16B. As previously described, the electrical stimulation therapy may be provided to patient 12 according to one or more stimulation programs or protocols that define a set of stimulation parameters. Accordingly, stimulation generator 84, under the control of processor 80, may generate stimulation pulses having parameters values for stimulation parameters defined by one or more stimulation programs.

The specific parameter values defined by the stimulation programs may be appropriate for a posture state of patient 12 detected via activity module 86 at a timing determined by timing unit 87. Thus, upon detection of the posture state by posture state module 86, processor 80 may receive the timing from timing unit 87 and control stimulation generator 84 to generate and deliver therapy to patient 12 according to the one or more therapy programs associated with the detected posture state and timing. In one example of posture responsive therapy delivery, if processor 80 of IMD 14 detects that patient 12 is lying down via posture state module 86 and detects that such lying down posture occurs at nighttime via timing unit 87, processor 80 controls stimulation generator 84 according to the corresponding stimulation program in order to generate and deliver stimulation signals in accordance with the therapy program associated with the lying down state at nighttime. In this way, IMD 14 delivers a stimulation signal having a stimulation amplitude and/or other parameters that are appropriate for patient 12 when lying down at nighttime. The same lying down posture during the daytime may result in delivery of a different stimulation signal with one or more different stimulation parameters by IMD 14.

In some examples, the detection of posture state (206) may comprise the detection of a posture state transition, e.g., a transition from a first defined posture state to a second defined posture state. Posture state module 86, for example, may detect a transition from a lying down posture state to an upright posture state. As another example, posture state module 86 may detect a transition from an upright posture state to an upright and moving posture state or an upright and active posture state. Thus, posture states may be based on a combination of posture and activity, or may be based on posture alone.

In this example, the detection of timing associated with the detected posture state (208) may comprise the detection of timing associated with the posture state transition. Moreover, a lookup table in memory 82 may store therapy parameter settings or protocols for detected posture state transitions at defined times. In this case, the therapy parameter settings or protocols may define stimulation parameters or protocols, or may define changes to the therapy parameter settings or protocols, e.g., upward or downward adjustments to stimulation parameters. If the therapy parameter settings define upward or downward adjustments to stimulation parameters, the adjustments may be different for the same posture at different times of the day. For example, a change from lying down posture state to upright posture state may result in a more aggressive upward adjustment in stimulation parameters during the daytime than during the nighttime.

Any adjustments may immediately increase or drop the amplitude of the stimulation from an existing level to a desired level. Alternatively, adjustments may occur gradually over a short or extended time period. To modify electrical stimulation therapy, e.g., for a transition from lying down at nighttime to upright at nighttime, processor 80 may control stimulation generator 84 such that the amplitude of stimulation provided to patient 12 increases in value from X volts to Y volts. The adjustment from X volts to Y volts may occur substantially immediately, or may be gradual (e.g., ramped up or down) over a ramp period.

For a transition from upright posture state to lying down posture state during the daytime, as another example, processor 80 may control stimulation generator 84 to drop the amplitude from Y volts to X volts, and again, such adjustments may be immediate or gradual. Changes in therapy, as defined by posture and timing, may be quantified and stored in memory as absolute settings associated with posture and timing, or may be quantified and stored in memory as adjustments from the current settings associated with a posture state transition and timing associated therewith.

Table 1 below illustrates an example of different sets of therapy parameters, programs, setting or protocols associated with different posture states and timing. Table 1 is one illustrative example that may be stored as a lookup table in memory 82 and accessed by processor 80. Posture state and timing may comprise indices to the lookup table so that processor 80 can determine the appropriate therapy for a given posture state and timing. Each therapy program, setting or protocol in Table 1 is listed by number, and each number may define a unique set of therapy parameters to be applied by stimulation generator 84. The posture states listed in Table 1 are a small subset of the possible posture states, and are listed merely for demonstrative purposes. The timing listed in Table 1 is also a small subset of the possible timing intervals that may be defined, and are listed merely for demonstrative purposes.

TABLE 1

| POSTURE STATE | TIMING | THERAPY |
|---|---|---|
| Active and Upright | Weekday Day | 1 |
| Active and Upright | Weekday Night | 2 |
| Active and Upright | Weekend Day | 3 |
| Active and Upright | Weekend Night | 4 |
| Upright | Weekday Day | 5 |
| Upright | Weekday Night | 6 |
| Upright | Weekend Day | 7 |
| Upright | Weekend Night | 8 |
| Lying | Weekday Day | 9 |
| Lying | Weekday Night | 10 |
| Lying | Weekend Day | 11 |
| Lying | Weekend Night | 12 |

In Table 1, there are only three posture states "active and upright," "upright" and "lying." However, there are four different timings associated with each of the three posture states, e.g., "weekday day," "weekday night," "weekend day," and "weekend night." This results in twelve different therapies that may be defined for different combinations of posture state and timing. Processor 80 may access Table 1 from memory 82 based on a posture state determined by posture state module 86 and a timing determined by timing unit 87 in order to define a corresponding therapy. Processor 80 may then instruct stimulation generator 84 to apply the selected therapy.

Consistent with Table 1, there may also be posture states that are unique for a given timing interval. A leaning posture state, for example, may be useful for a bank teller on weekdays to define therapy parameters during the work day. The leaning posture state, however, may only be defined for work days and not weekend or vacation days. By only enabling specific posture states during weekday days, posture classification (discussed with respect to FIGS. 8A-8C) may be streamlined and/or simplified because the posture state detection algorithm may not need to consider the leaning posture state at some time intervals, e.g., non-work days or after work hours.

If posture state module 86 identifies the upright posture state and timing unit 87 determines that the current timing corresponds to a weekend night, then processor 80 will select therapy 8 from Table 1. However, if posture state module 86 identifies the upright posture state and timing unit 87 determine that the current timing corresponds to a weekday day, then processor 80 will select therapy 5 from Table 1. Therapy 5 may define different therapy parameters or protocols relative to therapy 8. Accordingly, the same detected posture state may result in different therapy at different times of the day. As noted, the timing may be subdivided into many different timing slots, which are not necessarily limited to any defined interval of days, weeks, months, or the like.

Table 2 below illustrates an example of different therapy protocols associated with different posture state transitions and timing. Table 2 is another illustrative example that may be stored as a lookup table in memory 82 and accessed by processor 80. In this case, however, posture state is defined by transitions from one posture state to another posture state. Posture state transitions and timing associated with such transitions may comprise indices to the lookup table so that processor 80 can determine the appropriate therapy for a given posture state and timing. Each therapy in Table 2 is listed by number, and each number may define a unique set of therapy parameters to be applied by stimulation generator 84. The posture state transitions listed in Table 2 are a small subset of the possible posture state transitions, and are listed merely for demonstrative purposes. The timing listed in Table 2 is also a small subset of the possible timing intervals that may be defined, and are listed merely for demonstrative purposes.

TABLE 2

| POSTURE STATE TRANSITION | TIMING | THERAPY MODIFICATION |
|---|---|---|
| Upright to Active and Upright | Weekday Day | 1 |
| Upright to Active and Upright | Weekday Night | 2 |
| Upright to Active and Upright | Weekend Day | 3 |
| Upright to Active and Upright | Weekend Night | 4 |
| Upright and Active to Upright | Weekday Day | 5 |
| Upright and Active to Upright | Weekday Night | 6 |
| Upright and Active to Upright | Weekend Day | 7 |
| Upright and Active to Upright | Weekend Night | 8 |
| Upright to Lying | Weekday Day | 9 |
| Upright to Lying | Weekday Night | 10 |
| Upright to Lying | Weekend Day | 11 |
| Upright to Lying | Weekend Night | 12 |
| Upright and Active to Lying | Weekday Day | 13 |
| Upright and Active to Lying | Weekday Night | 14 |
| Upright and Active to Lying | Weekend Day | 15 |
| Upright and Active to Lying | Weekend Night | 16 |
| Lying to Upright | Weekday Day | 17 |
| Lying to Upright | Weekday Night | 18 |
| Lying to Upright | Weekend Day | 19 |
| Lying to Upright | Weekend Night | 20 |
| Lying to Upright and Active | Weekday Day | 21 |
| Lying to Upright and Active | Weekday Night | 22 |
| Lying to Upright and Active | Weekend Day | 23 |
| Lying to Upright and Active | Weekend Night | 24 |

In Table 2, there are only six posture state transitions listed: "upright to active and upright," "upright and active to upright," "upright to lying," "upright and active to lying," "lying to upright" and "lying to upright and active." However, there are again four different timings associated with each of the different posture state transitions, e.g., "weekday day," "weekday night," "weekend day," and "weekend night." This results in twenty-four different therapies that may be defined for different combinations of posture state transitions and timing. Processor 80 may access Table 2 from memory 82 based on a posture state transition determined by posture state module 86 and a timing determined by timing unit 87 in order to define a corresponding therapy. Processor 80 may then instruct stimulation generator 84 to apply the selected therapy.

For example, if posture state module 86 identifies a transition for the upright posture state to a lying posture state and timing unit 87 determines that the current timing corresponds to a weekend night, then processor 80 will select therapy 12 from Table 2. However, if posture state module 86 identifies a transition from the upright posture state to the lying posture state and timing unit 87 determines that the current timing corresponds to a weekday day, then processor 80 will select therapy 9 from Table 2. Therapy 9 may define different therapy parameters or protocols relative to therapy 12. Accordingly, the same detected posture transition may result in delivery of different therapy at different times of the day. Again, the timing may be subdivided into many different timing slots, which are not necessarily limited to any defined interval of days, weeks, months, or the like.

In yet another example, the different numbered therapies listed in table 2 may comprise therapy adjustments, e.g., upward or downward adjustments to stimulation intensity. In this case, the same detected posture state transitions may result in different therapy adjustments at different times of day. In this example, therapy 9 may define a more aggressive adjustment to one or more therapy parameters than therapy 12, or vice versa.

In some examples, posture state module 86 of IMD 14 detects six different posture states (or possibly more). With six posture states, there may be up to thirty different posture state transitions between those six posture states. Each therapy listed in Table 2 may define a unique modification profile in the sense that it defines different parameters, different rates of change, different transition periods between such parameter changes, different dwell times at such parameters, or the like. The phrase "dwell time" refers to the time in which a patient must be classified in a posture state before a change in therapy is initiated in response to detection of the posture state. Alternatively, some of the modification profiles may be the same for different posture state transitions and timing. For example, transitions to or from any of the lying down posture states could result in the same therapy modification regardless of time. At least one type of transition, in accordance with this disclosure, may define different therapies at different times of the day. Days may be divided or subdivided, and different types of days may be defined in order to promote patient-specific therapy that is defined based on a patient's routine. Posture state and timing may be used to select therapy for any given day, and posture state and timing may ensure that a particular routine of the patient is being followed prior to adjusting therapy at that time.

To determine (or detect) posture state transitions, for example, IMD 14 may periodically detect the posture state occupied by patient 12, e.g., at a frequency of several times per second. In one example, processor 80 of IMD 14 compares the current posture state of patient 12 detected via posture state module 86 to a previously detected posture state of patient 12, e.g., the posture state detected just prior to the current posture state, which may be stored in memory 82. If the two detected posture states are the same, IMD 14 may continue to deliver electrical stimulation without modification unless the time interval changes, in which case the electrical stimulation may change even if posture state does not. If the two detected posture states are different, processor 80 may modify the stimulation therapy by adjusting the amplitude parameter value according to a corresponding modification profile, which again may be defined based on both posture state and timing.

The examples herein present a wide variety of techniques for providing different modification profiles when a transition from one posture state to another posture state and timing associated therewith are detected. Such examples are provided for purposes of illustration and should not be considered limiting of the techniques as broadly described in this disclosure. The types of therapy changes that may be defined for different combinations of posture states and time are subject to a wide variety of implementations.

Consistent with FIG. 11, an IMD may further include sets of posture states classified by patient activity. For example, the IMD may allow for selection of a set of "work posture state definitions" in contrast to "home posture state definitions." Different sets of posture states may define different numbers of posture states, different therapies and different timings for therapies at given posture states. Also, different sets of posture states may define different vectors, hysteresis zones and/or tolerances for posture state classifications or the actual detection of posture states.

In accordance with another aspect of this disclosure, IMD 14 may be configured to learn and apply therapy based on patient feedback. The patient feedback may comprise therapy selections, or possibly therapy adjustments. In this case, IMD 14 may associate any therapy selections or adjustments with the corresponding posture states and timing associated with the detected posture states when the selection or adjustment is made. IMD 14 may later apply the same therapy automatically, e.g., in a subsequent day, upon detecting the same posture states and timing. In this way, if a patient defines a particular therapy for a lying down posture state at nighttime on a weekday, that same therapy may be auto-programmed to apply in a subsequent day for the same lying down posture state at nighttime. If the same patient defines a different therapy for lying down posture in the daytime of a weekend, that different therapy may be similarly auto-programmed.

Thereafter, without further patient changes, the same therapies may be automatically applied by IMD 14 upon detecting a specific posture state and timing that was previously programmed by the patient using the external programmer. In this way, IMD 14 may be programmed over time to apply patient-specific therapy adjustments that are specifically defined by the patient consistent with the daily or weekly routine of the patient. Different types of days may also be defined, e.g., weekend day, vacation day, weekday, different days of the week, workday, special day, and so forth, and different therapies may be defined by IMD 14 for time slots of these different days based on posture state and timing. A patient may be able to select a type of day, and in response, IMD 14 may apply therapies based on posture and timing that are specifically defined for the routine of the patient on those types of days. Different therapy protocols may be defined or learned for each of a plurality of different types of days, and the patient may simply select the type of day in order to ensure therapy delivery consistent with the defined or learned therapy protocols for that type of day.

Such patient directed changes to the therapy provided by IMD 14 may be characterized as a learning mode, and the patient may be allowed to confirm whether any therapy change should be made at a particular time and posture. Learning mode may be selected for IMD 14 via a programmer, and confirmation may also be required via clinician approval for changes outside of a particular range. An icon or indicator may be presented to the user via the IMD to show that learning mode is enabled (similar to icon 182 of FIG. 10), and/or to show that therapy is being initiated or provided in accordance with programming that occurred via a previous learning mode. The timing for application of therapy defined by the learning mode may also be displayed (e.g., similar to element 202 of FIG. 10). In this way, IMD 14 may present an indicator to the user identifying an automatic adjustment to the new therapy at the time of day that such automatic adjustment is scheduled to occur on one or more subsequent days.

Figure 12:
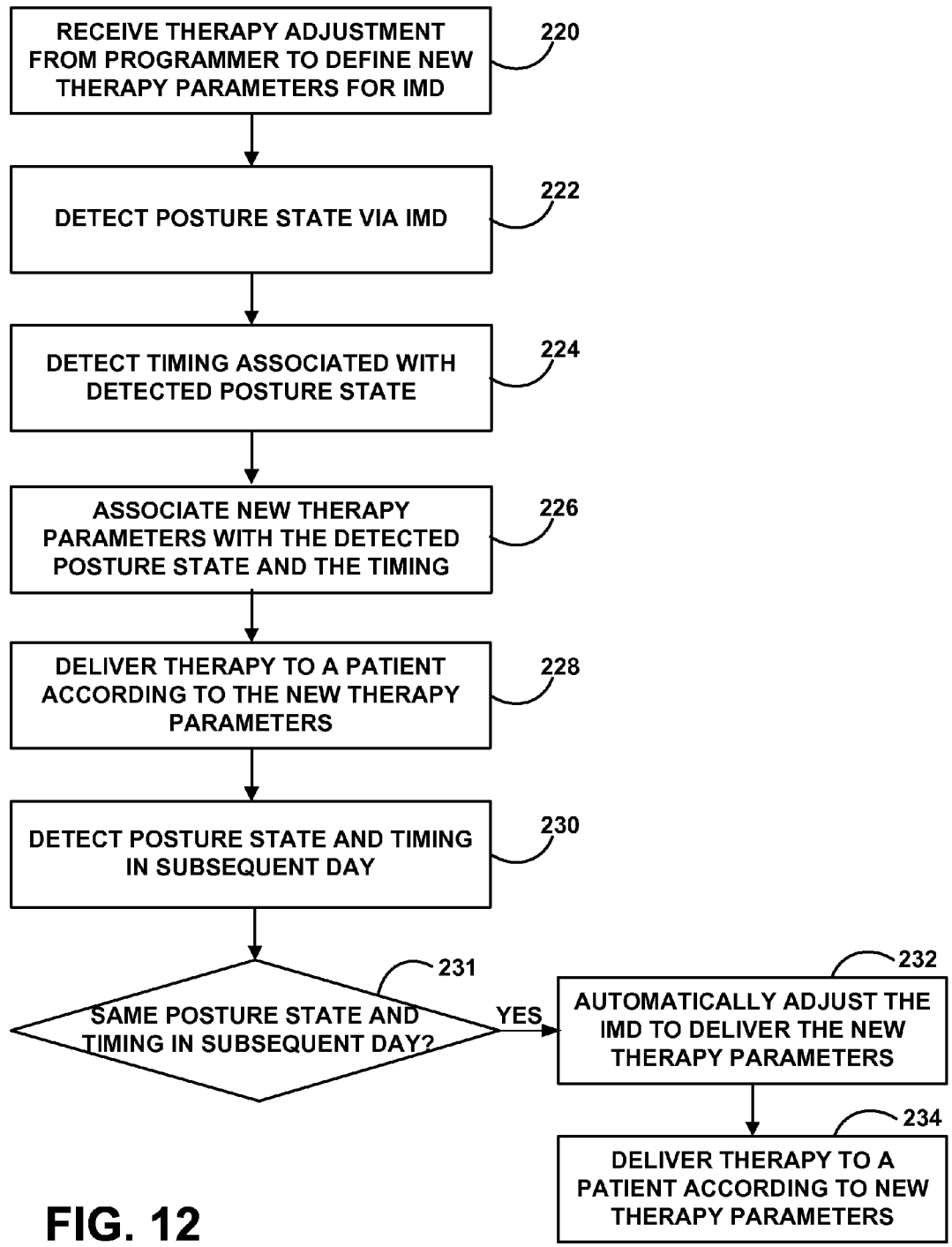
FIG. 12 is a flowchart illustrating an example technique for associating a therapy adjustment to a detected a posture state transition of a patient and timing associated with the posture state transition.

FIG. 12 is flow diagram illustrating a technique that may be executed by an implantable medical device system to provide auto-learning of posture and timing-based therapy in an implantable medical device. As shown, IMD 14 receives a therapy adjustment from a programmer to define new therapy parameters for IMD (220). In particular, telemetry circuit 88 may receive this therapy adjustment, which may take the form of an upward or downward adjustment to intensity, the selection of one or more new parameters, or the selection of an entirely different therapy protocol.

Upon receiving the therapy adjustment (220), IMD 14 detects a posture state (222) and detects timing associated with the detected posture state (224). For example, as outlined above, posture state module 86 may detect a posture state from a plurality of pre-defined posture states, and timing unit 87 may detect the timing associated with the detected posture state. Processor 80 receives the detected posture state from posture state module 86 and receives the timing associated with the detected posture state from timing unit 87. Processor 80 then associates the new therapy parameters with the detected posture state and the timing (226), either automatically or upon patient approval. For example, processor 80 may update a lookup table in memory 82 to map the detected posture and the timing associated with the detected posture to the new therapy parameters received in the therapy adjustment. The patient programmer, in this case, may prompt the user for approval of any therapy parameter changes, particularly if such changes are to be applied automatically for subsequently detected posture and the timing.

IMD 14 may then deliver therapy to patient 12 according to the new therapy parameters. In particular, processor 80 may command stimulator generator 84 to provide stimulation therapy via electrodes 16A and 16B according to the new therapy parameters. Alternatively, in the case where the IMD is an implantable drug pump (FIG. 5), processor 92 may command pump module 96 to provide drug therapy via catheter 28 according to the new therapy parameters. This therapy may continue for a defined period of time assuming that posture does not change in a manner that would cause a therapy change.

IMD 14 may then detect posture state and timing in a subsequent day or other time interval (230). In this case, IMD 14 again detects posture state and timing via posture state module 86 and timing unit 87. Posture state module 86 may detect a posture state from a plurality of pre-defined posture states, and timing unit 87 may detect the timing associated with the detected posture state, e.g., in a subsequent day. Processor 80 receives the detected posture state from posture state module 86 and receives the timing associated with the detected posture state from timing unit 87. If processor 80 determines that IMD 14 has detected the same posture state and the same timing (e.g., the same time of day) in a subsequent day ("yes" 231), processor 80 automatically adjusts the IMD to deliver the new therapy parameters (232) and causes IMD 14 to deliver therapy according to the new therapy parameters (234). If IMD 14 does not detect the same posture and the same timing, then IMD 14 continues its normal operation, which may call for delivery of therapy according to a default or previously defined set of therapy parameters ("no" branch of 231 not shown in FIG. 12 for simplicity and ease of illustration).

Thus, according to the process of FIG. 12, IMD 14 can receive patient feedback that defines or adjusts therapy. In response to any adjustment of therapy, IMD determines the posture state and timing, and stores this association. Thereafter, if IMD 14 detects the same posture and timing is later (e.g. in a subsequent day or a specific subsequent day defined by the timing), IMD 14 may automatically adjust to deliver the therapy defined for that posture and timing. If desired, an associated programmer may also present an indication or icon to the user that defines the automatic adjustment to the new therapy at the time of day for one or more subsequent days. This indication, for example, may be provided in a manner similar to icons 182 and 202 shown in FIG. 10. Icons 182 and 202 shown in FIG. 10 represent an indication of auto mode for posture-responsive therapy (182) and the current time of day (202), but similar icons could be used to define automatic adjustment and the expected timing of an future therapy adjustments caused by such automatic adjustment.

In still other examples, IMD 14 may allow for a user to program new time periods to define posture and timing specific therapy. Programmer 20 may receive input from a user defining a new time period, receive a selection of new therapy parameters, and program IMD 14 for the new time period. In this case, posture state module 86 detects posture state of the patient during the new time period. Processor 80 then associates the new therapy parameters with both the detected posture state during the new time period and a time of day defined by the new time period (from timing unit 87), and causes a therapy unit (such as stimulation generator 84) to automatically deliver therapy to the patient according to the selected new therapy parameters during the new time period for one or more subsequent days without any input from the user to select or adjust the therapy parameters for IMD 14.

In this way, a user may be able to define new time periods for posture responsive therapy. The technique of FIG. 12 may then be applied with respect to the new time periods so that IMD 14 can learn therapy that is specific to a particular patient's routine, and responsive to the therapy needs during the patient's routine.

The various therapy parameters discussed above are merely exemplary of a wide range of possible parameters and therapy delivery features of an IMD that may be selected, identified, defined or adjusted in the manner described herein. Other types of parameters or features could also be used as therapy parameters. Moreover, the posture states and timings discussed above are also exemplary of a wide range of possible posture states and timings. Time of day or time slots within a day may be defined and used along with posture states to define therapy. However, timing is not necessarily limited to daily cycles, and in some cases, different types of days may define different time slots. Weekdays, specific days of the week (Mondays, Tuesdays, Wednesdays, etc.), weekend days, vacation days and sick days are specific examples of different types of days. However, the patient or clinician may define timings in any manner so that the timing may be used along with posture state information to define therapy during different times.

In added embodiments, this disclosure also contemplates allowing a user to define different sets of posture states for use at different times of day or different days of the week. For example, the patient may have "work posture states" that are not used at night or on weekends, or activity-related posture states (e.g., "quilting posture states" or "bowling posture states") not used during work. Each set of posture states could include different tolerances for a same vector, different vectors, different hysteresis zones, and so on. In this case, by only enabling posture states that are used during a particular time of time, posture state classification may be simplified or improved. Power usage may also be reduced by avoiding the need to check some posture states at times when such posture states are not defined in the system. Moreover, since the tolerances may be different at different times of day, more accurate classification may occur.

This disclosure also contemplates the ability for users (e.g., patients, physicians or clinicians) to implement schedule changes. The IMD, for example, may support a "schedule change" mode such that the user may change a patient-specific activity defined for one time period to occur in a different time period. Thus, if the patient were planning an activity on an atypical day (e.g., atypical relative to a patient's normal routine), this "schedule change" mode may allow for quick and accurate activation of the patient-specific activity responsive therapy at a new time.

The techniques described in this disclosure may be implemented, at least in part, in hardware, software, firmware or any combination thereof. For example, various aspects of the techniques may be implemented within one or more microprocessors, DSPs, ASICs, FPGAs, or any other equivalent integrated or discrete logic circuitry, as well as any combinations of such components, embodied in programmers, such as physician or patient programmers, stimulators, or other devices. The term "processor" or "processing circuitry" may generally refer to any of the foregoing logic circuitry, alone or in combination with other logic circuitry, or any other equivalent circuitry.

Although various aspects of this disclosure have been described as being performed by an IMD, some aspects may also be performed by a programmer, or distributed between both the IMD and the programmer. For example the selection and adjustment of therapy parameters may occur in a programmer, in response to detected posture by an IMD. The timing may be detected by the IMD, or if the posture detection is communicated to the programmer in real-time, the timing may be defined by the programmer. Accordingly, the therapy parameter adjustments described herein may be executed by the IMD or by a programmer that programs the IMD.

Moreover, although the techniques of this disclosure have been described in the context of implantable medical devices, the techniques may also apply to trial devices, or other medical devices that are not necessarily implantable, or only partially implantable. The term medical device refers to any type of medical device, including implantable medical devices, implanted medical devices, external medical devices, trial medical devices, non-implanted medical devices, or other medical devices.

When implemented in software, the functionality ascribed to the systems and devices described in this disclosure may be embodied as instructions on a computer-readable medium such as RAM, ROM, NVRAM, EEPROM, FLASH memory, magnetic media, optical media, or the like. The instructions may be executed to support one or more aspects of the functionality described in this disclosure.

In addition, it should be noted that the systems described herein may not be limited to treatment of a human patient. In alternative examples, these systems may be implemented in non-human patients, e.g., primates, canines, equines, pigs, and felines. These animals may undergo clinical or research therapies that my benefit from the subject matter of this disclosure.

Many examples have been described. Various modifications may be made without departing from the scope of the claims. These and other examples are within the scope of the following claims.

The invention claimed is:

1. A medical device system comprising:
an implantable medical device that includes:
a therapy delivery unit that delivers therapy to a patient,
a posture state module that detects a posture state of the patient,
a timing unit that detects timing associated with the detected posture state, and
a processor; and
a programmer device, wherein the programmer device:
receives input from a user defining a time interval, a particular posture state, and a new set of therapy parameters for the time interval and the particular posture state, and
programs the implantable medical device based on the inputs,
wherein, in response to the implantable medical device being programmed based on the inputs and by the programmer device, the processor causes the therapy delivery unit to deliver therapy to the patient according to the new set of therapy parameters upon subsequently detecting the particular posture state during the time interval.

2. The medical device system of claim 1, wherein the posture state module detects a posture transition from a first posture state to a second posture state.

3. The medical device system of claim 1, wherein the posture state module detects the posture state from a plurality of pre-defined posture states.

4. The medical device system of claim 3, wherein the plurality of posture states includes a first posture state defining a first posture and a second posture state defining the first posture in conjunction with an activity.

5. The medical device system of claim 3, wherein the plurality of posture states includes a first posture state defining a first posture and a second posture state defining a second posture.

6. The medical device system of claim 1, wherein the timing unit detects a time of day.

7. The medical device system of claim 1, wherein the timing unit detects a day of the week and a time of the day and the processor defines different therapies for similar times of different days for at least one posture state of a plurality of posture states.

8. The medical device system of claim 1, wherein the timing unit detects a time interval and the processor defines different therapies for different time intervals of one or more days.

9. The medical device system of claim 1, wherein the medical device system comprises one or more of:
an implantable stimulation device, and
an implantable drug pump.

10. The medical device system of claim 1, wherein the medical device system includes a memory that stores a lookup table that maps a set of posture states and timings of the postures states with different sets of therapy parameters, wherein upon detecting the particular posture state during the time interval, the medical device system performs a lookup in the lookup table.

11. The medical device system of claim 1, wherein the posture state module, the timing unit and the processor all reside within the implantable medical device.

12. The medical device system of claim 1, wherein the posture state module and the timing unit reside in the implantable medical device, and the processor resides in the programmer device.

13. The medical device system of claim 1, wherein the detected timing is associated with a defined activity that occurs at a particular time of a particular day.

14. The medical device system of claim 1, wherein the detected timing is associated with a particular type of day defined by the patient.

15. The medical device system of claim 1, wherein the medical device defines a set of posture states for a particular time, and wherein the posture states in the set of posture states for the particular time define different sets of therapy parameters for the particular time.

16. The medical device system of claim 1, wherein a manner in which the medical device detects the posture state is dependent upon the detected timing.

17. The medical device system of claim 1, wherein the time interval is defined as at least one of a specific time of a day, a specific day of a week, and a specific day of a month.

18. The medical device system of claim 1, wherein the time interval is defined as at least one of a plurality of pre-defined time slots.

19. A medical device system comprising:
an implantable medical device comprising:
a therapy delivery unit that delivers therapy to a patient,
a posture state module that detects a posture state of the patient,
a timing unit that detects timing associated with the detected posture state, and
a processor; and
a programmer device, wherein the programmer device:
receives input from a user that defines a therapy adjustment, and programs the processor to apply a new therapy defined by the therapy adjustment,
wherein the processor determines a particular posture state of the patient at a time associated with the therapy adjustment, records the time associated with the therapy adjustment, and subsequently associates the new therapy defined by the therapy adjustment with the particular posture state and the time associated with the therapy adjustment.

20. The medical device system of claim 19, wherein the time associated with the therapy adjustment comprises a time of day, wherein the processor:
automatically adjusts the medical device system to deliver the new therapy defined by the therapy adjustment in a subsequent day in response to detecting the particular posture state and the time on the subsequent day.

21. The medical device system of claim 20, wherein the programmer device presents an indicator to the user identifying an automatic adjustment to the new therapy at the time of day for one or more subsequent days.

22. A medical device system comprising
an implantable medical device comprising:
a therapy delivery unit that delivers therapy to a patient,
a posture state module that detects a posture state of the patient,
a timing unit that detects timing associated with the detected posture state, and
a processor; and
a programmer device, wherein the programmer device:
receives input from a user defining a time period,
receives a selection of new therapy parameters, and
programs the implantable medical device for the time period, wherein the posture state module detects a particular posture state of the patient during the time period, and
wherein the processor associates the new therapy parameters with both the particular posture state during the time period and a time of day defined by the time period, and causes the therapy unit to automatically deliver therapy to the patient according to the selected new therapy parameters during the time period for one or more subsequent days upon subsequently detecting the particular posture state without any input from the user to select or adjust the therapy parameters for the implantable medical device.

23. A system comprising: means for detecting a posture state of a patient; means for detecting timing associated with the detected posture state; means for delivering therapy to a patient device; means for receiving input from a user defining a time interval, a particular posture state, and a new set of therapy parameters for the time interval and the particular posture state; means for programming a medical device based on the inputs, wherein, in response to being programmed based on the inputs and by the means for programming, the medical device delivers therapy to the patient according to the new set of therapy parameters upon subsequently detecting the particular posture state during the time interval.

24. A method comprising:
detecting, via a posture state module of a medical device system, a posture state of a patient;
detecting, via a timing unit of the medical device system, timing associated with the detected posture state;
receiving, via a programmer device of the medical system, input from a user defining a time interval, a particular posture state, and a new set of therapy parameters for the time interval and the particular posture state; and
delivering, via a therapy delivery unit of the medical device system, therapy to the patient according to the new set of therapy parameters upon subsequently detecting the particular posture state and the time interval.

25. The method of claim 24, wherein detecting the posture state comprises detecting a posture transition from a first posture state to a second posture state.

26. The method of claim 24, wherein detecting the posture state comprises selecting among a plurality of pre-defined posture states.

27. The method of claim 26, wherein the plurality of pre-defined posture states includes a first posture state defining a first posture and a second posture state defining the first posture in conjunction with an activity.

28. The method of claim 26, wherein the plurality of pre-defined posture states includes a first posture state defining a first posture and a second posture state defining a second posture.

29. The method of claim 24, wherein detecting timing comprises detecting a time of day.

30. The method of claim 24, wherein detecting timing comprises detecting a day of the week and a time of the day.

31. The method of claim 24, wherein detecting timing comprises detecting a time interval.

32. The method of claim 24, wherein delivering therapy comprises one of:
delivering, via an implantable stimulation device of the medical device system, stimulation pulses, and
delivering, via an implantable drug pump of the medical device system, drug therapy.

33. The method of claim 24, wherein a memory of the medical device system stores a lookup table that maps posture states and timings of the postures states with therapy parameters, wherein delivering therapy to the patient according to the new set of therapy parameters upon detecting the particular posture state and the time interval comprises performing a lookup in the lookup table.

34. The method of claim 24, wherein selecting the therapy parameters comprises adjusting the therapy parameters.

35. The method of claim 24, wherein the medical device system is an implantable medical device and the method is performed by the implantable medical device.

36. The method of claim 24, wherein the medical device system comprises an implantable medical device and a programmer device for the implantable medical device, wherein the method is performed by the implantable medical device and the programmer device for the implantable medical device.

37. The method of claim 24, wherein the detected timing is associated with a defined activity that occurs at a particular time of a particular day.

38. The method of claim 24, wherein the detected timing is associated with a particular type of day defined by the patient.

39. The method of claim 24, wherein the medical device system defines a set of posture states for a particular time, and wherein the posture states in the set of posture states for the particular time define different sets of therapy parameters for the particular time.

40. The method of claim 24, wherein a manner in which the posture state module detects the posture state is dependent upon the detected timing.

41. A method comprising:
- detecting, via a posture state module of a medical device system, a posture state of a patient;
- detecting, via a timing unit of the medical device system, timing associated with the detected posture state;
- receiving, via a programmer device of the medical device system, input from a user that defines a therapy adjustment;
- determining, via a processor of the medical device system, a particular posture state of the patient at a time associated with the therapy adjustment;
- recording, via the processor, the time associated with the therapy adjustment; and
- associating, subsequent to the determining and the recording and via the processor, a new therapy defined by the therapy adjustment with the particular posture state and the time associated with the therapy adjustment.

42. The method of claim 41, wherein the time associated with the therapy adjustment comprises a time of day, the method further comprising:
- automatically adjusting, via the processor, the therapy delivery unit to deliver the new therapy defined by the therapy adjustment in a subsequent day in response to detecting the particular posture state and the time on the subsequent day.

43. The method of claim 41, further comprising:
- presenting, via the programmer device, an indicator to the user identifying an automatic adjustment to the new therapy at the time of day for one or more subsequent days.

44. A method comprising:
- detecting, via a posture state module of a medical device system, a posture state of a patient;
- detecting, via a timing unit of the medical device system, timing associated with the detected posture state;
- receiving, via a programmer device of the medical device system, input from a user defining a time period;
- detecting, via the posture state module, a particular posture state of the patient during the time period;
- receiving, via the programmer device, a selection of new therapy parameters;
- associating, via a processor of the medical device system, the new therapy parameters with both the particular posture state during the time period and a time of day defined by the time period; and
- automatically delivering, via a therapy delivery unit of the medical device system, therapy to the patient according to the selected new therapy parameters during the time period for one or more subsequent days upon subsequently detecting the particular posture state without any input from the user to select or adjust the therapy parameters for the medical device.

45. A computer-readable storage medium comprising instructions that when executed in a medical device system cause the medical device system to:
- detect a posture state of a patient via a posture state module of a medical device of the medical device system;
- detect timing associated with the detected posture state via a timing unit of the medical device of the medical device system;
- receive, via a programmer device of the medical device system, input from a user defining a time interval, a particular posture state, and a new set of therapy parameters for the time interval and the particular posture state;
- program a processor of the medical device system via the programmer device based on the inputs; and
- deliver therapy to a patient via the medical device according to the new set of therapy parameters upon subsequently detecting the posture state and the time interval via the medical device of the medical device system.

* * * * *